(12) United States Patent
Li et al.

(10) Patent No.: US 12,070,444 B2
(45) Date of Patent: *Aug. 27, 2024

(54) MODULATION OF MOLECULAR MARKERS USING S-EQUOL

(71) Applicant: Board of Regents, The University of Texas System, Austin, TX (US)

(72) Inventors: Rong Li, Washington, DC (US); Bin Yuan, Hefei (CN); Kate Ida Lathrop, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/535,125

(22) Filed: Nov. 24, 2021

(65) Prior Publication Data
US 2022/0160678 A1 May 26, 2022

Related U.S. Application Data

(60) Provisional application No. 63/117,888, filed on Nov. 24, 2020.

(51) Int. Cl.
| | |
|---|---|
| *A61K 31/353* | (2006.01) |
| *A61K 39/00* | (2006.01) |
| *A61K 39/395* | (2006.01) |
| *A61P 35/00* | (2006.01) |
| *C07K 16/28* | (2006.01) |

(52) U.S. Cl.
CPC ...... *A61K 31/353* (2013.01); *A61K 39/39541* (2013.01); *A61P 35/00* (2018.01); *C07K 16/2818* (2013.01); *C07K 16/2827* (2013.01); *A61K 2039/505* (2013.01); *C07K 2317/21* (2013.01); *C07K 2317/24* (2013.01)

(58) Field of Classification Search
CPC ............ A61K 31/353; A61K 39/39541; A61K 2039/505; A61K 39/3955; A61P 35/00; C07K 16/2818; C07K 16/2827; C07K 2317/21; C07K 2317/24; C07K 2317/76
See application file for complete search history.

(56) References Cited

U.S. PATENT DOCUMENTS

| | | | |
|---|---|---|---|
| 11,090,286 B2 * | 8/2021 | Li ...................... | A61K 31/353 |
| 2016/0102070 A1 * | 4/2016 | Jackson ................ | A61P 5/14 |
| | | | 549/406 |

FOREIGN PATENT DOCUMENTS

| | | |
|---|---|---|
| WO | 2019240871 A1 | 12/2019 |
| WO | 2019240872 A1 | 12/2019 |

OTHER PUBLICATIONS

Karami, Chem Biol. Drug Des. 2016; 87: 317-320 (Year: 2016).*
Wang. FASEB J., 2018, vol. 32, p. 1537-1549 (Year: 2018).*
Dirix (Breast Cancer Research Treatment vol. 167, p. 671-686, published 2017) (Year: 2017).*
Given. Asia-Pacific Journal of Oncology Nursing, vol. 4. Iss 4. 2017, 275-282 (Year: 2017).*
NCT02352025. Clinical Trial NCT02352025, published Jan. 30, 2015 (Year: 2015).*
International Search Report and Written Opinion in PCT/US21/60788 mailed Mar. 17, 2022, 15 pages.
Altin, J.G. and Sloan, E.K. The role of CD45 and CD45-associated molecules in T cell activation. Immunol. Cell Biol. 75(5):430-435 (1997).
Azuma, K. & Inoue, S. Genomic and non-genomic actions of estrogen: recent developments. Biomol Concepts 3, 365-370, doi:10.1515/bmc-2012-0002 (2012).
Banerjee, S., Chambliss, K. L., Mineo, C. & Shaul, P. W. Recent insights into non-nuclear actions of estrogen receptor alpha. Steroids 81, 64-69, doi:10.1016/j.steroids.2013.11.002 (2014).
Baum M., Buzdar A.U., Cuzick J., et al. Anastrozole alone or in combination with tamoxifen versus tamoxifen alone for adjuvant treatment of postmenopausal women with early breast cancer: first results of the ATAC randomized trial. Lancet. 359: 2131-2139, (2002).
Beelen K., Zwart W., Linn S.C. Can predictive biomarkers in breast cancer guide adjuvant endocrine therapy? *Nat Rev Clin Oncol.* 9: 529-541, (2012).
Bjornstrom, L. & Sjoberg, M. Mechanisms of estrogen receptor signaling: convergence of genomic and nongenomic actions on target genes. Mol Endocrinol 19, 833-842, doi:10.1210/me.2004-0486 (2005).
Brahmer, J. R. et al. Safety and activity of anti-PD-L 1 antibody in patients with advanced cancer. *N Engl J Med 366*, 2455-2465, doi:10.1056/NEJMoa1200694 (2012).
Brower, V. Checkpoint blockade immunotherapy for cancer comes of age. *J Natl Cancer Inst 107*, doi: 10.1093/jnci/djv069 (2015).
Chen, L. & Flies, D. B. Molecular mechanisms of T cell co-stimulation and co-inhibition. *Nat Rev Immunol 13*, 227-242, doi:10.1038/nri3405 (2013).

(Continued)

*Primary Examiner* — Jeffrey H Murray
*Assistant Examiner* — Luisalberto Gonzalez
(74) *Attorney, Agent, or Firm* — ROTHWELL, FIGG, ERNST & MANBECK, P.C.

(57) ABSTRACT

The present invention provides methods and compositions for modulating molecular markers, and hence treating or preventing breast cancer (e.g., triple-negative breast cancer) and melanoma with a pharmaceutically effective amount of S-equol or a pharmaceutical composition comprising S-equol. The S-equol may be administered alone or in combination with one or more cytotoxic or immunotherapeutic compound or molecule.

16 Claims, 59 Drawing Sheets
(7 of 59 Drawing Sheet(s) Filed in Color)
Specification includes a Sequence Listing.

(56) References Cited

OTHER PUBLICATIONS

Chia, K. & Tutt, A. Triple-negative breast cancer: An update. *Adv Breast Cancer* 4, 75-80, (2007).
Cho, J. L., Allanson, M. & Reeve, V. E. Oestrogen receptor-beta signalling protects against transplanted skin tumour growth in the mouse. *Photochem Photobiol Sci* 9, 608-614, doi: 10.1039/b9pp00168a (2010).
Clark CA, Gupta HB, Sareddy G, Pandeswara S, Lao S, Yuan B, Drerup JM, Padron A, Conejo-Garcia J, Murthy K, Liu Y, Turk MJ, Thedieck K, Hurez V, Li R, Vadlamudi R, Curiel TJ. Tumor-Intrinsic PD-L1 Signals Regulate Cell Growth, Pathogenesis, and Autophagy in Ovarian Cancer and Melanoma, *Cancer Res.* Dec. 1, 2016;76(23):6964-6974.
Clarke R., Liu M., Bouker K.B., et al. Antiestrogen resistance in breast cancer and the role of estrogen receptor signaling. *Oncogene.* 22: 7316-7339, (2003).
Cleator, S., Heller, W. & Coombes, R. C. Triple-negative breast cancer: therapeutic options. *Lancet Oncol.* 8, 235-244, (2007).
Coates et al. "Tailoring therapies—improving the management of early breast cancer: St. Gallen International Expert Consensus on the Primary Therapy of Early Breast Cancer 2015," *Annals of Oncology* 26(8):1533-46, (2015).
Courtney AH, Lo W-L, Weiss A. Ter signaling: mechanisms of initiation and propagation. *Trends Biochem Sci* 2018;43:108-23.
Curiel, T. J. et al. Blockade of B7—H1 improves myeloid dendritic cell-mediated antitumor immunity. *Nat Med* 9, 562-567, doi:10.1038/nm863 (2003).
Davies C., Pan H., Godwin J., et al. Long-term effects of continuing adjuvant tamoxifen to 10 years versus stopping at 5 years after diagnosis of estrogen receptor-positive breast cancer: Atlas, a randomized trial. *Lancet.* 381: 805-816, 2013.
Dawood, S. & Rugo, H. S. Targeting the host immune system: PD-1 and PD-L 1 antibodies and breast cancer. *Curr Opin Support Palliat Care* 10, 336-342, doi:10.1097/SPC.0000000000000243 (2016).
Dent, R. et al. Triple-negative breast cancer: clinical features and patterns ofrecurrence. *Clin Cancer Res.* 13, 4429-4434 (2007).
Deroo B.J., Korach K.S. Estrogen receptors and human disease. *J Clin Invest.* 116: 561-570, (2006).
Deroo B.J., Buensuceso A.V. Minireview: Estrogen receptor-beta: mechanistic insights from recent studies. *Mol Endocrinol.* 24: 1703-1714, (2010).
Diaz, L. K., Cryns, V. L., Symmans, W. F. & Sneige, N. Triple negative breast carcinoma and the basal phenotype: From expression profiling to clinical practice. *Advances in Anatomic Pathology* 14, 419-430 (2007).
Dirix, L. Y., Takacs, I. & Nikolinakos, P. e. a. Avelumab (MSB0010718C), an anti-PD-LI antibody, in patients with locally advanced or metastatic breast cancer: A phase 1b JA YELIN solid tumor trial. 2015 San Antonio Breast Cancer Symposium Abstract S1-04, (2015).
Emens, L. A., Braiteh, F. S. & Cassier, P. e. a. Inhibition of PD-L 1 by MPDL3280A leads to clinical activity in patients with metastatic triple-negative breast cancer (TNBC). The American Association for Cancer Research Annual Meeting Abstract 2859, (2015).
Fan, X. et al. Gonadotropin-positive pituitary tumors accompanied by ovarian tumors in aging female ERbeta−/− mice. Proc Natl Acad Sci U S A 107, 6453-6458, doi:1002029107 [pii] 10.1073/pnas.1002029107 (2010).
Gerson, R., Alban, F., Villalobos, A. & Serrano, A. Recurrence and survival rates in early breast cancer cases with triple negative immunophenotype. *Gae Med Mex* 144, 27-34, (2008).
Gonzalez-Angulo, A. M. Advances in triple receptor-negative breast cancer. *Clin Adv Hematol Oncol* 5, 956-957 (2007).
Goss P.E., Ingle J.N., Martino S., et al. Randomized trial of letrozole following tamoxifen as extended adjuvant therapy in receptor-positive breast cancer: updated findings from NCIC CTG MA.17. *J Natl Cancer Inst.* 97: 1262-1271, (2005).

Gupta, H. B. et al. "Tumor cell-intrinsic PD-L1 promotes tumor-initiating cell generation and functions in melanoma and ovarian cancer," *Signal Transduction and Targeted Therapy* (2016) 1, 16030.
Haffty, B. G. et al. Locoregional relapse and distant metastasis in conservatively managed triple negative early-stage breast cancer. *J Clin Oncol.* 24, 5652-5657 (2006).
Harris H.A. Estrogen receptor-beta: recent lessons from in vivo studies. *Mol Endocrinol.* 21: 1-13, (2007).
Hartman J., Strom A., Gustafssom J.A. Estrogen receptor beta in breast cancer—diagnostic and therapeutic implications. *Steroids.* 74: 635-641, (2009).
Heldring N., Pike A., Anderson S., et al. Estrogen receptors: how do they signal and what are their targets. *Physiol Rev.* 87: 905-931, (2007).
Hodi, F. S. et al. Improved survival with ipilimumab in patients with metastatic melanoma. *N Engl J Med* 363, 711-723, doi:10.1056/NEJMoa1003466 (2010).
Honma N., Hori R., Iwase T. et al: Clinical importance of estrogen receptor-beta evaluation in breast cancer patients treated with adjuvant tamoxifen therapy. *J Clin Oncol.* 26: 3727-3734, (2008).
Huang S, Zhou N, Zhao L, et al. . Pharmacological activation of estrogen receptor beta overcomes tumor resistance to immune checkpoint blockade therapy. *iScience* 2020;23:101458.
Irvin, W. J. J. & Carey, L.A. What is triple-negative breast cancer? *Eur J Cancer.* 44, 2799-2805, (2008).
Jackson R.L., Greiwe J.S., Schwen R.J. Emerging evidence of the health benefits of S-equol, an estrogen receptor beta agonist. *Nutr Rev.* 69: 432-448, (2011a).
Jackson R.L., Greiwe J.S., Schwen R.J. Single-dose and steady-state pharmacokinetic studies of S-equol, a potent nonhormonal, estrogen receptor beta-agonist being developed for the treatment of menopausal symptoms. *Menopause*, 18 185-193, (2011b).
Jenks et al., A pilot study on the effects of S-equol compared to soy isoflavones on menopausal hot flash frequency, *Journal of Women's Health*, 21 (2012) 674-682, (2002).
Jiang P, Gu S, Pan D, et al. . Signatures of T cell dysfunction and exclusion predict cancer immunotherapy response. *Nat Med* 2018;24:1550-8.
Kang, S. P., Martel, M. & Harris, L. N. Triple negative breast cancer: current understanding of biology and treatment options. *Curr Opin Obstet Gynecol.* 20, 40-46, (2008).
Kaplan, H. G. & Malmgren, J. A. Impact of triple negative phenotype on breast cancer prognosis. *Breast Journal* 14, 456-463, (2008).
Katzenellenbogen B., Katzenellenbogen J. Estrogen receptor transcription and transactivation: Estrogen receptor alpha and estrogen receptor beta: regulation by selective estrogen receptor modulators and importance in breast cancer. *Breast Cancer Res.* 2: 335-344, (2000).
Kaufman, H. L. et al. The Society for Immunotherapy of cancer consensus statement on tumour immunotherapy for the treatment of cutaneous melanoma. *Nat Rev Clin Oncol* 10, 588-598,doi: 10.1038/nrclinonc.2013.153 (2013).
Kittaneh et al. "Molecular profiling for breast cancer: A comprehensive review," *Biomark Cancer* 5:61-70, (2013).
Krege, J. H. et al. Generation and reproductive phenotypes of mice lacking estrogen receptor beta. *Proc Natl Acad Sci USA* 95, 15677-15682, (1998).
Leung, Y. K. & Ho, S. M. Estrogen receptor beta: switching to a new partner and escaping from estrogen. *Sci Signal* 4, pe19, doi:10.1126/scisignal.2001991 (2011).
Lin, P. Y. et al. B7—H1-dependent sex-related differences in tumor immunity and immunotherapy responses. *J Immunol* 185, 2747-2753, doi:10.4049/jimmunol.1000496 (2010).
Madak-Erdogan, Z. et al. Integrative genomics of gene and metabolic regulation by estrogen receptors alpha and beta, and their coregulators. *Mol Syst Biol* 9, 676, doi:10.1038/msb.2013.28 (2013).
Mak, P., Leung, Y. K., Tang, W. Y., Harwood, C. & Ho, S. M. Apigenin suppresses cancer cell growth through ERbeta. *Neoplasia* 8, 896-904, doi:10.1593/neo.06538 (2006).
Mak, P. et al. ERbeta impedes prostate cancer EMT by destabilizing HIF-1alpha and inhibiting VEGF-mediated snail nuclear localiza-

(56) References Cited

OTHER PUBLICATIONS tion: implications for Gleason grading. Cancer Cell 17, 319-332, doi:S1535-6108(10)00082-6 [pii] 10.1016/j.ccr.2010.02.030 (2010).

Mao, A., Paharkova-Vatchkova, V., Hardy, J., Miller, M. M. & Kovats, S. Estrogen selectively promotes the differentiation of dendritic cells with characteristics of Langerhans cells. J Immunol 175, 5146-5151 (2005).

Marotti, J. D., Collins, L. C., Hu, R. & Tamimi, R. M. Estrogen receptor-beta expression in invasive breast cancer in relation to molecular phenotype: results from the Nurses' Health Study. Modern Pathology 23, 197-204, doi:10.1038/modpathol.2009.158, (2010).

Marzagalli M., et al. Estrogen Receptor β in Melanoma: From Molecular Insights to Potential Clinical Utility, Frontiers in Endocrinology, vol. 7, Article 140 (2016).

McDonnell D., Norris J.: Connections and regulation of the human estrogen receptor. Science. 296: 1642-1644, (2002).

Mellman, I., Coukos, G. & Dranoff, G. Cancer immunotherapy comes of age. Nature 480, 480-489, doi:10.1038/nature10673 (2011).

Murphy L.C., Watson P.H. Is oestrogen receptor-beta a predictor of endocrine therapy responsiveness in human breast cancer? Endocr Relat Cancer. 13: 327-334, (2006).

Nakajima, Y. et al. Estrogen regulates tumor growth through a nonclassical pathway that includes the transcription factors ERbeta and KLF5. Sci Signal 4, ra22, doi:10.1126/scisignal.2001551 (2011).

Nanda, R. et al. Pembrolizumab in patients with advanced triple-negative breast cancer: Phase 1b Keynote-012 Study. J Clin Oncol 34, 2460-2467, doi:10.1200/JCO.2015.64.8931 (2016).

Nanni, S. et al. Endothelial NOS, estrogen receptor beta, and HIFs cooperate in the activation of a prognostic transcriptional pattern in aggressive human prostate cancer. J Clin Invest 119, 1093-1108, doi:35079 [pii] 10.1172/JCI35079 (2009).

Padrón Á, Hurez V, Gupta HB, Clark CA, Pandeswara SL, Yuan B, Svatek RS, Turk MJ, Drerup JM, Li R, Curiel TJ. "Age effects of distinct immune checkpoint blockade treatments in a mouse melanoma model," Exp Gerontol. May 2018; 105:146-154.

Pan D, Kobayashi A, Jiang P, et al. . A major chromatin regulator determines resistance of tumor cells to T cell-mediated killing. Science 2018;359:770-5.

Pardoll, D. & Drake, C. Immunotherapy earns its spot in the ranks of cancer therapy. J Exp Med 209, 201-209, doi:10.1084/jem.20112275 (2012).

Pardoll, D. M. The blockade of immune checkpoints in cancer immunotherapy. Nat Rev Cancer 12, 252-264, doi: 10.1038/nrc3239 (2012).

Pfefferle, A. D. et al. Transcriptomic classification of genetically engineered mouse models of breast cancer identifies human subtype counterparts. Genome Biol 14, R125, doi:10.1186/GB-2013-14-11-r125 (2013).

Phiel, K. L., Henderson, R. A., Adelman, S. J. & Elloso, M. M. Differential estrogen receptor gene expression in human peripheral blood mononuclear cell populations. Immunol Lett 97, 107-113, doi: 10.1016/j.imlet.2004.10.007 (2005).

Pierdominici, M. et al. Estrogen receptor profiles in human peripheral blood lymphocytes. Immunol Lett 132, 79-85, doi:10.1016/j.imlet.2010.06.003 (2010).

Reese, J.M. et al. ERβ: characterization, prognosis, and evaluation of treatment strategies in ER alpha positive and -negative breast cancer. BMC Cancer 14, 749, doi:10.1186/1471-2407-14-749 (2014).

Reis-Filho, J. S. & Tutt, A. N. J. Triple negative tumours: A critical review. Histopathology 52, 108-118, (2008).

Ribas, A. and Wolchok, J.D. Cancer immunotherapy using checkpoint blockade. Science 359:1350-1355, (2018).

Rugo, H. S. et al. Preliminary efficacy and safety of pembrolizumab (MK-3475) in patients with PD-LI-positive, estrogen receptor-positive (ER+)/HER2-negative advanced breast cancer enrolled in KEYNOTE-028. 2015 San Antonio Breast Cancer Symposium Abstract S5-07 (2015).

Sachs, J.R. et al. Optimal dosing for targeted therapies in oncology: drug development cases leading by example. Clin. Cancer Res. 22(6):OF1-7 (2016).

Sahin, U. and Tureci, O. Personalized vaccines for cancer immunotherapy. Science 359:1355-1356, (2018).

Santen R.J., Brodie H., Simpson E.R., et al. History of aromatase: saga of an important biological mediator and therapeutic target. Endocr Rev. 30: 343-375, (2009).

Sareddy, G. R. et al. Therapeutic significance of estrogen receptor beta agonists in gliomas. Mol Cancer Ther 11, 1174-1182, doi:10.1158/1535-7163.MCT-11-0960 (2012).

Schwen, R.J., Greiwe, J. S., Schwen, R. J. Elucidation of the metabolic pathway of s-equol in rat, monkey and man. Food Chemistry Toxicology. 50: 2074-2083, (2012).

Setchell, K.D., Clerici C., Lephart E.D., et al. S-equol, a potent ligand for estrogen receptor beta, is the exclusive enantiomeric form of the soy isoflavone metabolite produced by human intestinal bacterial flora. Am J Clini Nutr. 81: 1072-1079, (2005).

Setchell, K.D. The clinical inportance of the metabolite equol—a clue to the effectiveness of soy and its isoflavones. Nature. 132:3577-3584, (2002).

Shaaban A.M., Green A.R., Karthik S. Nuclear and cytoplasmic expression of ERbeta1, ERbeta2, and ERbeta5 identifies distinct prognostic outcome for breast cancer patients. Clin Cancer Res. 14: 5228-5235, (2008).

Sharma, P. & Allison, J. P. Immune checkpoint targeting in cancer therapy: toward combination strategies with curative potential. Cell 161, 205-214, doi:10.1016/j.cell.2015.03.030 (2015).

Shou J., Massarweh S., Osborne C.K., et al. Mechanisms of tamoxifen resistance: increased estrogen receptor-HER2/neu crosstalk in ER/HER2-positive breast cancer. J Natl Cancer Inst. 96: 926-935, 2004.

Smith I.E., Dowsett M., Ebbs S., et al. Neoadjuvant treatment of postmenopausal breast cancer with anastrozole, tamoxifen, or both in combination: The immediate preoperative anastrozole, tamoxifen, or combined with tamoxifen (IMPACT) multicenter double-blind randomized trial. J Clini Onc. 23: 5108-5116, (2005).

Smith C.L., O'Malley B.W. Coregulator Function: A Key to Understanding Tissue Specificity of Selective Receptor Modulators. Endocrine Reviews 25(1):45-71, (2004).

Steinberg SM, Shabaneh TB, Zhang P, Martyanov V, Li Z, Malik BT, Wood TA, Boni A, Molodtsov A, Angeles CV, Curiel TJ, Whitfield ML, Turk MJ. "Myeloid Cells That Impair Immunotherapy Are Restored in Melanomas with Acquired Resistance to BRAF Inhibitors," Cancer Res. Apr. 1, 2017;77(7):1599-1610.

Svoronos, N. et al. Tumor Cell-Independent Estrogen Signaling Drives Disease Progression through Mobilization of Myeloid-Derived Supressor Cells. Cancer Discov, doi:10.1158/2159-8290.CD-16-0502 (2016).

Thomas C., Gustafsson J.A. The different roles of ER subtypes in cancer biology and therapy. Nat Rev Cancer. 11: 597-608, (2011).

Topalian, S. L., Drake, C. G. & Pardoll, D. M. Immune checkpoint blockade: a common denominator approach to cancer therapy. Cancer Cel 27, 450-461, doi:10.1016/j.ccell.2015.03.001 (2015).

Topalian, S. L. et al. Survival, durable tumor remission, and long-term safety in patients with advanced melanoma receiving nivolumab. J Clin Oncol 32, 1020-1030, doi:10.1200/JCO.2013.53.0105 (2014).

Topalian, S. L., Drake, C. G. & Pardall, D. M. Targeting the PD-1/B7-H1(PD-L1) pathway to activate anti-tumor immunity. Curr Opin Immunol 24, 207-212, doi:10.1016/j.coi.2011.12.009 (2012).

Urruticoechea A., Smith I., Dowsett M. Proliferation marker Ki-67 in early breast cancer. Journal of Clinical Oncology 23:7212-7220, (2005).

Usui et al., Effects of natural S-equol supplements on overweight or obesity and metabolic syndrome in the Japanese, based on sex and equol status, Clinical endocrinology, 78 365- 372, (2013).

Wang L, Fan J, Thompson LF, et al. . Cd73 has distinct roles in nonhematopoietic and hematopoietic cells to promote tumor growth in mice. J Clin Invest 2011;121:2371-82.

Wherry, E. J. & Kurachi, M. Molecular and cellular insights into T cell exhaustion. Nat Rev Immunol 15, 486-499, doi:10.1038/nri3862 (2015).

(56) References Cited

OTHER PUBLICATIONS

Wolchok, J. D. et al. Nivolumab plus ipilimumab in advanced melanoma. *N Engl J Med 369*, 122-133, doi:10.1056/NEJMoa1302369 (2013).

Yakimchuk, K., Jondal, M. & Okret, S. Estrogen receptor alpha and beta in the normal immune system and in lymphoid malignancies. Mol Cell Endocrinol 375, 121-129, doi:10.1016/j.mce.2013.05.016 (2013).

Yao et al., Potentiation of brain mitochondrial function by S-equol and R/S-equol estrogen receptor beta-selective phytoSERM treatments, *Brain Research*, 1514 128-141, (2013).

Yuan, B. et al. A phosphotyrosine switch determines the antitumor activity of ERbeta. *J Clin Invest 124*, 3378-3390, doi:10.1172/JCI74085 (2014).

Yuan B., Cheng L., Chiang H.C., et al. Mobilizing ERβ antitumor activity through a phosphotyrosine switch. *J Clini Invest.* 124(8):3378-90, (2014).

Yuan, B. et al. Tyrosine phosphorylation regulates ERbeta ubiquitination, protein turnover, and inhibition of breast cancer. *Oncotarget*, doi: 10.18632/oncotarget.10018 (2016).

Zhao et al., A select combination of clinically relevant phytoestrogens enhances estrogen receptor β-binding selectivity and neuroprotective activities in vitro and in vivo. *Neuroendocrinology*, 150(2):770-783, (2009).

Zhao L, Huang S, Mei S, et al. . Pharmacological activation of estrogen receptor beta augments innate immunity to suppress cancer metastasis. *Proc Natl Acad Sci U S A* 2018;115:E3673-81.

Zipfel PA, Zhang W, Quiroz M, et al. . Requirement for Abl kinases in T cell receptor signaling. *Curr Biol* 2004;14:1222-31./.

* cited by examiner

A

| TNBC: Results: Ki67 | |
|---|---|
| >20% Reduction | 0-20% Reduction |
| 34.2% | 8.3% |
| 60.0% | 9.1% |
| 38.6% | 7.6% |
| 41.2% | 6.7% |
| 22.3% | 3.7% |
|  | 14.7% |
|  | 2.9% |
| 5 patients had no reduction in Ki-67 | |

SEQUENCE LISTING

```
<160> NUMBER OF SEQ ID NOS: 3

<210> SEQ ID NO 1
<211> LENGTH: 30
<212> TYPE: DNA
<213> ORGANISM: Mus musculus

<400> SEQUENCE: 1
ctatatccct tcctcctatg tagagagccg                                    30

<210> SEQ ID NO 2
<211> LENGTH: 30
<212> TYPE: DNA
<213> ORGANISM: Mus musculus

<400> SEQUENCE: 2
ctatatccct tcctcctttg tagagagccg                                    30
```

```
<210> SEQ ID NO 3
<211> LENGTH: 14
<212> TYPE: DNA
<213> ORGANISM: Mus musculus

<400> SEQUENCE: 3
ctttgtagag agcc                                                       14
```

MODULATION OF MOLECULAR MARKERS USING S-EQUOL

CROSS-REFERENCE TO RELATED APPLICATIONS

This application claims priority from U.S. Provisional Application Ser. No. 63/117,888, filed Nov. 24, 2020. That provisional application, as well as U.S. Provisional Application Ser. No. 62/685,392, filed Jun. 15, 2018 and 62/728,981, filed Sep. 10, 2018, and U.S. application Ser. Nos. 16/384,417 and 16/384,428, both filed Apr. 15, 2019, are hereby incorporated by reference in their entireties for all purposes.

The instant application contains a Sequence Listing which has been submitted electronically via EFS-Web in ASCII format and is hereby incorporated by reference in its entirety. Said ASCII copy, created on Jan. 11, 2022, is named 3601-109.US2_ST25 and is 814 bytes in size.

STATEMENT OF GOVERNMENTAL SUPPORT

This invention was made with U.S. Government support under grant number CA205965, CA206529, CA212674 and CA231325, awarded by the National Institutes of Health, and the Texas Cancer Research Grant Contract under grant number DP150055 by the Cancer Prevention and Research Institute of Texas. The work was also supported by grant W81XWH-17-1-0007 awarded by the Department of Defense, and by an CPRIT Postdoctoral Training Grant (RP170345). The U.S. Government and the Texas State Government have certain rights in this invention.

BACKGROUND OF THE INVENTION

Field of the Invention

This invention relates to methods and compositions for modulating molecular markers, and hence treating or preventing breast cancer (e.g., triple-negative breast cancer) and melanoma with a pharmaceutically effective amount of S-equol or a pharmaceutical composition comprising S-equol. The method may facilitate T-cell receptor (TCR) activation, stimulate an ERβ switch and boost immunotherapy. In a preferred embodiment, the method relates to a combination therapy using S-equol and another anti-cancer treatment, such as immunotherapy.

Description of the Related Art

The methods and compositions of the present invention are suitable for various types of cancers, particularly those responsive to targeting of the estrogen receptor beta (ERβ). In addition to being suitable for treating breast cancer (see, U.S. Provisional Application 62/685,392, filed Jun. 15, 2018), the methods and compositions of the present invention are suitable for treating melanoma (see, U.S. Provisional Application Ser. No. 62/728,981, filed Sep. 10, 2018.)

Breast cancer is highly heterogeneous and consists of multiple subtypes. Triple negative breast cancer (TNBC) is a subtype of breast cancer that lacks the expression of estrogen receptor α (ERα), progesterone receptor (PR), and human epidermal growth factor receptor 2 (HER2). (Cleator et al. (2007); Kang et al. (2008); Chia and Tutt (2007); Diaz et al. (2007); Gonzalez-Angulo (2007); Reis-Filho and Tutt (2008); Irvin and Carey (2008)). While TNBC constitutes approximately 15% of all breast cancers, mortality of patients with TNBC is disproportionately higher than those with other subtypes of breast cancer. TNBC tends to have more rapid disease progression (Gerson et al. (2008); Dent et al. (2007); Haffty et al. (2006); Kaplan and Malmgren (2008)), yet the "triple negative" characteristic excludes TNBC patients from the benefit of standard hormonal and HER2-targeted therapies (Baum et al. (2002); Davies et al. (2013); Goss et al. (2005); Santen et al. (2009); Shou et al. (2004); Smith et al. (2005)). Despite several prospects on the therapeutic horizon for TNBC, chemotherapy remains the only standard treatment for TNBC patients. Those who are resistant to current chemotherapies suffer from unnecessary toxicity without substantial clinical benefits. Therefore, there is an urgent need to develop safer and more effective treatment for TNBC.

Malignant melanoma is a potentially serious skin cancer that results from the uncontrolled growth of pigment cells, called melanocytes. Melanoma may be the result of UV-induced changes to the skin, and its occurrence may be increased as a result of various genetic mutations. Mutations arising in the c-Kit gene, the BRAF gene, the CDKN2A gene, which regulates cell division, the MDm2 gene, which is a negative regulator of the p53 tumor suppressor gene, the retinoblastoma RB1 gene, and the MC1R (melanocortin-1 receptor) gene are among those that may increase the risk of developing melanoma. Treatment of melanoma may include the use of surgery, chemotherapy and/or immunotherapy. (Gupta et al., 2016; Clark et al., 2016; Steinberg et al., 2017).

Recent years have witnessed major clinical breakthroughs in cancer immunotherapies (Mellman et al. (2011); Kaufman et al. (2013); Brower (2015); Topalian et al. (2015)), which include blocking the immune-suppressive immune checkpoint molecules CTLA-4 (cytotoxic T-lymphocyte-associated protein 4 or CD152 [cluster of differentiation 152]), PD-1 (programmed cell death protein 1), and PD-L1 (programmed death ligand 1; Hodi et al. (2010); Wolchok et al. (2013); Topalian et al. (2014)). PD-1 is a checkpoint protein on T-cells that serves as an "off switch" to keep T cells from attacking other cells in the body. PD-1 interacts with PD-L1 on tumor cells. When PD-L1 interacts with PD-1, it prevents the T-cells from attacking the tumor cells. PD-1 inhibitors are currently being used to treat melanoma and other cancers.

A review of cancer immunotherapy using checkpoint blockade has been published as in Ribas and Wolchok, (2018) (see reference list herein), and is incorporated by reference herein in its entirety, particularly for the purposes of discussing pathways to be targeted with immunotherapy and antibodies for use in that checkpoint blockade. In addition, methods of rationally selecting cancer vaccine targets based on a patient's "mutanome," namely, a set of somatic mutations that generate cancer-specific neoepitopes which can be recognized by autologous T cells as foreign, are discussed in Sahin and Tureci, (2018) (see reference list herein). This publication is also incorporated by reference herein in its entirety for discussing personalized targeting of tumor antigens such that cells of the immune system (e.g., CD4[+] T helper cells and CD8+T cytotoxic cells) can be activated to attack tumor cells. See, FIGS. 1 and 2. Both of these types of cancer immunotherapy can be combined with the use of S-equol in accordance with the present invention.

CD4+ T cells play a key role in the functioning of a healthy immune system. They assist B cells to make antibodies, activate the microbe killing capacity of macrophages and recruit other immune cells to infected or inflamed areas of the body. These activities are orchestrated through their production of various cytokines and chemokines. It has been known for some time that uncommitted CD4+ T-cells can differentiate into Th1 or Th2 cells, based on the prevailing pro-inflammatory/anti-inflammatory environment, and that these activated Th1 and Th2 cells had distinct cytokine production patterns and functions. Generally, Th1 cells were associated with the eradication of intracellular pathogens whereas Th2 cells were heavily involved in responses against extracellular pathogens and parasites. Uncontrolled Th1 responses were implicated in autoimmunity and aberrant Th2 responses were associated with allergy and asthma development. However, this model did not explain the observation that a deficiency in Th1 signaling and/or cytokines still allowed the development of autoimmune diseases such as rheumatoid arthritis and multiple sclerosis. More recently (2006) a third subset of CD4 T cells, Th17 cells, which have a pro-inflammatory bias was identified. Subsequent research using animal models and human studies has demonstrated a key role for Th17 cells in the immune system's defense against extracellular bacteria and fungi as well as the development of autoimmune diseases, mediated by the secretion of IL-17 by these cells. The secretion of IL-23 from antigen-presenting cells such as dendritic cells, which have been activated by the uptake and processing of pathogens, in turn activates Th17 cells. (Taken from Bitesized Immunology: https://www.immunology.org/public-information/bitesized-immunology/cells/th17-cells.) See, FIG. 2.

CD8$^+$ (cytotoxic) T cells, like CD4$^+$ Helper T cells, are generated in the thymus and express the T cell receptor. However, rather than the CD4 molecule, cytotoxic T cells express a dimeric coreceptor, CD8, usually composed of one CD8α and one CD8β chain. CD8$^+$ T cells recognize peptides presented by MHC Class I molecules, found on all nucleated cells. The CD8 heterodimer binds to a conserved portion (the α3 region) of MHC Class I during T cell/antigen presenting cell interactions (see FIG. 1). CD8+ T cells (often called cytotoxic T lymphocytes, or CTLs) are very important for immune defense against intracellular pathogens, including viruses and bacteria, and for tumor surveillance. When a CD8$^+$ T cell recognizes its antigen and becomes activated, it has three major mechanisms to kill infected or malignant cells. The first is secretion of cytokines, primarily TNF-α and IFN-γ, which have anti-tumor and anti-microbial effects. The second major function is the production and release of cytotoxic granules. These granules, also found in natural killer (NK) cells, contain two families of proteins, perforin, and granzymes. Perforin forms a pore in the membrane of the target cell, similar to the membrane attack complex of complement. This pore allows the granzymes also contained in the cytotoxic granules to enter the infected or malignant cell. Granzymes are serine proteases which cleave the proteins inside the cell, shutting down the production of viral proteins and ultimately resulting in apoptosis of the target cell. The cytotoxic granules are released only in the direction of the target cell, aligned along the immune synapse, to avoid non-specific bystander damage to healthy surrounding tissue (see FIG. 1). CD8$^+$ T cells are able to release their granules, kill an infected cell, then move to a new target and kill again, often referred to as serial killing. The third major function of CD8$^+$ T cell destruction of infected cells is via Fas/FasL interactions. Activated CD8$^+$ T cells express FasL on the cell surface, which binds to its receptor, Fas, on the surface of the target cell. This binding causes the Fas molecules on the surface of the target cell to trimerize, which pulls together signaling molecules. These signaling molecules result in the activation of the caspase cascade, which also results in apoptosis of the target cell. Because CD8$^+$ T cells can express both molecules, Fas/FasL interactions are a mechanism by which CD8$^+$ T cells can kill each other, called fratricide, to eliminate immune effector cells during the contraction phase at the end of an immune response. In addition to their critical role in immune defense against viruses, intracellular bacteria, and tumors, CD8$^+$ T cells can also contribute to an excessive immune response that leads to immunopathology, or immune-mediated damage. (Taken from Bitesized Immunology: https://www.immunology.org/public-information/bitesized-immunology/cells/cd8-t-cells.)

With respect to NK cells, the PK136 monoclonal antibody reacts with mouse NK1.1, an antigen expressed by natural killer cells and a subset of T cells in the NK1.1 mouse strains including C57BL and NZB. Several commonly used laboratory mouse strains such as BALB/c, SJL, AKR, CBA, C3H and A do not express the NK1.1 antigen. For detection of NK cells in these strains the monoclonal antibody DXS 14-5971 is used. Simultaneous staining of C57BL/6 spleen cells with PK136 and DXS reveals coexpression of both markers by a majority of cells as well as presence of small populations of DXS+PK136- and DXS-PK136+ cells.

CD45 (lymphocyte common antigen) and its associated molecules have also been shown to be important for T cell activation. CD45 is a receptor-linked protein tyrosine phosphatase that is expressed on all leucocytes, and which plays a crucial role in the function of these cells. On T cells the extracellular domain of CD45 is expressed in several different isoforms, and the particular isoform(s) expressed depends on the particular subpopulation of cell, their state of maturation, and whether or not they have previously been exposed to antigen. It has been established that the expression of CD45 is essential for the activation of T cells via the TCR, and that different CD45 isoforms display a different ability to support T cell activation. Although the tyrosine phosphatase activity of the intracellular region of CD45 has been shown to be crucial for supporting signal transduction from the TCR, the nature of the ligands for the different isoforms of CD45 have been elusive. Moreover, the precise mechanism by which potential ligands may regulate CD45 function is unclear. Interestingly, in T cells CD45 has been shown to associate with numerous molecules, both membrane associated and intracellular; these include components of the TCR-CD3 complex and CD4/CD8. In addition, CD45 is reported to associate with several intracellular protein tyrosine kinases including R561ck and p59fyn of the src family, and ZAP-70 of the Syk family, and with numerous proteins of 29-34 kDa. These CD45-associated molecules may play an important role in regulating CD45 tyrosine phosphatase activity and function. However, although the role of some of the CD45-associated molecules (e.g. CD45-AP and LPAP) has become better understood in recent years, the role of others still remains obscure. See, Altin and Sloan, (1997) in the reference list herein.

However, these highly promising immunotherapies are only effective for a subset of cancer patients and are not usually curative. In particular, clinical trials of anti-PD-1 antibodies in triple negative breast cancer (TNBC) patients demonstrate only modest efficacy, with objective responses in the range of 10-20%, and an additional 20% of patients experiencing some stabilization of disease that would otherwise be rapidly progressive (Nanda et al. (2016); Emens et al. (2015); Dirix et al. (2015); Rugo et al. (2015); Dawood and Rugo (2016)). There is thus a pressing clinical need to identify better therapies to improve individual responses to immunotherapy for the treatment of TNBC, melanoma, and other cancers.

PD-1 and its ligand PD-L1 are immune checkpoint molecules that dampen T cell immunity (Lin et al. (2010); Curiel et al. (2003); Brahmer et al. (2012); Pardoll and Drake (2012); Pardoll (2012)). PD-L1 is overexpressed in tumor cells and some immune cells, including Tregs (Lin et al. (2010); Curiel et al. (2003); Pardoll (2012); Topalian et al. 2012)). Immunotherapy with anti-PD-1 (αPD-1) and anti-PD-LI antibodies (αPD-L1) has proven successful for treating various cancers (Brahmer (2012); Pardoll and Drake (2012); Pardoll (2012)). Early clinical trials for TNBC indicate that PD-1 and PD-L1 are valid targets for intervention and toxicities of treatment are mild. In a Phase 1 study of 27 women with heavily pretreated, chemotherapy resistant, metastatic TNBC that expressed PD-L1, the response rate was 18.4% to pembrolizumab, an αPD-1 antibody (Nanda et al. 2016). A similar study of atezolizumab, an αPD-LI antibody, produced a response rate of 19% in 21 evaluable, PD-L1 expressing TNBC tumors (Emens et al. (2015); Dawood and Rugo (2016)). Another group reported an 8.6% response rate to avelumab, another αPD-LI antibody, in 168 TNBC tumors unselected for PD-L1 expression (Dirix et al. 2015), indicating that level of PD-L 1 tumor expression may be important in mediating tumor response. Some disease stabilization was seen in this aggressive subtype of breast cancer, in approximately 20% of patients in these 3 trials. Serious toxicities were few and related to immune modulation. These clinical data indicate that the PD-1/PD-L1 axis can be a therapeutic target, likely in combination approaches for better efficacy.

There are two distinct types of estrogen receptors that mediate diverse physiological effects of estrogens on breast cancer cells. The first receptor is the ERα receptor which supports estrogen-dependent breast tumor growth. The second is the ERβ receptor which appears to work in an opposite fashion to significantly attenuate the growth of breast tumor cells in preclinical models (Clarke et al. (2003); Deroo and Korach (2006); Deroo and Buensuceso (2010); Honma et al (2008); Katzenellenbogen and Katzenellenbogen (2000); McDonnell and Norris (2002); Murphy and Watson (2006); Shaaban et al (2008). Thus, ERβ can be viewed in as a tumor suppressor gene in breast cancer. ERβ is expressed in about 40% of TNBC cancers, and the therapeutic potentials of targeting ERβ have not yet been investigated in TNBC. Two recent advances have now made it feasible to move from the preclinical models and into clinical research. The first advance is a newly discovered mechanism of rallying ERβ's antitumor activity (Harris (2007); Hartman et al (2009); Heldring et al. (2007); Thomas and Gustafsson (2011)), and the second is the development of an oral formulation of an ERβ agonist (S-equol) that has already been tested for clinical safety, pharmacodynamics and tolerance in humans (Jackson et al. (2011a & b); Setchell et al. (20005); Setchell (2002); Schwen et al. (2012).

Estrogen receptor (ERβ; nuclear or cytoplasmic) is reported to be present in approximately half of TNBC (Marotti et al. (2010); Reese et al. (2014)) as well as in melanoma (Marzagalli et al., 2016). In addition to its tumor-intrinsic activity, ERβ in host cells has also been implicated in melanoma tumor inhibition (Cho et al. (2010)). In support of a tumor-extrinsic antitumor activity of ER☐, Cho et al. showed that syngeneic murine melanoma cells grafted to recipient ERβ-KO animals grew more robustly than those in WT recipient. In this study, the authors showed that the growth of 3 different skin cancer cell lines in their syngeneic murine hosts was sensitive to the activity of the estrogen receptor. Therefore these transplantation studies, used as models of skin cancer induction by SSUV irradiation, strongly suggest that signaling by the ERβ is an endogenous protective mechanism to inhibit skin cancer growth that is partially mediated immunologically. The recognition of selective ER modulators (SERMs) as agents able to elicit estrogenic effects in a tissue-specific manner has expanded the potential population that could benefit from ER ligand therapies. (Smith and O'Malley, 2018).

Thus, rallying ERβ antitumor activity through ERβ-specific modification and/or ligand binding represents an excellent therapeutic opportunity for TNBC and melanoma. However, the therapeutic potentials of targeting ERβ have not been extensively exploited, partly due to the paucity in the knowledge of how to harness its antitumor activity. A phosphotyrosine residue (Y36) in ERβ, but not ERα, has recently been identified that is important for regulating the antitumor activity of ERβ in TNBC cells (Yuan et al. (2014); Yuan et al. (2016)).

When this phosphotyrosine residue (pY36) was purposefully mutated by adding a phenylalanine group (Y36F), activation of ERβ target genes were decreased in a TNBC cell line (MDA-MB-231). The Y36F mutation also obliterated the ability of ERβ to inhibit tumor cell growth in vitro and in vivo. This preclinical research therefore strongly supports the importance of pY36 in the antitumor activity of ERβ (Yuan et al., 2014).

There is also evidence that pY36 status correlates with survival of breast cancer patients. Research has been done using a Prognostic Tissue Microarray (TMA) from the National Cancer Institute (NCI), which consists of a large cohort of breast tumor samples with a clinical follow-up record. Using a total of 726 readable IHC samples, patients with pY36-negative tumors were found to have statistically significant shorter disease-free and overall survival than those with pY36-positive tumors. Interestingly, the association with survival was only seen in Stage II & III disease, which raises the intriguing possibility that pY36 activity may have an effect on disease progression from locally advanced to metastatic breast cancer. Collectively, pY36 intensity appears to have a stronger correlation with patient outcome than total ERβ, underscoring the clinical importance of this previously unappreciated phosphotyrosine switch. See, FIG. 3.

S-equol, an ERβ agonist, was previously shown to increase respiratory and maximal glycolysis fluxes in rat hippocampal neurons, as well as cytochrome oxidase (COX) activity and COX1 protein levels in brains from ovariectomized mice, and has been studied in human subjects to assess its health impact and safety (Yao et al. (2013); Jenks et al. (2002); Jackson et al. (2011a & b); Usui et al., (2013)).

S-equol can be produced either chemically (i.e., chemical synthesis) or by biotransformation (biosynthesis) through the metabolism of daidzein, an isoflavone found in soy and red clover, by gut bacteria. The structure of S-equol is shown below.

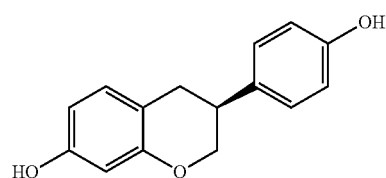 [SMILES: Oc1ccc([C@H]2COc3cc(O)ccc3C2)cc1]

Equol has a chiral center and therefore can exist in two enantiomeric forms. S-equol, R-equol, racemic equol, and non-racemic mixtures of equol (collectively "equol"); compositions of equol; anhydrous crystalline polymorph of equol; processes for the preparation of equol; and methods of using equol are described in U.S. Pat. No. 8,716,497 (filed Sep. 10, 2012); U.S. Pat. No. 8,048,913 (filed Sep. 14, 2009); U.S. Pat. No. 7,960,432 (filed Jul. 3, 2008); U.S. Pat. No. 7,396,855 (filed Jul. 24, 2003); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005); U.S. Pat. No. 8,668,914 (filed Jul. 31, 2009); U.S. Pat. No. 8,580,846 (filed Aug. 18, 2006); U.S. Pat. No. 8,450,364 (filed Apr. 9, 2012); and U.S. Pat. No. 8,153,684 (filed Oct. 2, 2009); U.S. Pat. No. 9,408,824 (filed Mar. 5, 2014); and U.S. Pat. No. 9,914,718 (filed Oct. 14, 2015); each of which is hereby incorporated by reference in its entirety.

Formulations comprising isoflavones and products derived therefrom have been used in the past to treat disease. For example, a mixture of equol, genistein, and daidzein, or a mixture of equol, genistein, daidzein, and IBSO03569 have shown potential for treating or preventing neurodegeneration and Alzheimer's disease. See Zhao et al. (2009); U.S. Pat. No. 8,552,057; Yao et al. (2013) (collectively "Brinton et al."). S-equol alone has also been described for treating Alzheimer's Disease. See, U.S. application Ser. No. 15/659,114 published as U.S. Patent Publication 2018/0028491, and International Patent Publication WO/2018/022604, which are hereby incorporated by reference in their entireties.

However, there remains a need in the art for methods that utilize S-equol for the treatment of other disease states that have in the past been difficult to treat. In particular, there is a need in the art for methods that utilize S-equol in the treatment of melanoma.

SUMMARY OF THE INVENTION

The following brief summary is not intended to include all features and aspects of the present invention, nor does it imply that the invention must include all features and aspects discussed in this summary.

The inventors have found that S-equol, preferably pure and isolated S-equol, benefit melanoma patients. In particular, the inventors have found that S-equol in combination with immunotherapy is particularly effective in treating breast cancer and melanoma.

It is therefore an object of the invention to provide the following:

1. A method for treating or preventing cancer, comprising administering a pharmaceutically effective amount of a formulation comprising S-equol to a subject in need thereof.
2. The method of Item 1, wherein the formulation comprises 10-200 mg S-equol.
3. The method of Item 1, wherein the formulation comprises 50-150 mg S-equol.
4. The method of Item 1, wherein the formulation comprises about 50 mg S-equol.
5. The method of Item 1, wherein the formulation comprises about 150 mg S-equol.
6. The method of Item 1, wherein the formulation is administered orally, intravenously, intraperitoneally, or subcutaneously.
7. The method of Item 1, wherein said subject is a human.
8. The method of Item 1, wherein the S-equol is administered in combination with one or more other cancer treatments.
9. The method of Item 8, wherein the S-equol is administered in combination with an immunotherapeutic agent.
10. The method of Item 9, wherein the immunotherapeutic agent is an antibody.
11. The method of Item 10, wherein the antibody is directed to programmed cell death protein 1 (PD-1).
12. The method of Item 11, wherein the antibody is directed to programmed death ligand 1 (PDL-1).
13. The method of Item 11, wherein the antibody is pembrolizumab.
14. The method of Item 12, wherein the antibody is atezolizumab.
15. The method of Item 12, wherein the antibody is avelumab.
16. The method of Item 1, wherein the formulation is essentially free of genistein, daidzein, and/or IBSO03569.
17. The method of Item 1, wherein genistein, daidzein, and/or IBSO03569 are not co-administered with S-equol.
18. The method of Item 1, wherein the formulation is essentially free of R-equol.
19. The method of Item 1, wherein the S-equol is produced chemically.
20. The method of Item 1, wherein the formulation is administered once per day.
21. The method of Item 1, wherein the formulation is administered twice per day.
22. The method of Item 1, wherein the formulation is administered three times per day.
23. The method of Item 1, wherein the formulation is administered four times per day.
24. The method of Item 1, wherein the cancer is breast cancer.
25. The method of Item 24, wherein the breast cancer is triple negative breast cancer.
26. The method of Item 1, wherein the cancer is melanoma.
27. A composition for treating cancer, comprising 10-200 mg S-equol.
28. The composition of Item 27, wherein the composition comprises 50-150 mg S-equol.
29. The composition of Item 28, wherein the composition comprises about 50 mg S-equol.
30. The composition of Item 28, wherein the composition comprises about 150 mg S-equol.
31. The composition of Item 27, wherein the composition is formulated to be administered orally, intravenously, intraperitoneally, or subcutaneously.
32. The composition of Item 27, further comprising one or more other cancer treatments.
33. The composition of Item 32, wherein the one or more other cancer treatments are immunotherapeutic agents.
34. The composition of Item 33, wherein the immunotherapeutic agent is an antibody.
35. The composition of Item 34, wherein the antibody is directed to programmed cell death protein 1 (PD-1).
36. The composition of Item 34, wherein the antibody is directed to programmed death ligand 1 (PDL-1).
37. The composition of Item 35, wherein the antibody is pembrolizumab.
38. The composition of Item 36, wherein the antibody is atezolizumab.
39. The composition of Item 36, wherein the antibody is avelumab.

40. The method of Item 1, wherein the composition is essentially free of genistein, daidzein, and/or IBSO03569.

41. The composition of Item 27, wherein genistein, daidzein, and/or IBSO03569 are not co-administered with S-equol.

42. The composition of Item 27, wherein the composition is essentially free of R-equol.

43. The composition of Item 27, wherein the S-equol is produced chemically.

44. A method for activating T-cell receptor activation, comprising administering a pharmaceutically effective amount of a composition of any one of Items 27-43.

45. The method of Item 44, wherein the T-cell receptor activation stimulates an ERβ phosphotyrosine switch.

46. The method of Item 44, wherein the T-cell receptor activation boosts immunotherapy.

47. The method of Item 46, wherein the immunotherapy is anti-PD-1 immune checkpoint blockade (ICB).

1.

The invention also relates to compositions comprising S-equol as described for the methods herein.

The foregoing and other objects, features and advantages of the invention will be apparent from the following more particular description of preferred embodiments of the invention, as illustrated in the accompanying drawings in which like reference characters refer to the same parts throughout the different views.

BRIEF DESCRIPTION OF THE DRAWINGS

The application file contains at least one drawing executed in color. Copies of any patent or patent application publication from this application containing color drawing(s) will be provided by the Office upon request and payment of the necessary fee.

FIG. 3A shows the Kaplan-Meier estimate of disease-free and overall survival in Stages II-III specimens correlating with IHC intensity of pY36-ERβ.
FIG. 3B shows the Kaplan-Meier estimate of disease-free and overall survival in Stages II-III specimens correlating with IHC intensity of (A) and total ERβ IHC.
FIG. 5A shows the schema for the chimera experiments.
FIG. 5B shows tumor growth in chimeric mice (WT>WT: n=10, KI>WT: n=4). p=0.0003.
FIG. 5C shows total CD8+ T cells from tumors.
FIG. 5D shows interferon gamma (IFN-γ) expressing CD8$^+$ T cells from tumors.
FIG. 6 shows that separately, S-equol and anti-PD-1 antibody reduce tumor volume compared to control, but S-equol in combination with an anti-PD-1 antibody reduces tumor volume compared to S-equol or anti-PD-1 antibody alone over 12 days post-challenge.

FIG. 7 shows that separately, S-equol and anti-PD-1 antibody reduce tumor volume compared to control, but S-equol in combination with an anti-PD-1 antibody reduces tumor volume compared to S-equol or anti-PD-1 antibody alone over 19 days post-challenge.

FIG. 8A shows that separately, S-equol and anti-PD-1 antibody reduce tumor weight compared to control, but S-equol in combination with an anti-PD-1 antibody reduces tumor weight compared to S-equol or anti-PD-1 antibody alone. FIG. 8B shows mouse total body weight for each treatment.

FIG. 9A shows that separately, S-equol and anti-PD-1 antibody reduce tumor volume compared to control, but S-equol in combination with an anti-PD-1 antibody reduces tumor volume compared to S-equol or anti-PD-1 antibody alone over 12 days post-challenge. FIG. 9B shows results with LY500307, a selective ERβ agonist (SERBA-1; Erteberel®).

FIG. 11A shows an immunoblot of mouse ERβ in tissues from WT, KO, and KI animals. Ponceau S staining for protein loading. FIG. 11B shows WT and KI female mice (n=8) were orthotopically injected with syngeneic murine mammary tumor cells (M-Wnt1, 1×10$^4$). *p<0.05.

FIG. 12A shows that separately, S-equol and anti-PD-1 antibody reduce tumor volume compared to control, but S-equol in combination with an anti-PD-1 antibody reduces tumor volume compared to S-equol or anti-PD-1 antibody alone over 35 days post-challenge. FIG. 12B shows that separately, S-equol and anti-PD-1 antibody reduce tumor weight compared to control, but S-equol in combination with an anti-PD-1 antibody reduces tumor weight compared to S-equol or anti-PD-1 antibody alone. FIG. 12C shows tumors from mice treated with vehicle+IgG2a, S-equol+IgG2a, vehicle+anti-PD-1 antibody and S-equol+anti-PD-1 antibody and that separately, S-equol and anti-PD-1 antibody reduce tumor size compared to control, but S-equol in combination with an anti-PD-1 antibody reduces tumor size compared to S-equol or anti-PD-1 antibody alone.

FIG. 13A shows that the percentage of CD45$^+$CD3$^+$ cells increased in mice treated with S-equol plus an anti-PD-1 antibody compared to mice treated with S-equol or anti-PD-1 antibody alone. FIG. 13B shows CD4$^+$ cells decreased in mice treated with S-equol plus an anti-PD-1 antibody compared to mice treated with S-equol or anti-PD-1 antibody alone. FIG. 13C shows CD8+ cells increased in mice treated with S-equol plus an anti-PD-1 antibody compared to mice treated with S-equol or anti-PD-1 antibody alone. FIG. 13D shows NK1.1+ cells increased in mice treated with S-equol plus an anti-PD-1 antibody compared to mice treated with S-equol or anti-PD-1 antibody alone.

FIG. 14 shows that S-equol plus an anti-PD-1 antibody reduces tumor volume compared to S-equol or anti-PD-1 antibody alone over 28 days post-challenge.

FIG. 15A shows tumors from mice treated with vehicle+IgG2a, S-equol+IgG2a, vehicle+anti-PD-1 antibody and S-equol+anti-PD-1 antibody. FIG. 7B shows that S-equol plus an anti-PD-1 antibody reduces tumor weight compared to S-equol or anti-PD-1 antibody alone.

FIG. 16A shows that a pY36-specific phosphorylation signal was enhanced by the ERα/ERβ common agonist 17-β-estradiol and two ERβ-specific agonists diarylpropionitrile (DPN) and S-equol in MDA-MB-231 cells. FIG. 16B shows that S-equol treatment inhibited MDA-MB-231 cell-derived xenograft tumor growth (n=5). FIG. 16C shows expression of Ki67 in xenograft tumors. FIG. 16D shows ERβ-pY36 signal in vehicle- and S-equol-treated xenograft tumor samples. *p,0.05, **p<0.01. See, Yuan et al. (2016) listed below, which is incorporated by reference herein for all purposes.

FIG. 19A shows the Kaplan-Meier estimate of disease-free and overall survival in Stages II-III specimens correlating with IHC intensity of pY36-ERβ. FIG. 19B shows the Kaplan-Meier estimate of disease-free and overall survival in Stages II-III specimens correlating with IHC intensity of (A) and total ERβ IHC.

FIG. 20A shows Ki-67 positivity in tumors of control and S-equol treated mice. FIG. 20B shows images of Ki-67 immunohistochemistry (IHC; ×40).

FIG. 21A shows tumor volume over 28 days post-tumor challenge with either vehicle plus α-IgG2a (blue line), S-equol plus α-IgG2a (red line), vehicle plus α-PD-1 (purple line) and S-equol plus α-PD-1 (green line). FIG. 21B shows EMT6 tumor weight post-tumor challenge with either vehicle plus α-IgG2a (blue dots), S-equol plus α-IgG2a (red dots), vehicle plus α-PD-1 (purple dots) and S-equol plus α-PD-1 (greendots). FIG. 21C shows the size of tumors post-tumor challenge with either vehicle plus α-IgG2a (top row), S-equol plus α-IgG2a (second row from top), vehicle plus α-PD-1 (third row from top) and S-equol plus α-PD-1 (bottom row).

FIG. 22A shows CD45 expression. FIG. 22B shows CD8 expression. FIG. 22C shows CD4 expression. FIG. 22D shows NK1.1 expression. FIG. 22E shows CD107a expression as percent CD3 expression. FIG. 22F shows CD107a expression as percent CD8 expression. FIG. 22G shows CD107a expression as percent CD4 expression. FIG. 22H shows CD107a expression as percent NK1.1 expression.

FIG. 24A is a achematic representation of the bone marrow adoptive transfer approach used to generate WT>WT or WT>KI mice. Five-week-old CD45.1+B6.SJL were irradiated and reconstituted with CD45.2+WT or KI bone marrow as previously described (Wang 2011). B16 melanoma growth in WT>WT and KI>WT male (FIG. 24B) and female (FIG. 24C) chimera mice. FIG. 24D shows qPCR for indicated genes from whole lung lysates from mouse challenged as in FIG. 24B. FIG. 24E shows flow cytometry of B16 melanoma-infiltrating (FIG. 24E) CD8+, (FIG. 24F) CD8+IFNγ+cell content as in (FIG. 24B). Flow cytometry was used to analyze the (FIG. 24G) proportions and (24H) MFI of CD8+CXCR3+ cells in the TDLN as in FIG. 24B. FIG. 24I shows ERβ protein levels in the purified natural killer (NK), CD4+, CD8+ T cells, dendritic cells (DC) from spleen, as well as mouse lung and ovary tissue lysate (GAPDH shown as loading controls). (FIG. 24J) B16 melanoma growth in Rag1−/−mice after adoptive transfer of CD8+ T cells from WT or KI mice. FIG. 24K shows revalence of CD8+ percentage of total CD45+ in the B16 melanoma-488 infiltrating cell population.

FIG. 25A shows IP-Western blot of pY36 (up) and total ERβ (bottom) in mouse primary CD8 T cells with/without anti-CD3/CD28 treatment for the indicated times. FIG. 25B shows ELISA measurement of cytokine production by purified CD8 T cells from WT or KI mice upon stimulated with or without anti-CD3/CD28. FIG. 25C shows CD8+T cells from WT or KI mice were stimulated with anti-CD3/CD28 antibodies for indicated times and indicated phospho-proteins (p-) and total proteins were analyzed by immunoblotting. β-Tubulin was used as a loading control. FIG. 25D shows co-IP of endogenous ERβ, p-Lck and p-ZAP-70 in EL4 cells with anti-CD3/CD28 treated for indicated times.

FIG. 26A shows IP-Western blot of pY36 (up) and total ERβ (bottom) in mouse primary CD8 T cells pretreated with S-equol for 4 hrs, followed by anti-CD3/CD28 treatment for the indicated times. FIGS. 26B and 26C show B16 melanoma growth and tumor weight from wild type C57BL/6J male mice with four arm treatments. Vehicle+α-IgG, S-equol+α-IgG, Vehicle+α-PD-1, S-equol+α-PD-1. FIG. 26D shows EMT-6 mammary tumor growth and (FIG. 26E) tumor weight from wild type BALB/c female mice with four-arm treatments. Vehicle+α-IgG, S-equol+α-IgG, Vehicle+α-PD-1, S-equol+α-PD-1. GSEA analysis in ERβ-high versus ERβ-low human melanoma TILs (tumor infiltrating lymphocytes). The enrichment of (FIG. 26F) NFAT pathway and (FIG. 26G) TNFα signaling were evaluated.

FIG. 27A shows a homologous recombination approach. FIG. 27B shows confirmation of the genomic alteration at the native Esr2 locus. FIG. 27C shows pictures of the KI mice.

FIG. 28A shows colon tumor volume in male mice days after tumor challenge. FIG. 28B shows melanoma tumor volume in female mice days after tumor challenge. FIG. 28C shows lung metastases in KI mice.

FIG. 29A shows % CD3$^+$ of total cells. FIG. 29B shows % CD4$^+$ of total cells. FIG. 29 shows % CD8$^+$ of total cells. FIG. 29D shows % CD45$^+$ of live cells. FIG. 29E shows % CD4$^+$ of total T cells. FIG. 29F shows % CD8$^+$ of total T cells.

FIG. 31A is a FACS plot that shows no effect of ERβ on MDSC abundance in tumor-bearing mice. FIG. 31B is a graph that shows percent survival days post challenge. FIG. 31C shows tumors in mice.

FIG. 32A shows % CD4$^+$ cells of CD45 in KI versus wild type mice. FIG. 32B shows MHC II (MFI of CD11c$^+$) in KI versus wild type mice. FIG. 32C shows CD44$^+$ CD62L$^-$ (% of CD8$^+$) in KI versus wild type mice. FIG. 32D shows TNFα (MFI of CD8$^+$) in KI versus wild type mice. FIG. 32E shows perforin (MFI of CD8±) in KI versus wild type mice. FIG. 32F shows PD1$^+$Lag3$^+$ (% of CD8$^+$) in KI versus wild type mice.

FIG. 33A shows tumor volume (mm$^3$) days post challenge in E0771. FIG. 33B shows tumor weight (g) with various combination therapies. FIG. 33C shows tumor volume (mm$^3$) days post challenge in AT3. FIG. 33D shows tumor weight (g) with various combination therapies.

FIG. 34A shows a correlation of ESR2 vs. CD4. FIG. 34B shows a correlation of ESR2 vs. CD8A. FIG. 34C shows a correlation of ESR2 vs. GZMB. FIG. 34D shows expression of markers versus infiltration level. FIG. 34E shows expression of markers.

DETAILED DESCRIPTION OF THE INVENTION

Figure 1:
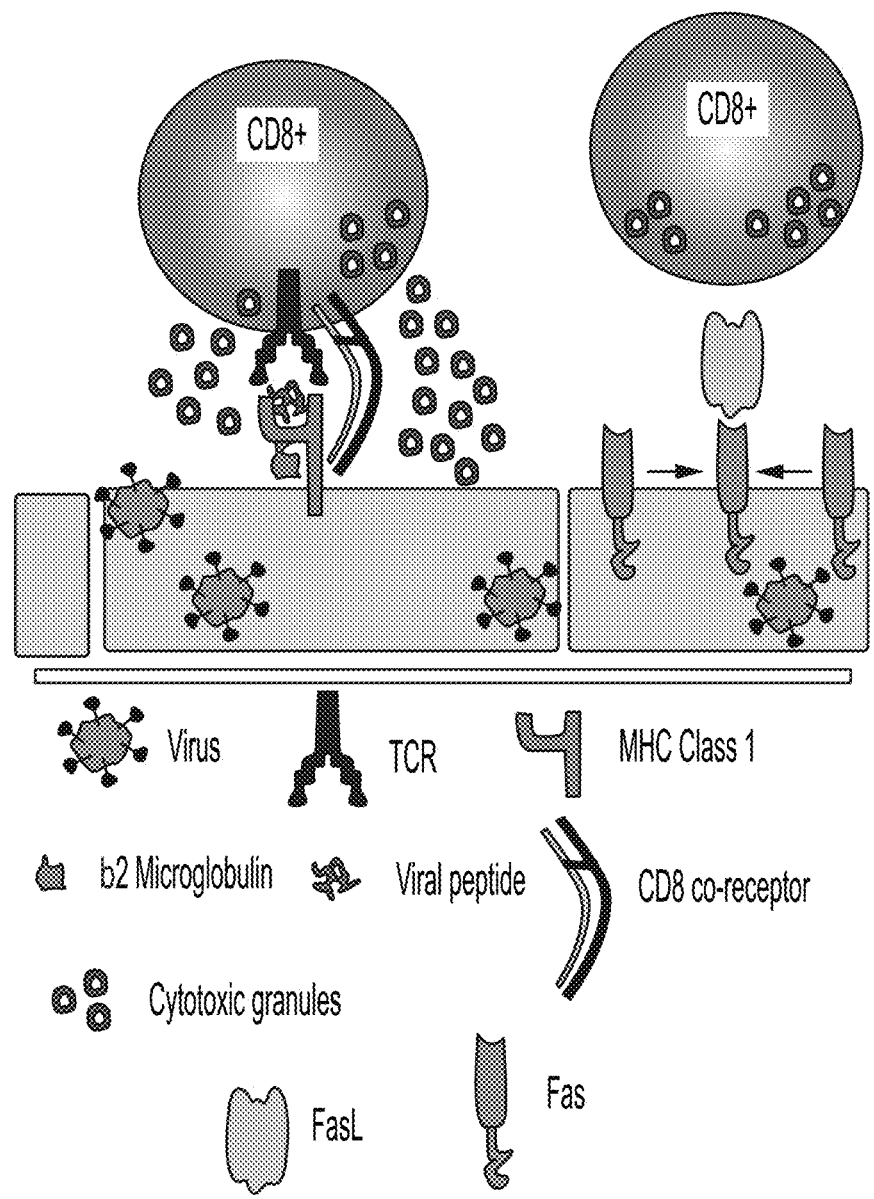
FIG. 1. Schematic depiction of the action of CD8$^+$ cells.
Figure 2:
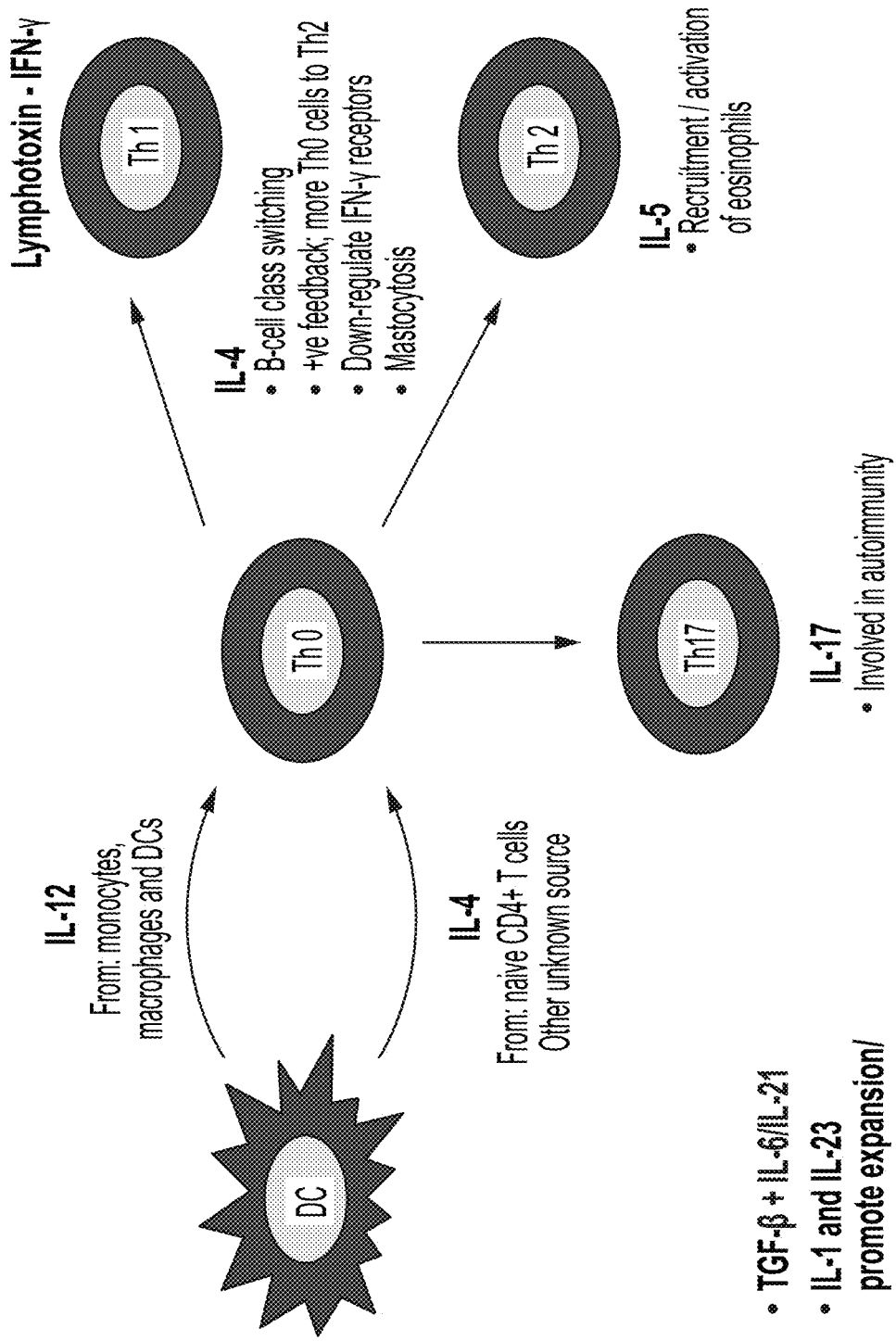
FIG. 2. Schematic depiction of the action of CD4$^+$ cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

"Substantially pure" means about 90% pure, preferably 95% pure, and more preferably 98% pure of any contaminating proteins.

"Substantially free" means about less than about 10%, preferably less than 5%, and more preferably less than 2% of any contaminating proteins.

"Approximately" or "about" means within +/−10%, preferably within +/−5%, more preferably within +/−2% of that which is being measured.

"TNBC tumors" are defined as less than or equal to 5% nuclear staining of carcinoma cells for ER-alpha and PR and either 0, 1+ or 2+ staining for HER-2 by IHC. If only fluorescence in situ hybridization (FISH) is performed for HER-2, it must be less than or equal to 2.0. Tumor cells that show distinct nuclear staining of total ER-beta or pY36 (regardless of cytoplasmic staining) will be scored as positive.

The present invention relates to the prevention and/or treatment of breast cancer or melanoma with S-equol.

Dosage amounts and administration schedules for S-equol will depend on whether the S-equol is being administered prophylactically to a patient at risk of developing melanoma, or being administered as treatment for a patient already diagnosed with melanoma. A person at risk for developing melanoma may be a person with a family history of melanoma, and/or may have one or more mutations in a CDKN2A gene, MDm2 gene, RB1 gene, or MC1R gene. In a patient already diagnosed with melanoma, dosages and administration schedules may also vary depending on the stage of the cancer (stage I, stage II, stage III, stage IV or stage V), the number of lymph nodes involved, tumor size and the availability of and/or decision to co-administer other therapies. Dosages and administration schedules may also vary depending on various molecular markers present on or in tumor cells, including, but not limited to Hsp90, RGS1, osteopontin, HER3, ING4, ING3, NCOA3, MCM4, MCM6, Ki67 and pY36. Diagnostic tests for markers which are prognostic for the aggressiveness and/or likelihood of recurrence of a tumor may be used as a factor or determining dosage regimens. (Gogas et al. (2009), incorporated by reference in its entirety for all purposes.)

S-equol can be administered one or more times per day at 1-400 mg per dose, more preferably 10-320 mg, more preferably 50-150 mg. Non-limiting examples include 2 mg, 5 mg, 10 mg, 15 mg, 20 mg, 40 mg, 50 mg, 80 mg, 100 mg, 150 mg, 160 mg, 200 mg, 250 mg, 300 mg 320 mg, etc. or approximately or about those doses. The dose may be administered one, two, three or four times per day, preferably twice per day (B.I.D.) The regimen can be continued indefinitely, or for such time in intervals where markers are examined and responsiveness to the dose is determined. Examples of such intervals are two weeks, four weeks, two months, four months, six months, etc. or about or approximately those intervals. No upper limit, with respect to administration schedule, is required.

The S-equol administered is preferably formulated for oral administration; however, other routes of administration are also contemplated, including rectal, optical, buccal (for example sublingual), parenteral (for example subcutaneous, intramuscular, intradermal and intravenous) and transdermal administration.

Compositions or formulations according to the present invention can comprise one or more pharmaceutically-acceptable or industrial standard fillers. The filler must not be deleterious to a subject treated with the composition. The filler can be solid or a liquid, or both. The filler can be formulated with the active S-equol as a unit-dose, for example a tablet, which can typically contain from about 10% to 80% by weight of S-equol. Compositions can be prepared by any of the well known techniques of pharmacy, for example admixing the components, optionally including excipients, diluents (for example water) and auxiliaries as are well known in the pharmaceutical field.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions can be prepared by any suitable method of pharmacy which includes the step of bringing into association the active S-equol and one or more suitable carriers (which can contain one or more accessory ingredients as noted above). In general the compositions of the invention are prepared by uniformly and intimately admixing the S-equol with a liquid or finely divided solid carrier, or both, and then, if necessary, shaping the resulting mixture. For example, a tablet can be prepared by comprising or moulding a powder or granules containing the extract, optionally with one or more accessory ingredients. Compressed tablets can be prepared by compressing in a suitable machine, the extracts in the form of a powder or granules optionally mixed with a binder, lubricant, inert diluents, and/or surface active/dispersing agent(s). Moulded tablets can be made by moulding, in a suitable machine, the powdered compound moistened with an inert liquid binder.

Suitable fillers, such as sugars, for example lactose, saccharose, mannitol or sorbitol, cellulose preparations and/or calcium phosphates, for example tricalcium phosphate or calcium hydrogen phosphate, and also binders such as starch pastes using, for example, corn, wheat, rice or potato starch, gelatin, tragacanth, methylceullose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients can be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which can comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as microcrystalline cellulose, acetylcellulose phthalate or hydroxypropylmethylcellulose phthalate. Dyes or pigments can be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules can comprise the extracts in the form of granules, for example in admixture with fillers, such as lactose, binders, such as starches, and/or glicants, such as talc or magnesium stearate, and, where appropriate, stabilizers. In soft capsules, the extract is preferably dissolved or suspended in suitable liquids, such as fatty oils, paraffin oil or liquid polyethylene glycols, to which stabilizers can also be added.

According to one aspect of the invention, the compositions comprising S-equol include those described in U.S. Pat. No. 7,960,432 (filed Jul. 3, 2008); U.S. Pat. No. 7,396,855 (filed Jul. 24, 2003); and U.S. Pat. No. 9,408,824 (filed Mar. 5, 2014)—the disclosures of each are hereby incorporated by reference in their entireties.

According to another aspect of the invention, S-equol can be prepared chemically (i.e., chemical synthesis) according to the processes described in U.S. Pat. No. 8,716,497 (filed Sep. 10, 2012); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005) and U.S. Pat. No. 9,914,718 (filed Oct. 14, 2014)—the disclosures of each are hereby incorporated by reference in their entireties. For example, S-equol can be enantioselectively prepared using an iridium catalyst with a chiral ligand. These methods of enantioselectively preparing S-equol are incorporated by reference.

According to another aspect of the invention, S-equol can be a single anhydrous crystalline polymorph of S-equol, such as the anhydrous crystalline polymorph of S-equol described in U.S. Pat. No. 9,914,718 (application Ser. No. 14/883,617, filed Oct. 14, 2015)—the disclosure of which, including the chemical and physical properties used to characterize the anhydrous crystalline polymorph of S-equol, is incorporated by reference in their entireties. For example, the anhydrous crystalline polymorph of S-equol described in U.S. Patent Application Publication No. 2016/0102070 has the following characteristic X-ray powder diffraction pattern wavenumbers ($cm^{-1}$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461. The characterizations of anhydrous crystalline polymorph of S-equol are incorporated by reference.

The S-equol can be administered in combination with one or more additional cancer treatments, including surgery, cytotoxic chemotherapy, radiation, immunotherapy, cancer vaccines, inhibitors of cellular pathways (protein or peptide, nucleic acid-based [antisense oligonucleotides including DNA oligonucleotides, antisense siRNA, shRNA] and/or hormonal (adjuvant endocrine) therapy. Examples of cytotoxic chemotherapy suitable for treating melanoma include, but are not limited to imiquimod cream (Zyclara®), dacarbazine (DTIC) and temozolomide (Temodar®). Examples of immunotherapy include but are not limited to nivolumab (Opdivo®), pembrolizumab (Keytruda®), nivolumab (Opdivo®), and ipilimumab (Yervoy®), imatinib (Glevac®), nilotinib (Tasigna®) or interferon and interleukin-2 (IL-2). Other options include injections of the T-VEC vaccine (Imlygic®), or the Bacille Calmette-Guerin (BCG) vaccine.

Examples of cytotoxic chemotherapy suitable for treating breast cancer include, but are not limited to anthracyclines such as doxorubicin (Adriamycin®) and epirubicin (Ellence®), taxanes such as paclitaxel (Taxol®) and docetaxel (Taxotere®), 5-fluorouracil (5-FU), capecitabine, cyclophosphamide (Cytoxan®) and carboplatin (Paraplatin®). Examples of adjuvant endocrine therapy include tamoxifen and aromatase inhibitors such as anastrozole (Arimedix®), exemestane (Aromasin®) and Letrozole (Femara®). Examples of immunotherapy include but are not limited to pembrolizumab (Keytruda®, MK-3475), nivolumab (Opdivo®), durvalumab (MEDI4736), tremelimumab, atezolizumab (MPDL3280A), avelumab, trastuzumab, PDR001, and MGD009. An examples of a known inhibitor of a cellular pathway is a tyrosine kinase inhibitor such as lapatinib.

Appropriate dosages of immunotherapy monoclonal antibodies or other cancer therapeutic are determined based on the indication, and their determination is well within the skill in the art. Dosing may be in mg, in mg/kg or mg/m$^2$. See, Sachs et al. (2016), which is incorporated by reference herein in its entirety for all purposes, including examples of therapeutic antibodies, small molecules and dosages. The S-equol and/or additional therapeutic composition may be administered once, twice, three times or more per day, depending on the dose, toxicity and indication. Dosing may occur over several days, weeks or months, and may be continuous or intermittent. Typical dosages for immunotherapeutics are 50-500 mg/day, more preferably 100-400 mg/day, more preferably 150-250 mg/day. In certain embodiments, the dose may be 150 mg/day or 150 mg twice per day, or 250 mg/day or 250 mg twice a day. In other embodiments the dosage may be given based on patient weight, for instance 0.5-10 mg/kg, more preferably about 1, 2 or 5 mg/kg. Dosage may also be given as mg/m$^2$, for example 50-500 mg/m$^2$, more preferably 100-300 mg/m$^2$, for example about 100, 150, 200, 250 or 300 mg/m$^2$.

The dosages may be about or greater than the lower end of any of the afore-stated ranges, or about or less than the upper end of any of the afore-stated ranges.

Responsiveness to the S-equol+/− other cancer therapy can be assessed by analyzing one or more cellular markers, by imaging techniques, by cellular proliferation assays and by direct examination of tumors. The analysis of cellular markers can be done with immunohistochemical or immunocytochemical techniques or by nucleic acid detection, such as hybridization techniques and polymerase chain reaction (PCR). A preferred biomarker to assess mitotic division and tumor growth is Ki67 (Beelen et al. (2012); Urruticoechea et al. (2005)).

The following examples are provided to aid the understanding of the present invention, the true scope of which is set forth in the appended claims. It is understood that modifications can be made in the procedures set forth without departing from the spirit of the invention.

EXAMPLES

The processes of the present invention will be better understood in connection with the following examples, which are intended as an illustration only and without limiting the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

Figure 4:
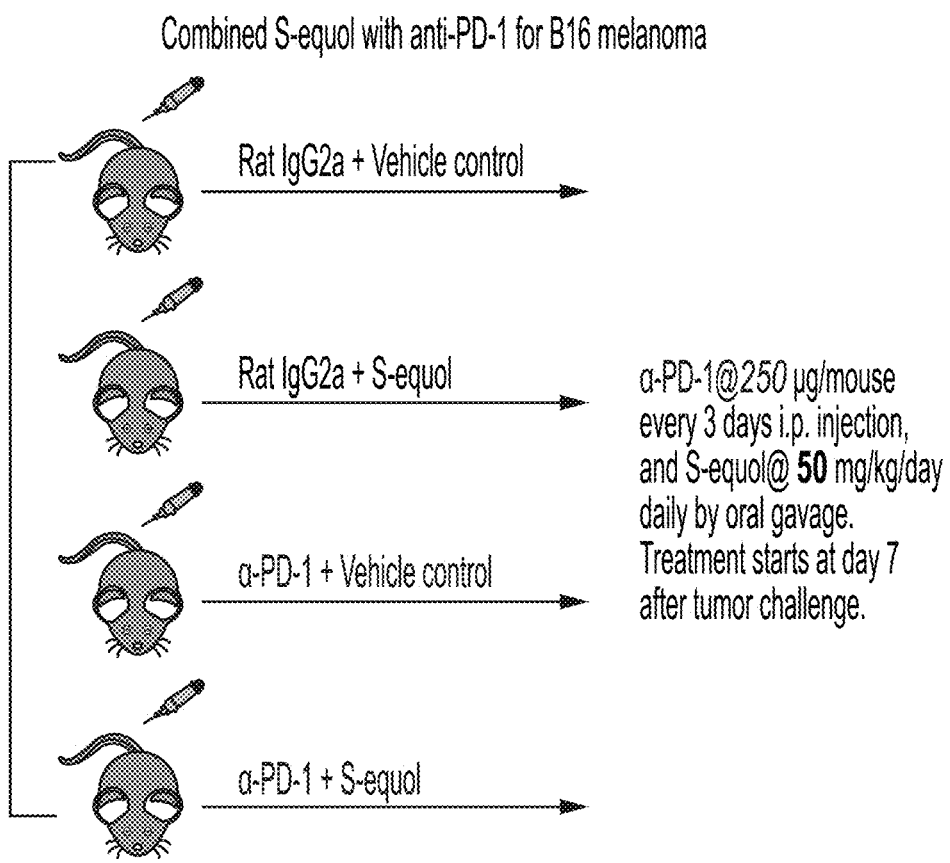
FIG. 4. A schema for combination therapy. Mice were administered one of: (1) vehicle+rat IgG2a; (2) S-equol+rat IgG2a; (3) vehicle+anti-PD-1 antibody; or (4) S-equol+anti-PD-1 antibody. Mice receiving anti-PD-1 antibody were given 250 μg every 3 days, intraperitoneally, and mice receiving S-equol were given 50 mg/kg per day by oral gavage. Treatment started 7 days after tumor challenge with B16 melanoma.

To determine whether the newly identified phosphotyrosine switch regulates ERβ tumor-extrinsic function, a whole-body knock-in (K1) mouse model (C57BL/6) was established in which the corresponding tyrosine residue of endogenous mouse ERβ is mutated to phenylalanine (Y-F). Consistent with previously reported ERβ knockout (KO) mice (Krege et al. (1998)), these phosphorylation mutant KI mice had no overt developmental defects and were grossly indistinguishable from their WT littermates (unpublished data). Survey of ERβ expression in KO and KI mice indicated that the Y-F mutant protein was expressed at levels comparable to WT ERβ in multiple tissues, including bone marrow and spleen (FIG. 4A). Syngeneic murine tumor cells of various origins were then transplanted, including the MMTV-Wnt mammary tumor cell line with a basal-like breast cancer profile (Pfefferle et al. (2013)), into WT and KI recipient mice. In all cases, tumor cells grew more robustly in ERβ KI recipient mice than in their syngeneic WT counterparts (FIG. 4B, and data not shown). These data clearly demonstrate that the phosphotyrosine switch is important for ERβ tumor-extrinsic antitumor activity in multiple tumor types.

Example 2

Figure 5:
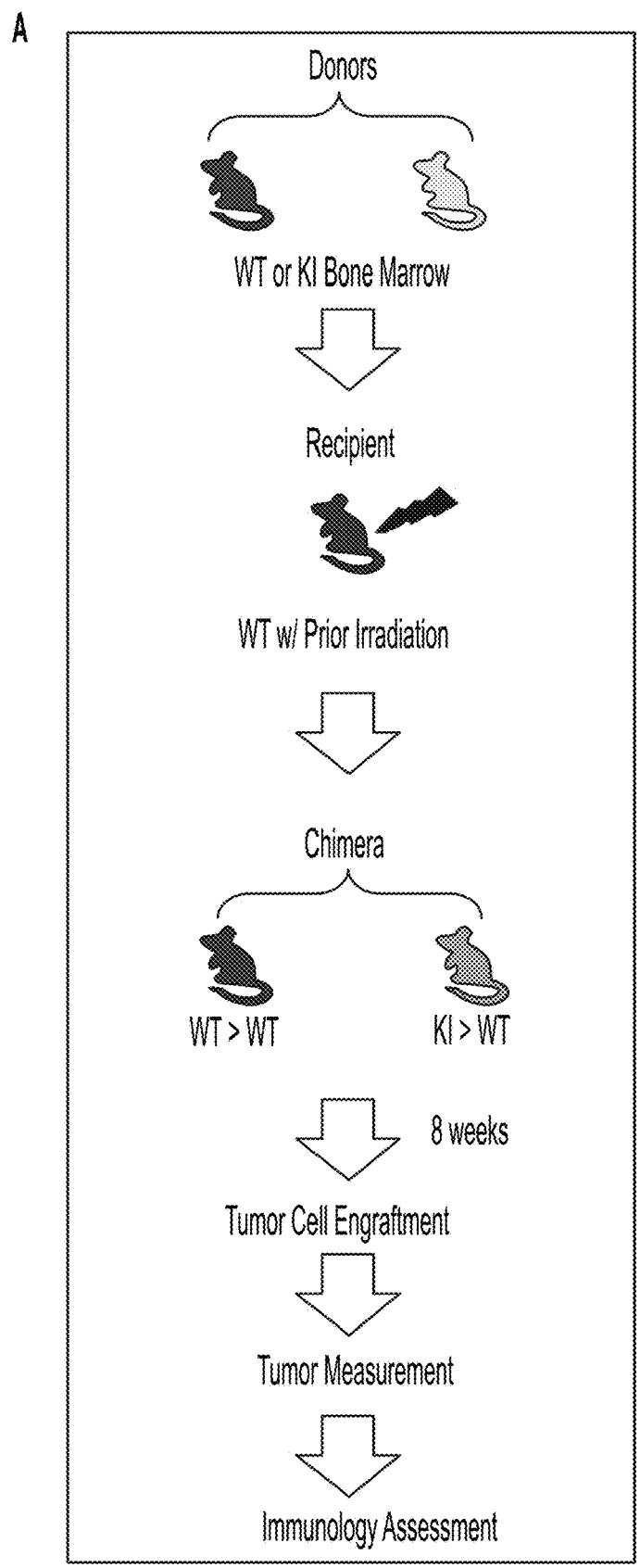
FIG. 5. A role of ERβ signaling in immune cells.
Figure 5:
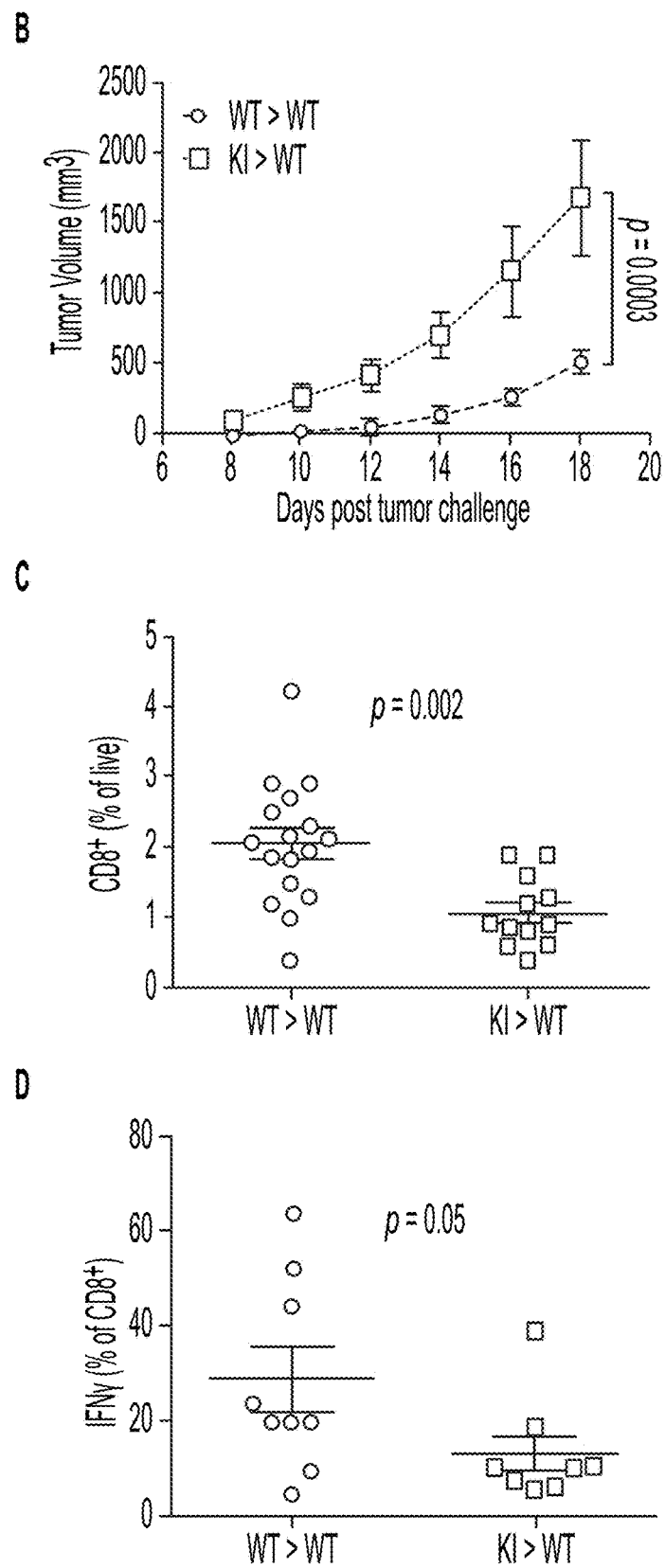
Figure 6:
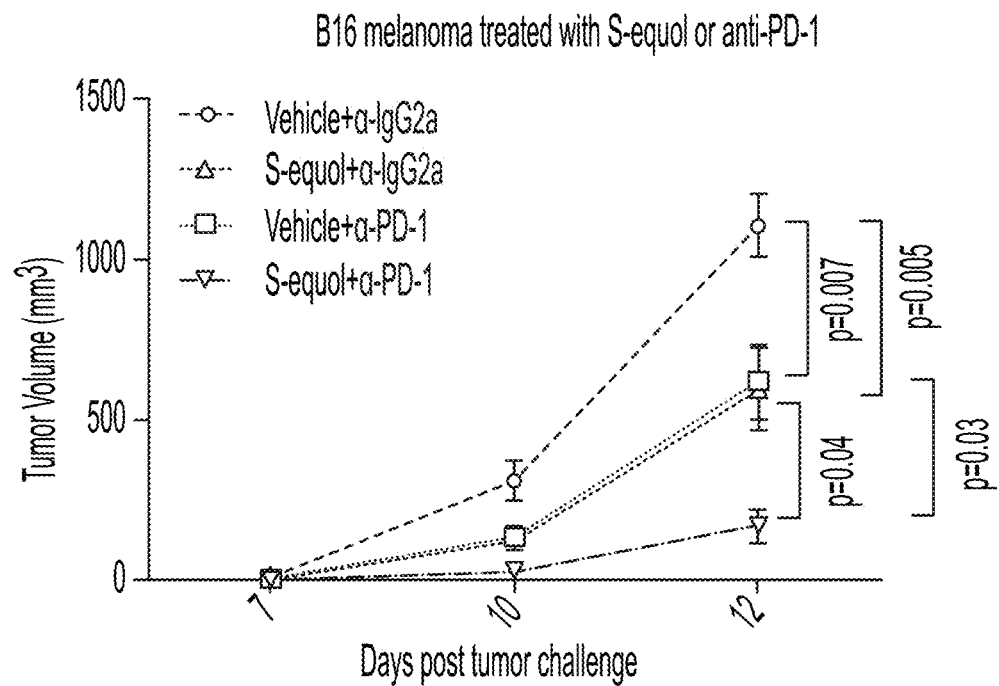
FIG. 6. Effect of S-equol in combination with an anti-PD-1 antibody on mice challenged with an B16 melanoma tumor cell line over 12 days. Mice were administered anti-PD-1 antibody at 250 μg every 3 days, intraperitoneally, and S-equol at 50 mg/kg per day by oral gavage.
Figure 7:
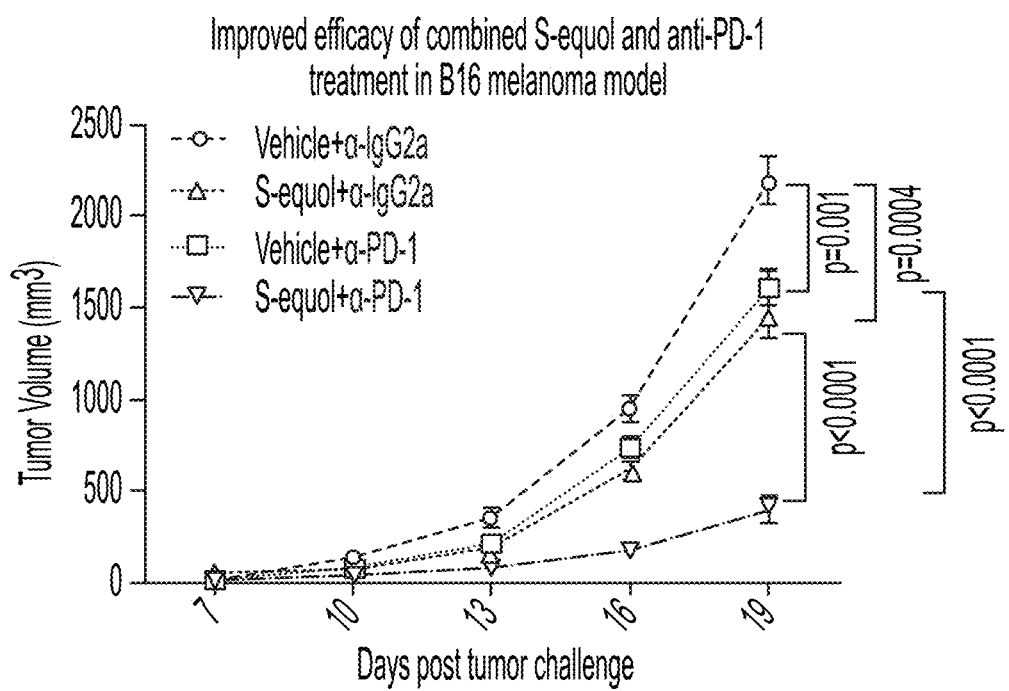
FIG. 7. Effect of S-equol in combination with an anti-PD-1 antibody on mice challenged with an B16 melanoma tumor cell line over 19 days. Mice were administered anti-PD-1 antibody at 250 μg every 3 days, intraperitoneally, and S-equol at 50 mg/kg per day by oral gavage.
Figures 8A, 8B:
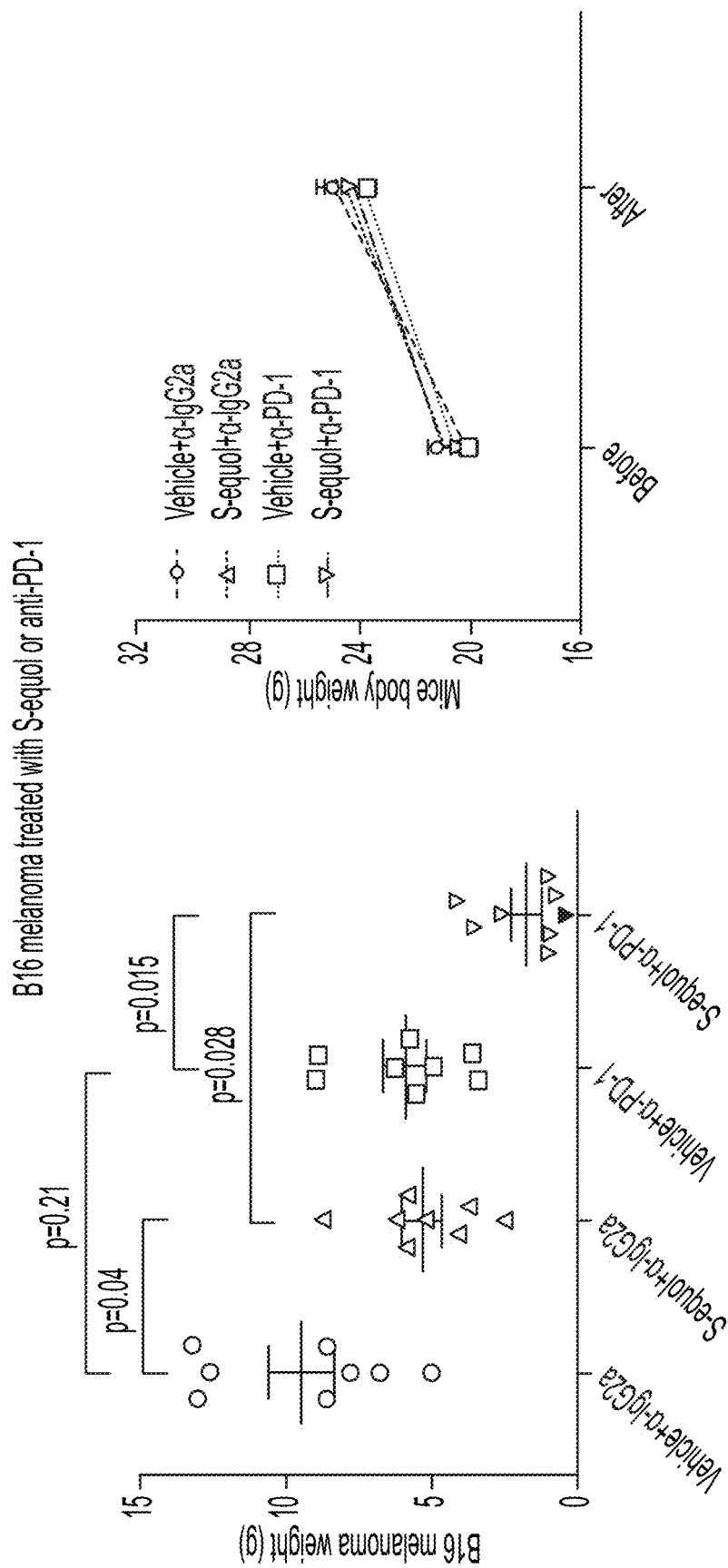
FIGS. 8A-8B. Effect of S-equol in combination with an anti-PD-1 antibody on tumor weight in mice challenged with an B16 melanoma tumor cell line.
Figures 9A, 9B:
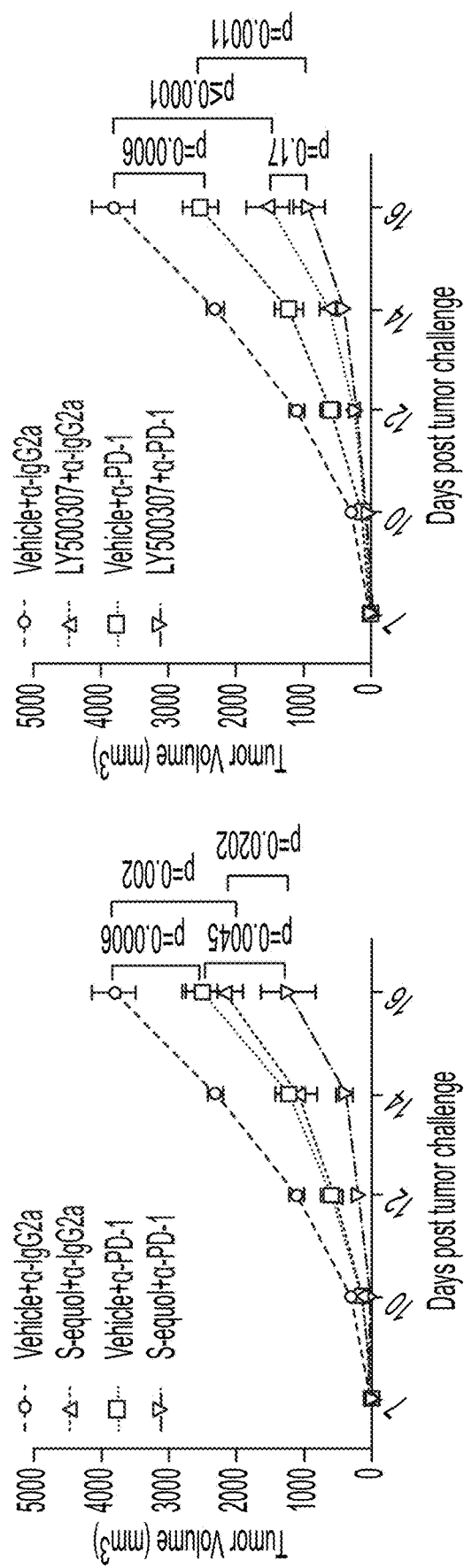
FIGS. 9A-9B. Effect of S-equol in combination with an anti-PD-1 antibody and LY500307 on mice challenged with an B16 melanoma tumor cell line over 16 days. Mice were administered anti-PD-1 antibody at 250 μg every 3 days, intraperitoneally, and S-equol at 50 mg/kg per day by oral gavage.

The following experiment sought to delineate further the host ERβ signaling in tumor inhibition based on the role of antitumor immunity and recent clinical advances in cancer immunotherapies (Topalian et al. (2015); Chen and Flies (2013); Sharma and Allison (2015)). A mouse chimera experiment was conducted involving a bone marrow transplant. As illustrated in FIG. 5A, WT recipient mice were first irradiated (10 Gy) to kill endogenous bone marrow cells, followed by transplant with bone marrow from syngeneic KI or WT donors. After confirming successful chimerism in KI>WT and WT>WT mice, tumor cells were injected 8 weeks after bone marrow transplant. Tumor growth was significantly greater in KI>WT chimeras (with KI immune cells) versus WT>WT controls (FIG. 5B). This suggests that KI immune cells poorly controlled tumor growth. Thus, these data link the importance of tumor extrinsic ERβ antitumor activity to the immune response.

Example 3

Next, tumor-infiltrating immune cell populations were analyzed. Total numbers of tumor-infiltrating CD4$^+$ and CD8$^+$ T cells were reduced in KI>WT versus WT>WT mice (FIG. 5C and data not shown), further supporting the notion that antitumor immunity in KI mice is compromised. Furthermore, the prevalence of IFNγ-producing CD8$^+$ (antitumor) cells was significantly lower in tumors from KI>WT versus WT>WT mice (FIG. 5D), suggesting compromised cytotoxic potency of CD8+ T cells in the absence of functional ERβ signaling. Additional preliminary data not shown here indicate that activation of dendritic cells, which prime antitumor T cells, was also compromised in KI>WT chimeric mice, as evidenced by their reduced MHC-II expression. Furthermore, effector T cells were less activated (lower CD44/CD62L) and had other reduced effector functions in KI>WT chimeras [e.g., lower tumor necrosis factor alpha (TNF)α, interleukin (IL)-2, and perforin, data not shown]. These data strongly suggest ERβ-dependent augmentation of antitumor CD8$^+$ T cell effector activity and improved intra-tumor immune cell accumulation. Therefore, rallying ERβ antitumor activity with clinically safe ERβ agonists such as S-equol will improve efficacy of existing anticancer immunotherapies and make them more effective to treat melanoma.

Example 4

Melanoma cell line B16 was tested to determine the effects of a PD-1 inhibitor, S-equol and a combination of the two therapies on tumor growth. This experimental design includes four arms: (1) controls, (2) αPD-1, (3) S-equol, and (4) αPD-1+S-equol (FIG. 4) by injecting into mice $5 \times 10^5$ cells subcutaneously. Antibodies were administered α-PD-1: 250 μg/mice by i.p. injection every 3 days and S-equol was administered at 50 mg/kg/day by oral gavage. Treatment began 7 day after tumor challenge. Tumor growth trajectories were compared within treated mice using a repeated measures linear mixed model. The primary outcome was the logarithm of the tumor size, and the test statistic is the treatment×time interaction. Tumors were measured about 10 times. The number of recipient mice use used in the studies (n=6 per group) was based on the above study. Results (FIGS. 6-9) from this experiment demonstrate the ability of S-equol to boost anticancer immunotherapy.

Example 5

In addition to measurements of tumor size and weight in each arm, immunophenotyping is performed to gain more mechanistic insight into the antitumor effects of mono- and combinational therapies. Tumors, spleens, and draining lymph nodes are harvested and weighed. Anti-coagulated blood was collected by cardiac puncture. Tumors are paraffin-embedded for immunohistochemistry and snap-frozen for mRNA and protein analysis by Luminex. Flow cytometry is used (for phenotype/functions) and ViCell (for quantification) to analyze immune cells from tumor infiltrates, tumor-draining lymph nodes, and spleens. Analyses include $CD3^+$ total T cells and $CD4^+$ and $CD8^+$ T cell subsets; effector function (e.g., IFN-γ, TNF-α, IL-2, perforin, CD107a); activation (e.g., CD69, CD44, CD62L); and exhaustion (e.g., PD-1, Tim3, Lag3). Antigen-presenting cells ($CD11b^+CD1c^-$ monocyte/macrophages, $CD11b^+$ CD11c+ dendritic cells), $NK1.1^+NKp46^+$ NK cells, regulatory T cells (Treg, $CD3^+CD4^+CD25^{hi}Foxp3^+$), and myeloid-derived suppressor cells (MDSC, $CD11b^+Gr-1^{hi}$) are also analyzed. $CD8^+$ T cell receptor diversity were assessed with a commercial kit (Adaptive Biotechnologies). Local cell proliferation is also tested with Ki67 and BrdU stain.

Example 6

Further work in a preclinical animal model supports the notion of using S-equol to treat melanoma. In immunocompromised mouse experiments, using B16, a murine tumor cell line know to be useful to study human melanoma metastasis and solid tumor formation, growth of tumors is suppressed with S-equol treatment compared to control. $0.5 \times 10^6$ B16 cells are injected into normal BL mice. When the tumor masses reach 50 to 80 mm³ (about one week after the inoculation), the mice are given daily subcutaneous injections of S-equol (20 or 60 mg/kg per day) or PBS as a vehicle control. Tumor development is followed by caliper measurements along two orthogonal axes: length (L) and width (W) and volume (V) is estimated by the formula $V=[L \times (W^2)]/2$. Tumors harvested from mice are fixed in 10% neutral-buffered formalin, dehydrated, embedded in paraffin, and sectioned at 3 μm thickness. Representative tumor sections from vehicle control and S-equol-treated mice are tested for Ki-67 expression to assess cell proliferation, and for ERβ pY36. Statistical significance in the experiments is assessed by two-tailed Student's t test. In all assays, $p<0.05$ is considered statistically significant.

Example 7

A pilot biomarker clinical study is performed in 20 subjects with documented melanoma to determine the effect of the ERβ agonist S-equol on Ki67 an indicator of tumor cell proliferation. Tumor cell proliferation is measured by immunohistological staining for Ki-67. Ki-67 is encoded by the gene MKI67 gene and is required to maintain individual mitotic chromosomes dispersed in the cytoplasm following nuclear envelope disassembly. Measuring the fraction of Ki-67-positive cells in a tumor is known to be a reliable parameter for assessing cancer patient prognosis. Subjects with TNBC are known to have very high levels of Ki67.

Patients enrolled in the study receive a history, physical, laboratory assessment, radiological imaging, and diagnostic biopsies. Immunohistochemistry (IHC) of Ki67 (proliferation marker), total ERβ, and pY36-ERβ (phosphorylated ERβ), B7H1 (also known as PDL-1) and MIA and S100B are conducted using core needle biopsy tissue samples prior to treatment. Patients are given oral S-equol 50 mg, twice daily for approximately two weeks (10-21 days) prior to the scheduled oncologic surgeries or start of primary systemic therapy. Tumor samples are obtained from the surgery or the two-week repeat biopsy. Post-treatment IHC evaluation of Ki67, total ERβ, phosphorylated ERβ (pY36) and MIA and S100B are obtained. Ki67 reduction is compared pre- and post-treatment with S-equol. S-equol causes a measurable decrease in Ki67, indicating its efficacy in this tumor type. A c-DNA microarray platform is also used to discover downstream transcriptional targets of ERβ resulting from activation by S-equol.

Figure 10:
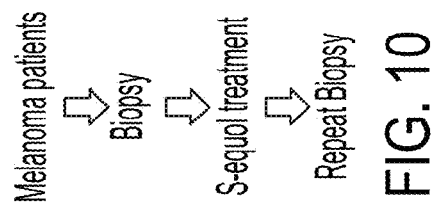
FIG. 10. Generalized protocol for human clinical trial with S-equol.
Figure 11:
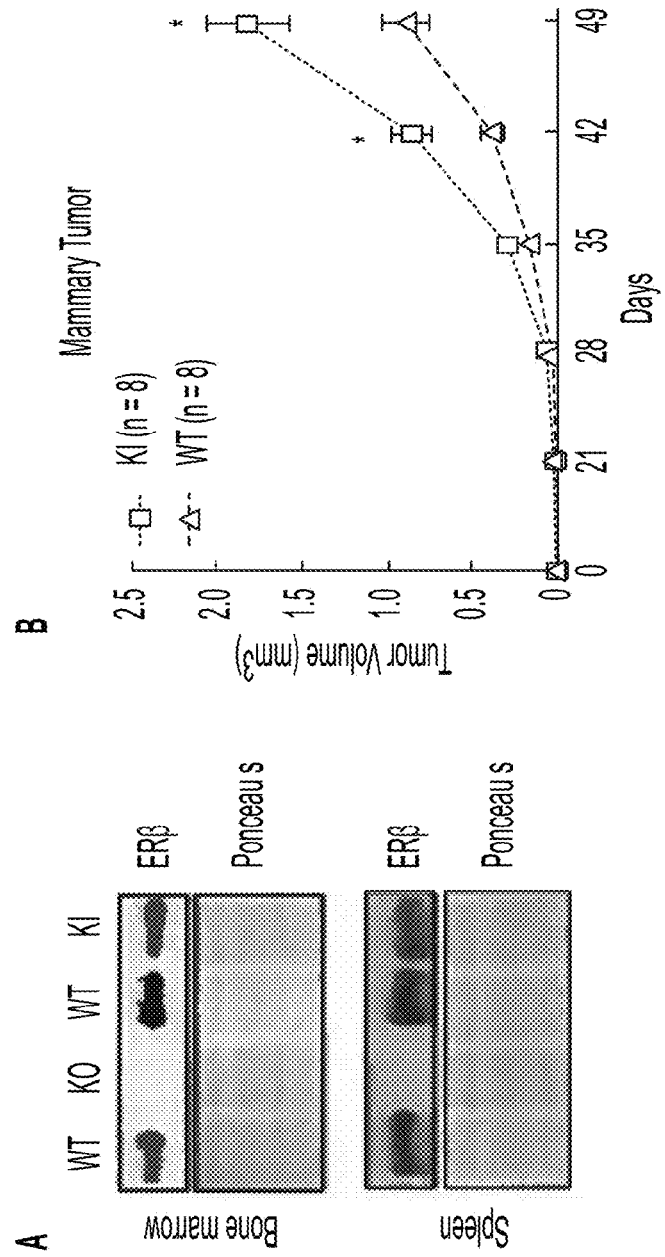
FIG. 11. Host effect of ERβ signaling on tumor growth.
Figure 12:
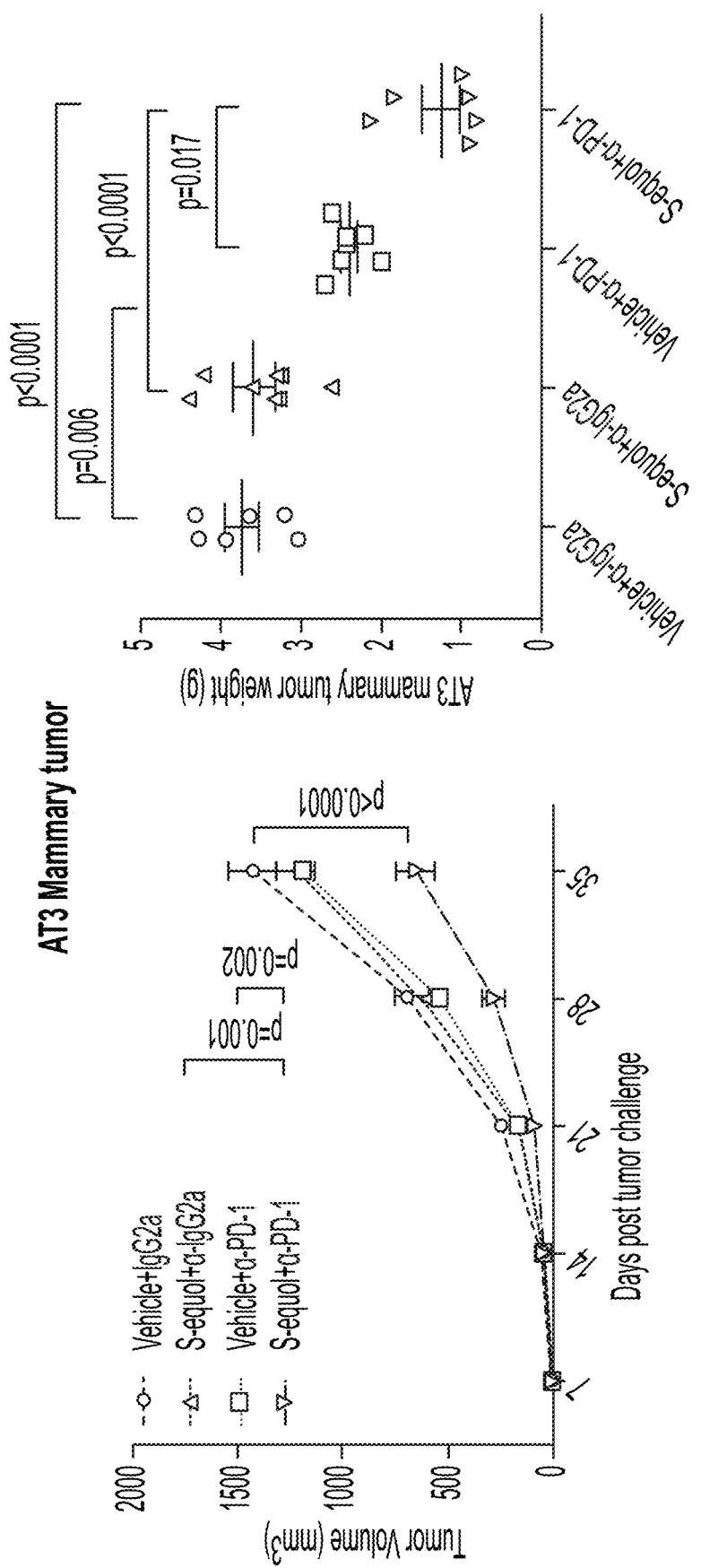
FIG. 12. Effect of S-equol in combination with an anti-PD-1 antibody on mice challenged with an AT3 mammary tumor cell line. Mice were administered anti-PD-1 antibody at 200 μg every 3 days and S-equol at 50 mg/kg per day.
Figure 12:
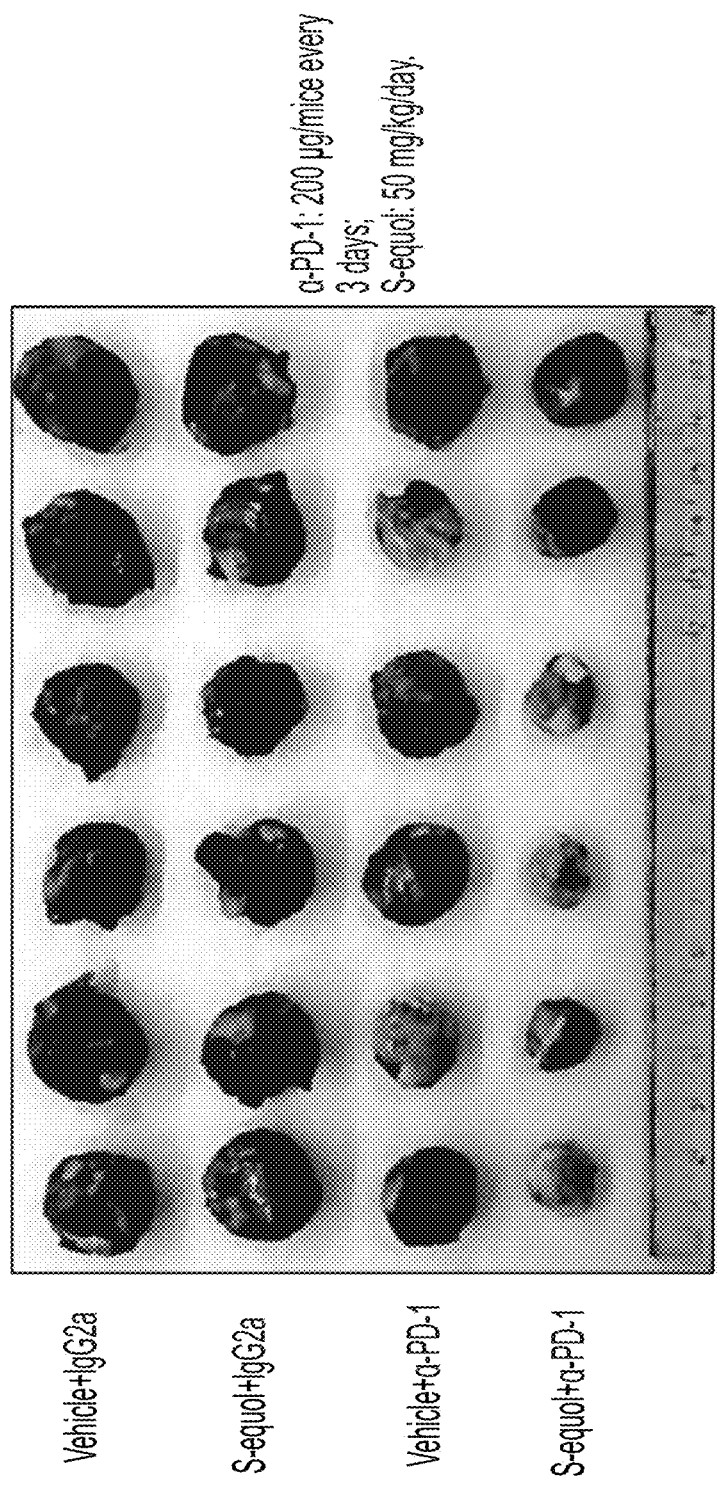
Figure 13:
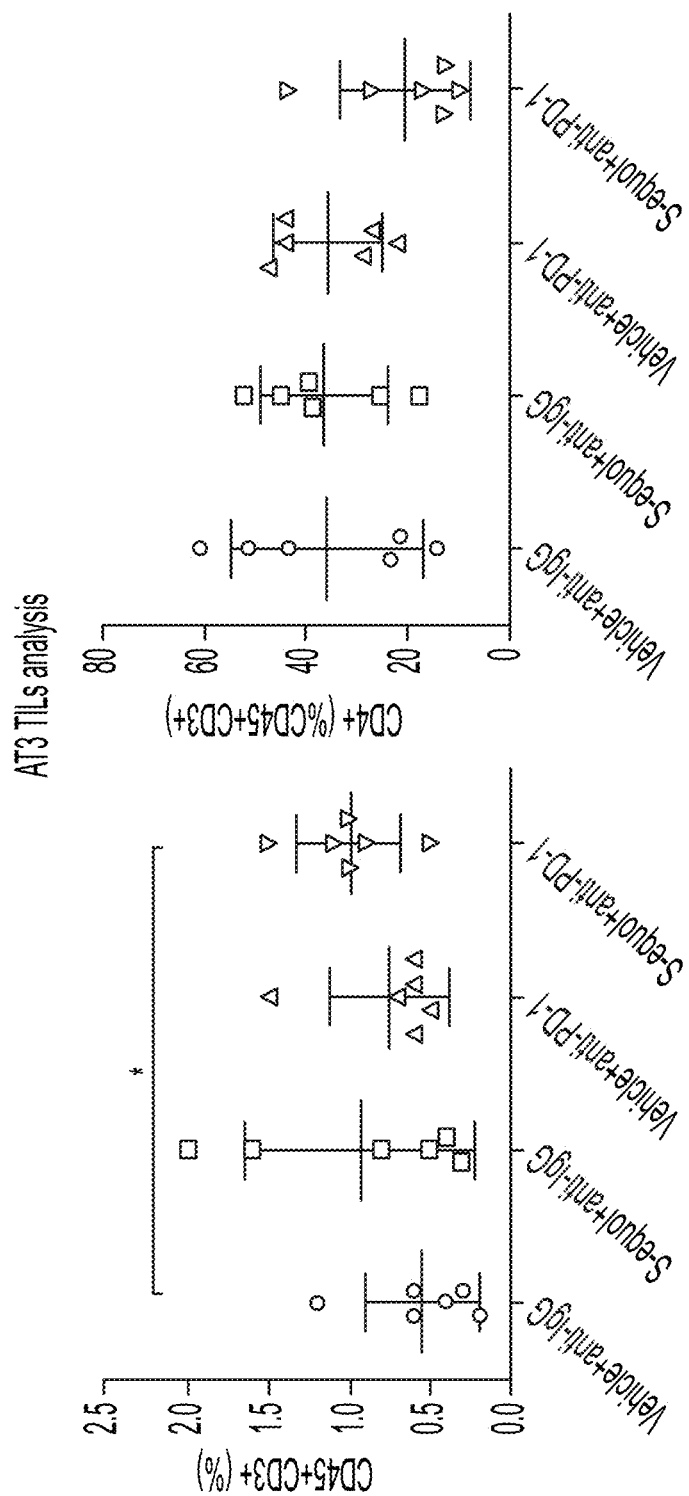
FIG. 13. Analysis of tumor-infiltrating lymphocytes.
Figure 13:
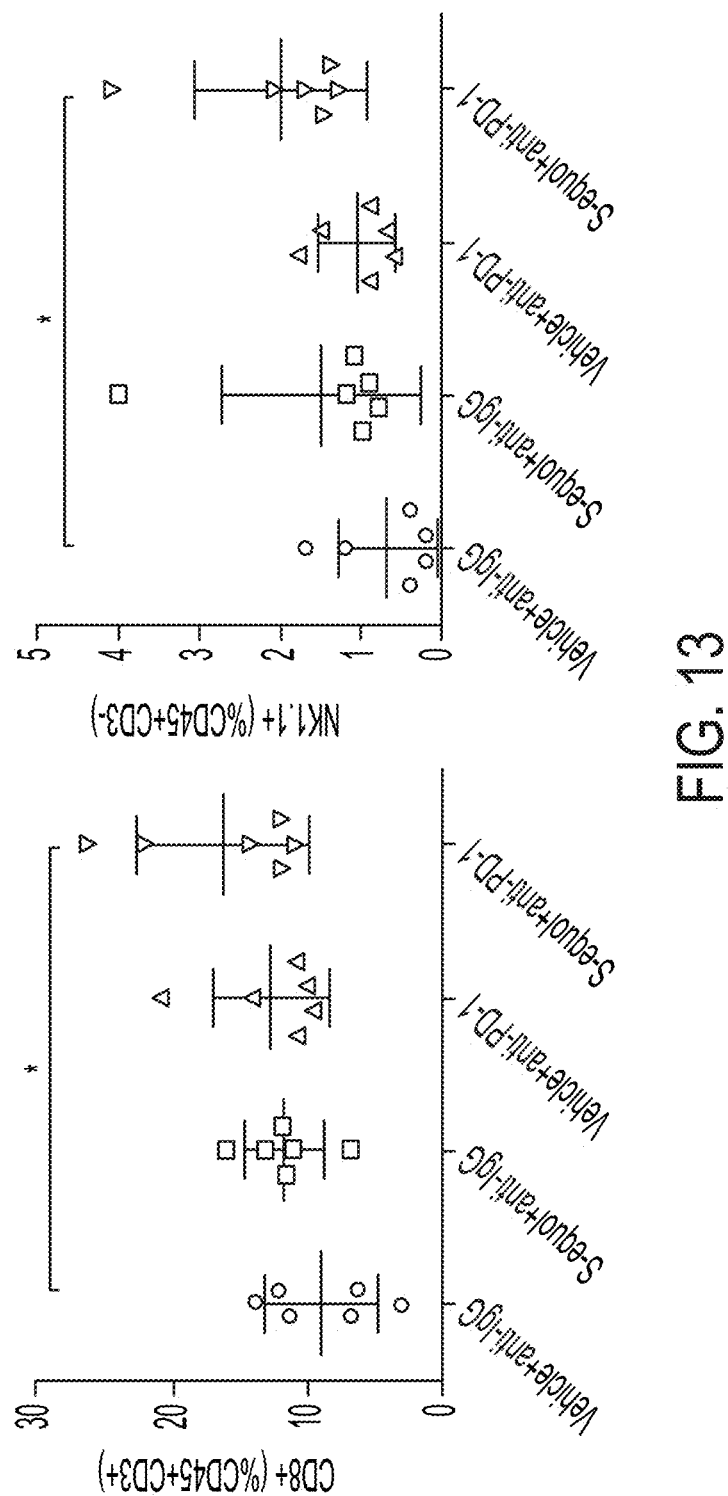
Figure 14:
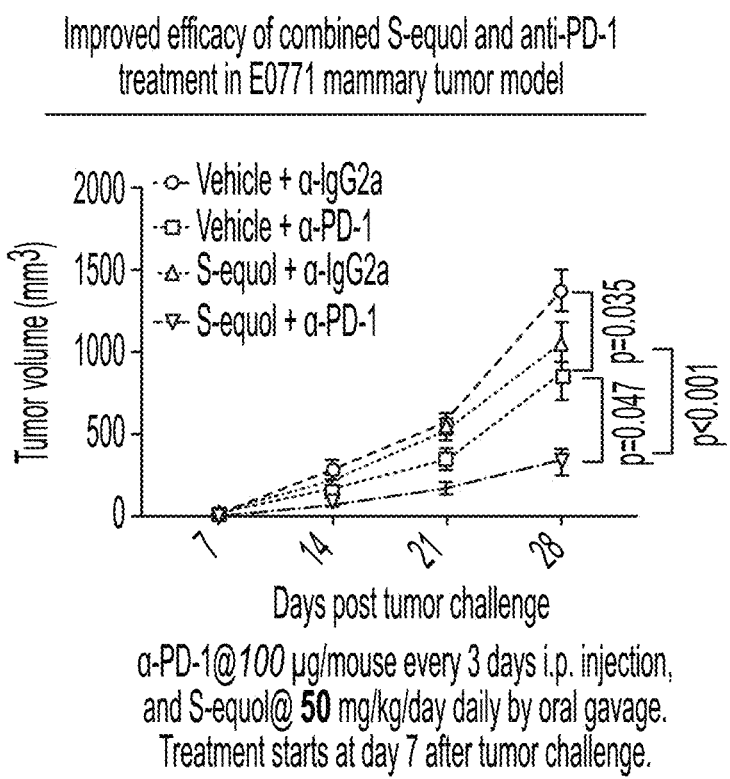
FIG. 14. Effect of S-equol in combination with an anti-PD-1 antibody on mice challenged with an E0771 mammary tumor cell line. Mice were administered anti-PD-1 antibody at 200 μg every 3 days and S-equol at 50 mg/kg per day.
Figure 15:
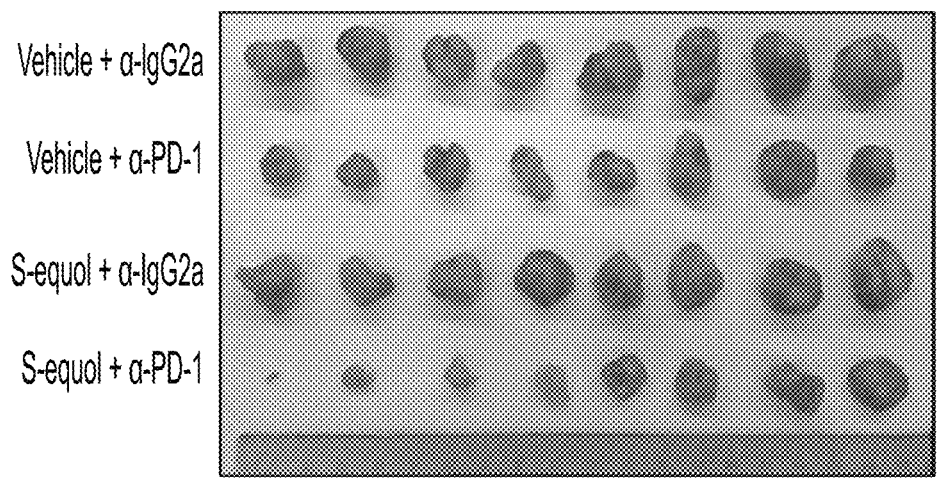
FIG. 15. Effect of S-equol in combination with an anti-PD-1 antibody on mice challenged with an E0771 mammary tumor cell line.
Figure 15:
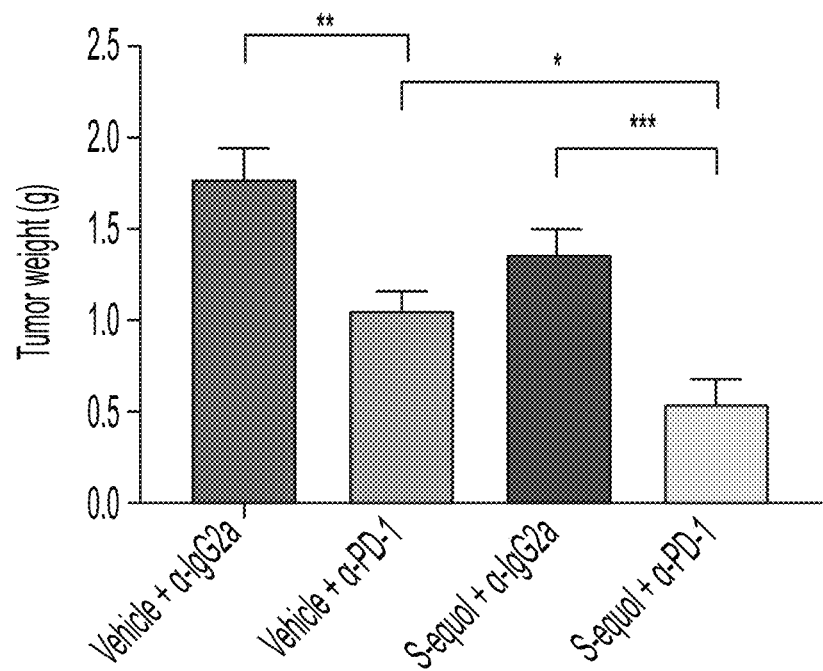

Patients eligible for the study have newly diagnosed, previously untreated, melanoma. All stages of the disease are eligible. They take S-equol during the time they undergo standard preoperative evaluation or pre-therapeutic work-up for advanced disease, such as staging procedures or central line placement. If primary surgery is performed, tissue leftover after standard diagnostic evaluation is used for the two-week biomarker assessment. If the patient does not have primary surgery at the end of the two-week S-equol treatment, a second set of biopsies is obtained before the start of any standard systemic therapy. See, FIG. 10.

A standard procedure for acquiring core biopsy is utilized for determining melanoma prior to enrollment. Whenever possible, the tumor tissues used for IHC analyses are acquired at the same time as the diagnostic core biopsy. The tissue samples are sent for staining of total and pY36, ERβ and Ki67, and analyzed. Whole-Genome DASL HT platform from Illumina, which is designed for gene expression profiling with extremely low input of RNA (50 pg), is used to interrogate paired FFPE tissue obtained before and after exposure to S-equol.

Statistical analysis is conducted which shows that ERβ-expressing melanoma responds to S-equol as manifested by measurable decline in Ki67. The primary analysis estimates the geometric mean change of the Ki67 expression from baseline to two weeks. This is performed using a one-sample t-test of the pre/post differences in the log-transformed data, and summarized by the 95% confidence interval. All computations are performed with SAS v9.2+(Cary, NC) or R v2.15+(Vienna, Austria).

Example 8

A follow-up clinical study enrolls newly diagnosed melanoma patients, and patients are treated and assessed as discussed in Example 7, except that the dose of S-equol is increased to 150 mg twice daily. Treatment with S-equol is for 10-21 days. Ki67 is analyzed as described in Example 7.

Example 9

Figure 3:
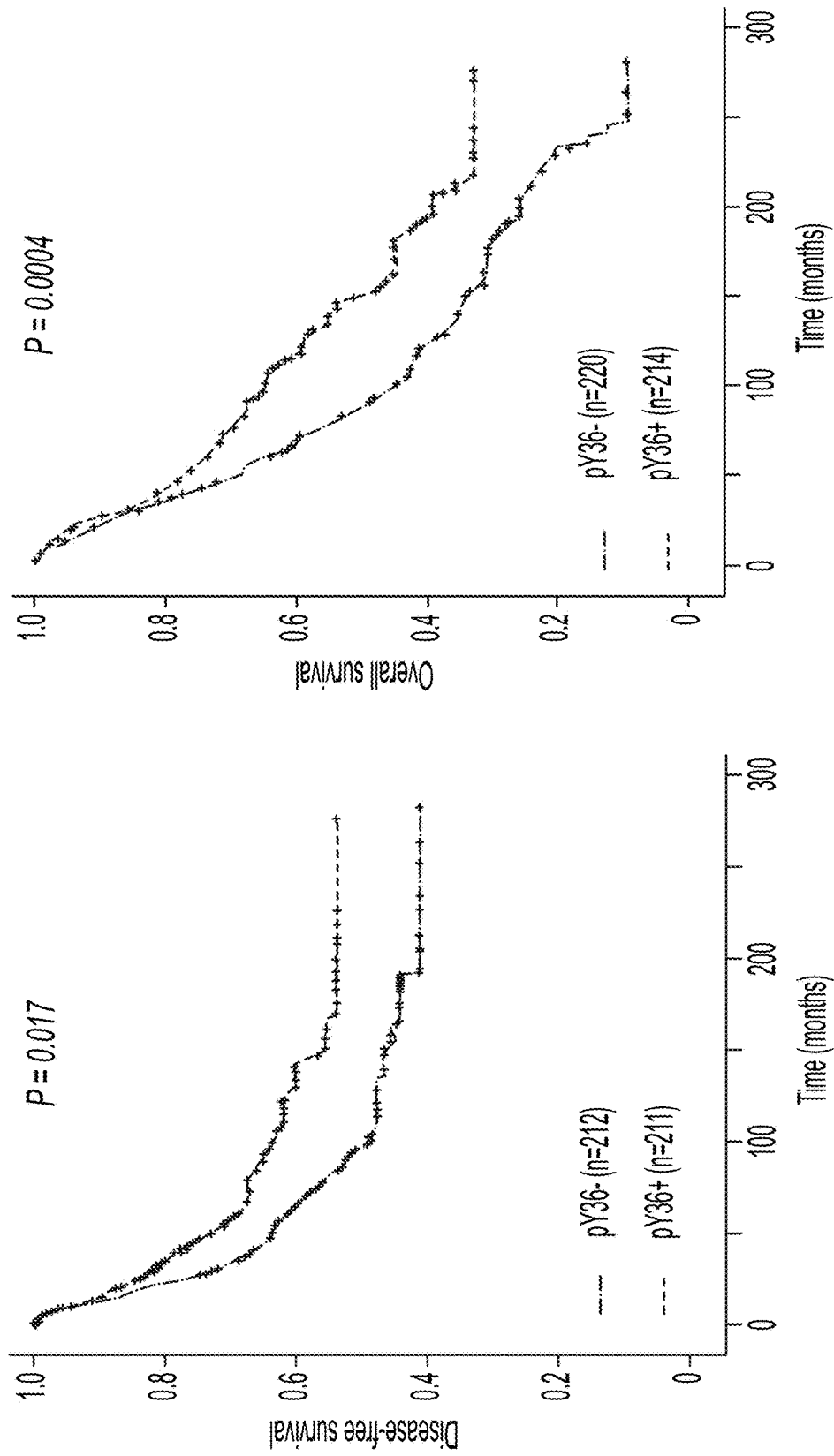
FIG. 3. Association of pY36 with disease outcomes in breast cancer.
Figure 3:
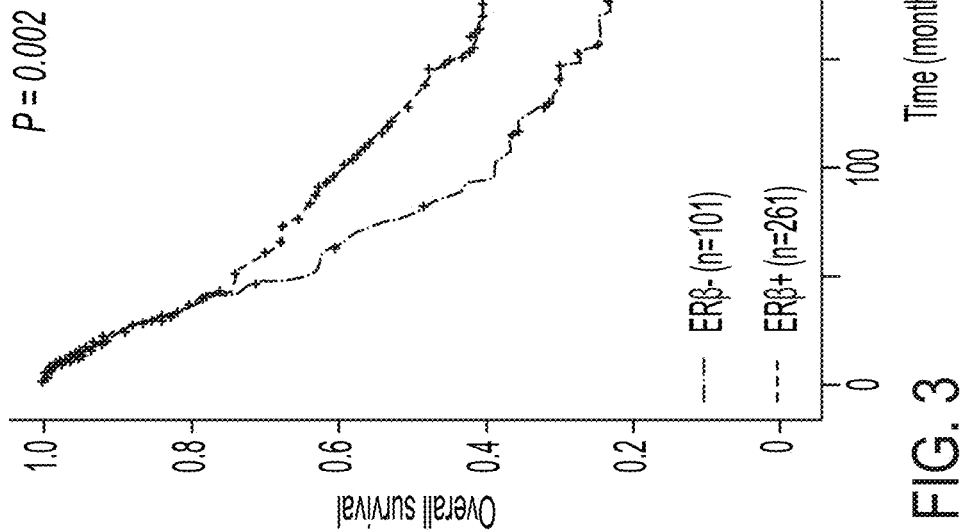
Figure 3:
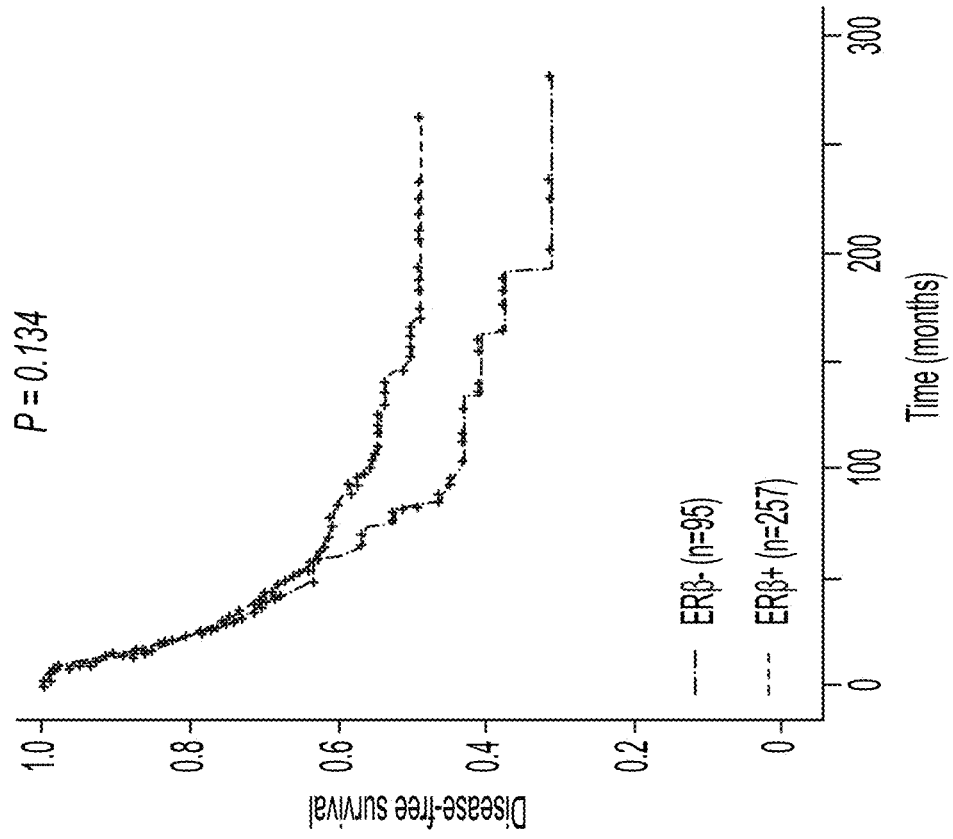

The following three murine mammary tumor lines were tested to determine the effects of a PD-1 inhibitor, S-equol and a combination of the two therapies on tumor growth: (1) E0771 (B6 background), (2) AT-3 (B6 background), and (3) 4T1 (BalbC background). This experimental design includes four arms (using AT-3 as an example): (1) controls, (2) αPD-1, (3) S-equol, and (4) αPD-1+S-equol (FIG. 3) by injecting into mice $2 \times 10^5$ cells subcutaneously into the $4^{th}$ mammary gland fat pad. Antibodies were administered α-PD-1: 200 μg/mice by i.p. injection every 3 days and S-equol was administered at 50 mg/kg/day by oral gavage. Treatment began 7 day after tumor challenge. Tumor growth trajectories were compared within treated mice using a repeated measures linear mixed model. The primary outcome was the logarithm of the tumor size, and the test statistic is the treatment×time interaction. Tumors were measured about 10 times. The number of recipient mice use used in the studies (n=8 per group) was based on the above study. Results (FIGS. 12-15) from this experiment demonstrate the ability of S-equol to boost anticancer immunotherapy.

Example 10

In addition to measurements of tumor size and weight in each arm, immunophenotyping was performed to gain more mechanistic insight into the antitumor effects of mono- and combinational therapies. Tumors, spleens, and draining lymph nodes were harvested and weighed. Anti-coagulated blood was collected by cardiac puncture. Tumors were paraffin-embedded for immunohistochemistry and snap-frozen for mRNA and protein analysis by Luminex. Flow cytometry was used (for phenotype/functions) and ViCell (for quantification) to analyze immune cells from tumor infiltrates, tumor-draining lymph nodes, and spleens. Analyses include CD3$^+$ total T cells and CD4$^+$ and CD8$^+$ T cell subsets; effector function (e.g., IFN-γ, TNF-α, IL-2, perforin, CD107a); activation (e.g., CD69, CD44, CD62L); and exhaustion (e.g., PD-1, Tim3, Lag3). Antigen-presenting cells (CD11b$^+$CD1c$^-$ monocyte/macrophages, CD11b$^+$CD11c+ dendritic cells), NK1.1$^+$NKp46$^+$ NK cells, regulatory T cells (Treg, CD3$^+$CD4$^+$CD25$^{hi}$Foxp3$^+$), and myeloid-derived suppressor cells (MDSC, CD11b$^+$Gr-1$^{hi}$) were also analyzed. CD8$^+$ T cell receptor diversity were assessed with a commercial kit (Adaptive Biotechnologies). Local cell proliferation was also tested with Ki67 and BrdU stain.

Example 11

Figures 16, 17:
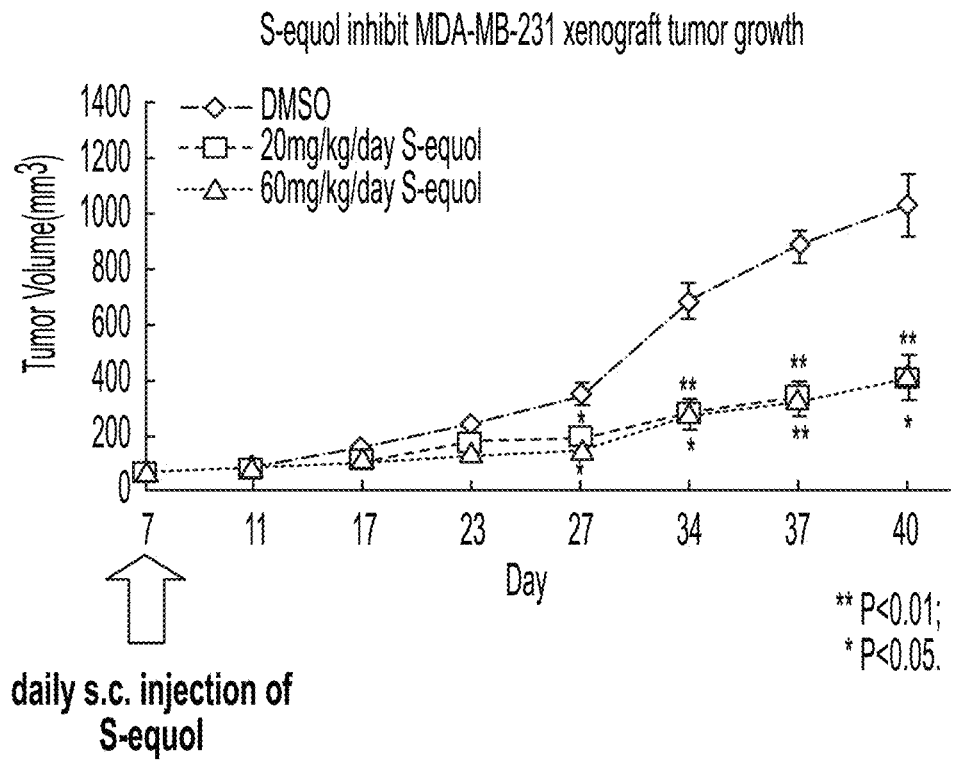
FIG. 16. S-equol stimulates pY36 and inhibits tumor growth in vivo.
FIG. 17. Results from pilot clinical study (Example 12 below).
Figure 20:
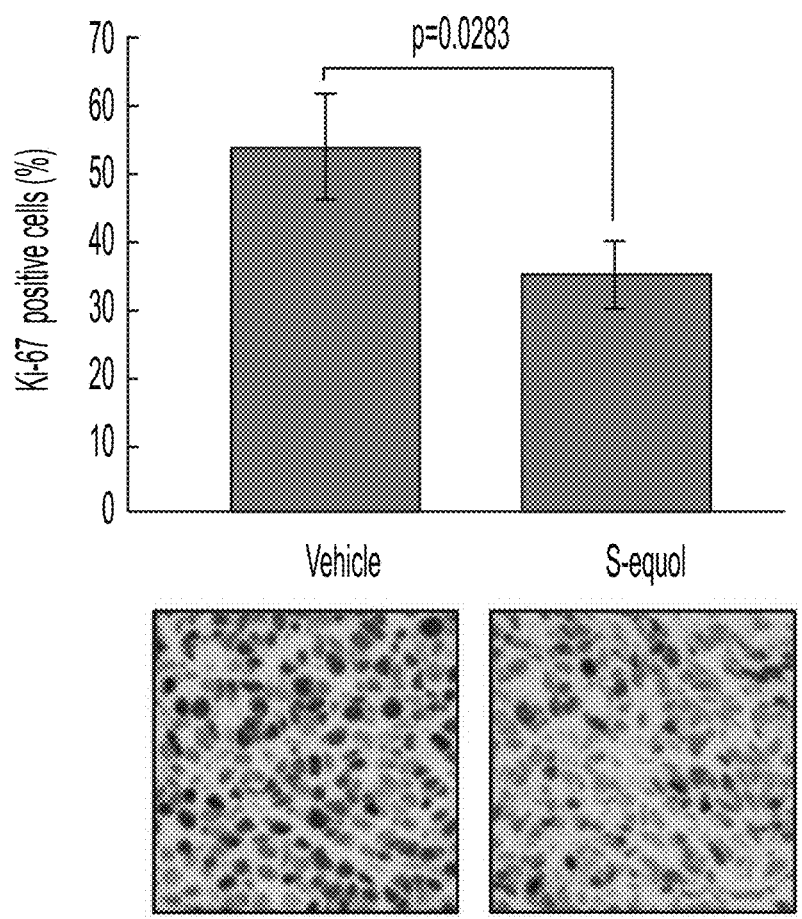
FIG. 20. S-equol reduces the growth of TNBC cells in a xenograft mouse model.

Further work in a preclinical animal model supports the notion of using S-equol to treat TNBC breast cancer. In immunocompromised mouse xenograft experiments, which used MDA-MB-231, a human TNBC breast cancer cell line, growth of tumors was suppressed by 60% with S-equol treatment compared to control. $5 \times 10^6$ MDA-MB-231 cells were injected orthotopically into mammary gland fat pads of 6 week-old female athymic nude mice (Harlan). When the tumor masses reached 50 to 80 mm$^3$ (about one week after the inoculation), the mice were given daily subcutaneous injections of S-equol (20 or 60 mg/kg per day) or PBS as a vehicle control. Tumor development was followed by caliper measurements along two orthogonal axes: length (L) and width (W) and volume (V) was estimated by the formula $V=[L \times (W^2)]/2$. Xenograft tumors harvested from mice were fixed in 10% neutral-buffered formalin, dehydrated, embedded in paraffin, and sectioned at 3 μm thickness. Representative tumor sections from vehicle control and S-equol-treated mice were tested for Ki-67 expression to assess cell proliferation, and for ERβ (3 pY36. Statistical significance in the experiments was assessed by two-tailed Student's t test. In all assays, p<0.05 was considered statistically significant. The results of these experiments are shown in FIGS. 16 and 20. See, Yuan et al. 2016 listed below, which is incorporated by reference herein for all purposes.

Example 12

Figure 18:
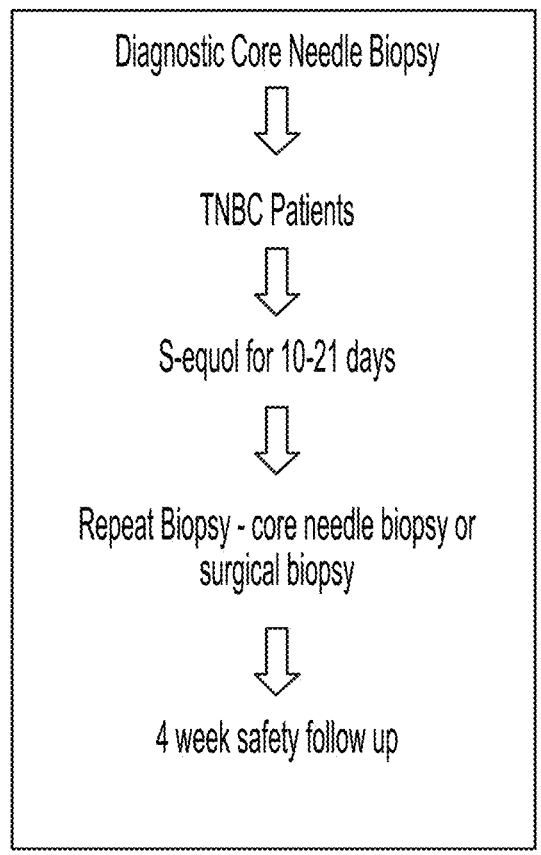
FIG. 18. Schematic for human clinical trial with S-equol.
Figure 19:
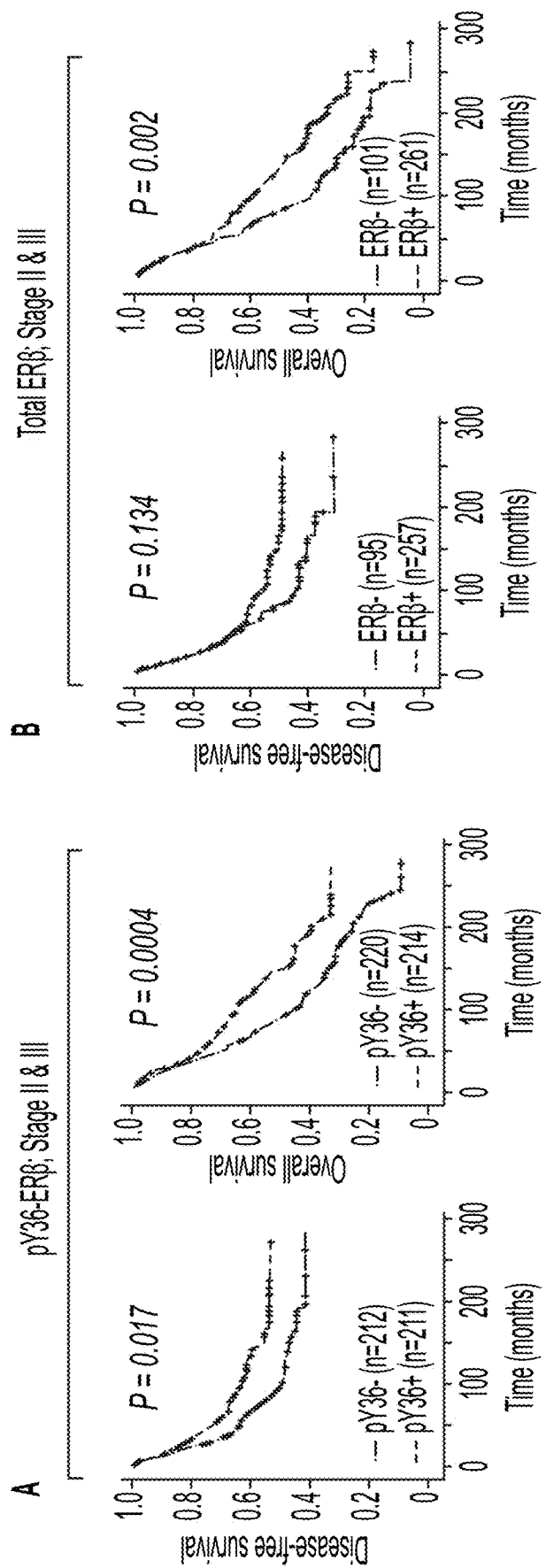
FIG. 19. Association of pY36 with disease outcomes in breast cancer.

A pilot biomarker clinical study was performed in 20 subjects with documented TNBC to determine the effect of the ERβ agonist S-equol on Ki67 an indicator of tumor cell proliferation. Tumor cell proliferation was measured by immunohistological staining for Ki-67. See, FIG. 18 for the outline of the protocol. Ki-67 is encoded by the gene MKI67 gene and is required to maintain individual mitotic chromosomes dispersed in the cytoplasm following nuclear envelope disassembly. Measuring the fraction of Ki-67-positive cells in a tumor is known to be a reliable parameter for assessing cancer patient prognosis. Subjects with TNBC are known to have very high levels of Ki67.

Patients enrolled in the study received a history, physical, laboratory assessment, radiological imaging, and diagnostic biopsies. Immunohistochemistry (IHC) of Ki67 (proliferation marker), total ERβ, and pY36-ERβ (phosphorylated ERβ, B7H1 (also known as PDL-1) and BRCA1 (breast cancer 1, early onset) were conducted using core needle biopsy tissue samples prior to treatment. Patients were given oral S-equol 50 mg, twice daily for approximately two weeks (10-21 days) prior to the scheduled oncologic surgeries or start of primary systemic therapy. Tumor samples were obtained from the surgery or the two-week repeat core needle biopsy. Post-treatment IHC evaluation of Ki67, total ERβ, phosphorylated ERβ (pY36) and BRCA1 were obtained. Ki67 reduction is a validated surrogate marker of both short and long term hormonal therapy efficacy in trials of human breast cancer and was compared pre- and post-treatment with S-equol. S-equol caused a measurable decrease in Ki67, indicating its efficacy in this tumor type. A c-DNA microarray platform was also used to discover downstream transcriptional targets of ERβ resulting from activation by S-equol.

Women eligible for the study had newly diagnosed, previously untreated, triple negative breast cancer, with an intact primary breast tumor of any size. All stages of the disease were eligible. They took S-equol during the time they underwent standard preoperative evaluation or pre-therapeutic work-up for advanced disease, such as staging procedures or central line placement. If primary surgery was performed, tissue leftover after standard diagnostic evaluation was used for the two-week biomarker assessment. If the patient did not have primary surgery at the end of the two-week S-equol treatment, a second set of 14-gauge core needle biopsies was obtained before the start of any standard systemic therapy. See, FIG. 10.

A standard procedure for acquiring core biopsy with a Bard 14-gauge needle was utilized for determining TNBC prior to enrollment. Whenever possible, the tumor tissues used for IHC analyses were acquired at the same time as the diagnostic core biopsy. The tissue samples were sent for staining of total and pY36 ERβ and Ki67, and analyzed. Testing for ERα, PR, and HER-2 was performed using validated methods. TNBC tumors were defined as less than 5% nuclear staining of carcinoma cells for ERα and PR and either 0, 1, or 2+ staining for HER-2 by IHC. Whole-Genome DASL HT platform from Illumina, which is designed for gene expression profiling with extremely low input of RNA (50 pg), was used to interrogate paired FFPE tissue obtained before and after exposure to S-equol.

Statistical analysis was conducted which showed that ERβ-expressing TNBC responds to S-equol as manifested by measurable decline in Ki67. The primary analysis estimated the geometric mean change of the Ki67 expression from baseline to two weeks. This was performed using a one-sample t-test of the pre/post differences in the log-transformed data, and summarized by the 95% confidence interval. According to the IMPACT trial, the changes in the geometric mean of Ki67 expression after two weeks were −76, −59.5, and −63.9% for the anastrazole, tamoxifen, and combination groups respectively, with a standard deviation of approximately 1.0 on the log-scale. This implies effect sizes of 1.0 to 1.5 and a power >90% for testing for a decrease in Ki67 expression with two-sided $\alpha=0.05$ and a sample size of at least 45 patients accounting for variation in accrual and potential drop out. All computations were performed with SAS v9.2+(Cary, NC) or R v2.15+(Vienna, Austria). 20 patients enrolled and completed the study. 17 patients had evaluable pre- and post-treatment samples. Of these 17 evaluable patients, 4 patients had greater than 30% reduction in Ki-67, one patient had greater than 20% reduction, and 7 patients had 0-20% reduction (5 patients had no reduction in Ki-67). See, FIG. 17.

Example 13

A follow-up clinical study enrolls 25 newly diagnosed TNBC patients, and patients are treated and assessed as discussed in Example 12, except that the dose of S-equol is increased to 150 mg twice daily. Treatment with S-equol is for 10-21 days. Ki67 is analyzed as described in Example 12.

Example 14

Background: The non-overlapping functions of the two estrogen receptor subtypes, ERα and ERβ, in tumor cells have been studied extensively. However, their counterparts in host cells is vastly under-interrogated. Even less is known about how ERα and ERβ activities are regulated in a subtype-specific manner. A phosphotyrosine residue (pY36) of human ERβ was previously identified that is important for tumor ERβ to inhibit growth of breast cancer cells in vitro and in vivo. A role of this ERβ phosphotyrosine switch in regulating host ERβ previously remained unclear.

Methods: Conventional gene editing was used to mutate the corresponding tyrosine residue of endogenous mouse ERβ(Y55F) in mouse embryonic stem cells. The derived homozygous mutant Esr2Y55F/Y55F mouse strain and its wild-type (WT) counterpart were compared in various transplant tumor models for their ability to support tumor growth. In addition, flow cytometry-based immunophenotyping was carried out to assess anti-tumor immunity of WT and mutant hosts. Adoptive transfer of bone marrow and purified CD8+ T cells were performed to identify the host cell type that harbors ERβ-dependent antitumor function. Furthermore, cell signaling assays were conducted to compare T cell receptor (TCR)—initiated signaling cascade in CD8+ T cells of WT and mutant mice. Lastly, the ERβ-selective agonist S-equol was evaluated for its efficacy to boost immune checkpoint blockade (ICB)-based anticancer immunotherapy.

Results: Disabling the ERβ-specific phosphotyrosine switch in tumor-bearing hosts exacerbates tumor growth. Further, a cell-autonomous ERβ function was defined in CD8+effector T cells. Mechanistically, TCR activation triggers ERβ phosphorylation, which in turn augments downstream TCR signaling cascade. S-equol, a clinically safe ERβ-selective agonist, facilitates TCR activation stimulates the ERβ phosphotyrosine switch and boosts anti-PD-1 ICB immunotherapy.

Conclusion: This mouse genetic study clearly demonstrates a role of the ERβ phosphotyrosine switch in regulating ERβ-dependent antitumor immunity in CD8+ T cells. These findings inform the development of novel combination therapies through galvanizing the previously unappreciated immune-enhancing function of ERβ.

Abbreviations: ER: estrogen receptor; TILs: Tumor infiltrating lymphocytes; PD-1: programmed cell death protein 1; CD8: cluster of differentiation 8; TCR: T-Cell Recept\or; ICB: immune checkpoint blockade.

ERα and ERβ, which are encoded by different genes (ESR1 and ESR2), mediate the diverse physiological effects of estrogens (Katzenellenbogen 2000; McDonnell 2002; Heldring 2007; Deroo 2006; Thomas 2011). Despite sequence homology and similar transcriptional activity, these two ER subtypes exert distinct and even opposite biological functions in cancer (Katzenellenbogen 2000; Deroo 2006; Thomas 2011). ERα is best known for its role in supporting estrogen-dependent breast tumor growth, whereas ERβ has an antitumor activity in multiple cancer types including breast, prostate, colorectal and ovarian cancers, melanoma, and glioma (Fan 2010; Sareddy 2012; Mak 2006; Nanni 2009; Nakajima 2011; Leung 2011). Research on tumor-related functions of ERα and ERβ has been primarily focused on their tumor-intrinsic activities in regulation of cancer cell behaviors including tumor cell proliferation and invasion. However, emerging evidence suggests that they also play important roles in host cells during cancer development and progression (Fan 2010; Sareddy 2012; Mak 2006; Nanni 2009; Nakajima 2011; Leung 2011). For example, tumor-extrinsic ERα is implicated in enhancing the immunosuppressive activity of myeloid derived suppressor cells (MDSC) during ovarian cancer progression (Svoronos 2016). In support of a tumor extrinsic antitumor activity of ERβ, syngeneic murine melanoma cells grafted to recipient ERβ-KO animals grew more robustly than those in WT recipient mice (Cho 2010). More recent studies implicate ERβ in promotion of antitumor immunity (Huang, 2020; Zhao, 2018). However, how tumor-extrinsic activity of ERβ is regulated in an ER subtype-specific manner remained unclear.

The selective biological effects of ERα and ERβ partly result from their intrinsic differences in protein structure and transcriptional activity. Although the two ER subtypes share a highly homologous central DNA binding domain (DBD) and carboxyl-terminal ligand-binding domain (LBD) in the activation function domain 2 (AF2), the more divergent amino-terminal sequence in activation function 1 (AF1) domain has been linked to subtype-specific activity (Smith 2004; Madak-Erdogan 2013). In support, previous work identified a subtype-specific phosphotyrosine residue in human ERβ AF1 (Y36) that regulates its tumor-intrinsic antitumor activity (Yuan 2014).

In a canonical mode, both ERα and ERβ activate transcription upon direct binding to the estrogen response element (ERE) or being tethered by other site-specific transcription factors to their cognate target gene loci. In addition to the nuclear function in transcription activation ('genomic action'), membrane-associated ERα can elicit rapid signaling events in the cytoplasm within minutes of cellular exposure to extracellular cues such as growth hormones (Bjornstrom, 2005). The latter function of ERα, which is called 'non-genomic action', is distinct from and independent of its canonical transcription activity. It is currently unknown whether a similar non-genomic mechanism is used by ERβ to exert its antitumor activity.

In the present study, a genetically engineered mouse model was established in which the human Y36-equivalent phosphotyrosine residue of mouse ERβ is mutated to phenylalanine (F55F). Tumors of various types grew significantly faster in ERβ mutant hosts versus WT control. By adoptive transfer of bone marrow and purified immune cells, these studies show that ERβ signaling in CD8+ immune cells harbors the antitumor function of host ERβ. The studies further show that tyrosine phosphorylation of ERβ is stimulated upon TCR activation, which in turn enhances downstream signaling cascade required for effector T cell activation likely via a non-genomic action of ERβ. Lastly, the translational utility of rallying ERβ signaling in antitumor immunity was explored by combining the ERβ-selective agonist S-equol with anti-PD-1 ICB immunotherapy.

Methods

Animals

All animal experiments were approved by the Institutional Animal Care and Use Committee (IACUC) of the University of Texas Health San Antonio and the George Washington University. All mice had water ad libitum and were fed regular chow. Rag1−/−131, BALB/C, and CD45.1 congenic mice were purchased from the Jackson Laboratory. Mouse ES clones harboring an ERβ tyrosine-to-phenylalanine (Y55F) mutation were obtained by homologous recombination. The targeting vector containing this mutation was introduced via electroporation into the C57BL/6 ES cells. The transfected cells were subjected to neomycin selection, and DNA samples from survived clones were analyzed by Southern blotting to identify the correct homologous recombinants. ERβY55F mutant mice were generated from the mutant ES cell clone and then crossed with Flpo-Cre mouse to remove the neo marker in vivo. Littermate WT and homozygous (Esr2 Y55F/Y55F140) mutant knock-in (KI) mice in the pure C57BL/6 background were generated by intercrossing of heterozygous Esr2+/Y55F 141 mice. Littermates of 6-8 weeks of age were used in the experiments. Mice were maintained in a specific pathogen-free facility in accordance with American Association for Laboratory Animal Science guidelines. Littermate animals from different cages were randomly assigned into the experimental groups, which were either co-housed or systematically exposed to other groups' bedding to ensure equal exposure to all group's microbiota.

Cell Lines and Culture Conditions

HEK293T, MC38 colon adenocarcinoma cells, B16F10 melanoma 149 and EMT-6 mammary tumor cells were purchased from ATCC. E0771 mammary tumor cells were purchased from CH3 Biosystems (Cat: 940001). M-Wnt mammary tumor cells were a gift from Dr. Steven Hursting, University of North Carolina. AT-3 mammary tumor cells were generated by Dr. Scott Abrams's lab at the Roswell Park Comprehensive Cancer Center. ID8agg-Luc was generated by Dr. Tyler Curiel's lab. All cell lines were free of mycoplasma and cultured in high glucose DMEM (Thermo Fisher Scientific; Cat: #11965) supplemented with 10% heat-inactivated fetal bovine serum (FBS), 1% L-glutamine, 100 µg/ml penicillin and 100 µg/ml streptomycin (P/S, Thermo Fisher Scientific, Cat: #15140122).

In Vivo Tumor Challenges, Treatment, and Assessment

For tumor studies, 8 to 10-week-old mice were used. M-Wnt (5 Å~105 cells), E0771 (5 Å~105 cells), AT-3 (2 Å~105 cells), and EMT-6 (5 Å~105 cells) tumor cells were subcutaneously inoculated into the fourth mammary pad. B16F10 (0.5 Å~106 cells) and MC38 (5 Å~106 cells) tumor cells were subcutaneously inoculated into the back flank. Tumor volume was measured with calipers (0.5 Å~length Å~width2) on the indicated days. Anti-IgG2a (BioXcell, Cat: #BE0146) and anti-PD-1 (BioXcell, Cat: #BE0089) antibodies were administered through intraperitoneal (i.p.) injection at a dose of 100 µg/mouse every 3 days starting on day 7 after tumor challenge for the duration as indicated. S-equol (from Ausio Pharmaceuticals) was administered daily by oral gavage at 50 mg/kg beginning on the day of tumor challenge and continuing throughout the entire tumor growth experiments.

Bone Marrow Chimeras

WT C57BL/6 (CD45.1) recipient males or females (10 mice per transplantation 172 group) were irradiated with 9.5 Gy total body irradiation (TBI). Pooled tibial and femoral bone marrow cells from donor WT (CD45.2) or KI (CD45.2) C57BL/6 mice were lysed with RBC lysis buffer. Bone marrow cells from WT or KI mice were retro-orbitally injected into irradiated recipient WT (CD45.1) mice (1 Å~107 cells per each recipient mouse). Animals were maintained on trimethoprim sulfamethoxazole (Hi-Tech Pharmacal) antibiotic water for 1 day prior and 2 weeks after irradiation, and tumor transplantation of chimeric mice was performed at least 8 weeks after reconstitution. Hematopoietic reconstitution of all animals was verified by flow cytometry of splenocytes at the end of the experiment.

Adoptive Transfer of CD8+ T Cells

Total spleen cell suspensions were prepared from 6 to 8-week-old WT and KI male mice. CD8+ T cells were isolated from splenocytes by using EasySep™ Mouse CD8a Positive Selection Kit II (Stemcell Technologies, Catalog #18953). Enriched naïve CD8+ T cells were adoptively transferred by intravenous injection (2 Å~106 cells) into Rag1−/−187 recipients. B16F10 (0.5 Å~106 cells) melanoma cells were subcutaneously inoculated into the back flank on the following day.

Flow Cytometry

Cells were stained and sorted as previously described (Clark, 2016), using LSR II and FACSAria hardware and analyzed by FACSDiva (BD Bioscience) and FlowJo software (FlowJo, LLC). CD8+ T cell isolation and in vitro activationCD8+ T cells were isolated from the spleens under aseptic conditions. Individual spleens were homogenized to release splenocytes. Cell suspension in 5 ml RPMI 1640 medium was centrifuged (5 min at 300 g at room temperature), supernatant decanted and cell pellet resuspended in the residual volume (approximately 100 µl). Erythrocytes were lysed briefly in 900 µl sterile water (1-2 s) before the addition of 100 µl 10 Å~PBS to restore iso-osmolarity and 5 ml serum-free RPMI1640 medium. Single-cell suspensions from individual spleens were pooled, filtered through 70 µm and 40 µm cell strainer (Fisher) and counted. CD8+ T cells were isolated using magnetic cell sorting by negative selection (MagniSort™ Mouse CD8 T cell Enrichment Kit, Invitrogen) according to the manufacturer's instructions. Isolated 2 Å~106 CD8+ T cells were plated into 24-well plates (Nunc, Thermo Fisher Scientific), which had been pretreated with 10 µg/ml anti-CD3 (clone 145-2C11, Bio X Cell) and 1 µg/ml anti-CD28 (clone 37.51, Bio X Cell) in PBS overnight at 4° C. and washed twice with PBS prior to cell plating.

Quantitative RT-PCR

Total RNA was isolated from homogenized whole lung tissue using RNeasy (Qiagen). cDNA was synthesized with 1 µg of total RNA using the ImPromII Reverse Transcription System (Promega) and random primers. Quantitative PCR (qPCR) was conducted using the 7900HT Real-Time PCR System (Applied Biosystems), amplified with transcript-specific primers with SYBRGreen (Thermo Scientific), according to manufacturer's instructions. Pimer sequences were described previously (Clark, 2016).

Immunoblotting

Isolated mouse spleen and bone marrow were lysed in RIPA Lysis and 218 Extraction Buffer. Protein amounts were determined by using Pierce BCA Protein Assay Kits (Pierce, Cat: #23225). Primary antibodies were against ERβ mouse mAb (Thermo Fisher, Catalog #MA5-24807), Zap70 (CST, #3165), p-Zap70 (Tyr319)/Syk (Tyr352) (CST, #2717), LAT (CST, #45533), p-LAT (Tyr220) (CST, #20172), Lck (CST, #2752), p-Lck (Tyr505) (CST, #2751), α-Tubulin (CST, #3873). Corresponding secondary antibodies were used. Proteins were detected with ECL SuperSignal™ West Pico PLUS Chemiluminescent Substrate (Thermo Fisher, Cat. #34580).

TCGA Data Analysis

For assessing the association of ESR2 expression with patient survival, patient vital status was ESR2 expression level versus T cell infiltration in each tumor, the total expression of CD4, CD8α, GZMB (log 2 counts per million) was used to assess the infiltration of cytotoxic T-lymphocytes, and correlations were computed versus ESR2 expression. Correlation of ESR2 expression levels with survival of breast cancer patients is calculated by the level of CD8+ T cell infiltration. All patients in the TCGA breast cancer study were divided according to the expression level of ESR2 (higher or lower than mean expression value of all patients). The correlation of ESR2 expression level with survival is shown for patients whose tumors had higher (>1 SD) or lower (<1 SD) expression of CD8 [(CD8A+CD8B)/2](Pan, 2018; Jiang, 2018). For human melanoma tumor infiltrating lymphocytes (TILs) analysis, single cell RNA-seq dataset was downloaded from a public database (GSE72056). Activated CD8+ TILs (CD8a>=5 & CD44>=2) were used for Gene Set Enrichment Analysis (GSEA) (GSEA_4.1.0 from www.gseamsigdb.org/). The enrichment of TNFα signaling and NFAT pathway were evaluated 240 in ESR2hi TILs relative to ESR2low TILs.

Statistical Analysis

Data are presented as average±S.E.M. Statistical analysis was performed using Microsoft Excel (Microsoft) or Graph-Pad Prism 7 software (GraphPad Prism Software Inc). Unpaired Student t test was used for the comparison between two groups. One-way ANOVA or two-way ANOVA analysis followed by the Bonferroni post-hoc test were used for the multiple comparisons. Repeated-measure two-way ANOVA (mixed-model) followed by the Bonferroni post-hoc test was used for the analysis of tumor growth curve. A value of p<0.05 was considered significant.

Results

Host ERβ Signaling Inhibits Tumor Growth

Figure 23:
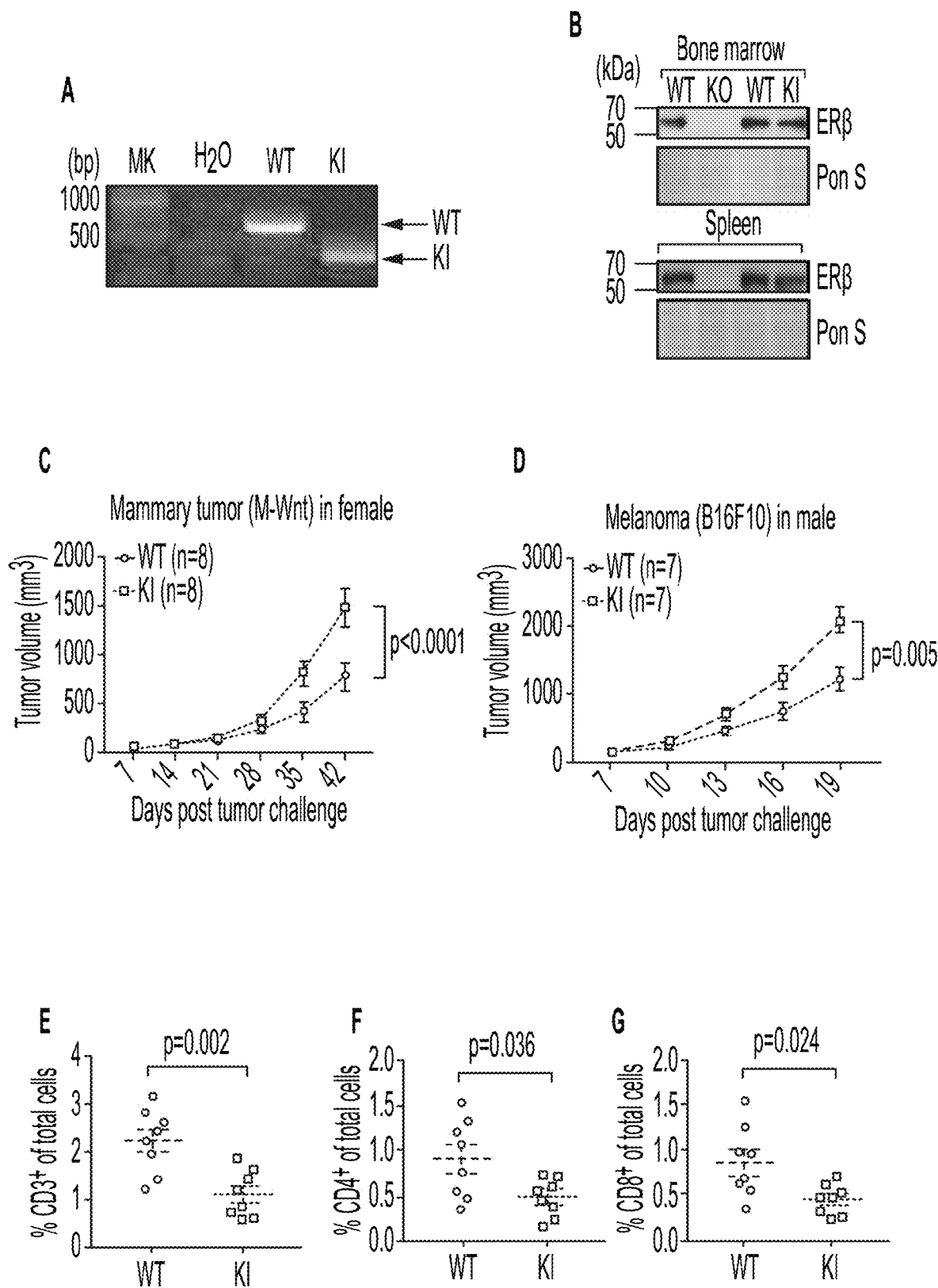
FIG. 23. The phosphotyrosine switch is important for host ERβ to inhibit tumor growth. (23A) Representative genotyping results for WT and KI allele of WT and KI mice. (23B) ERβ protein levels in mouse bone marrow and spleen (Ponceau S shown as loading control). (23C) M-Wnt mammary tumor and (23D) B16 melanoma growth in WT/KI mice. Flow cytometry of B16 melanoma-infiltrating (23E) CD3+, (23F) CD4+ and (23G) CD8+ cell percentage.
Figure 27:
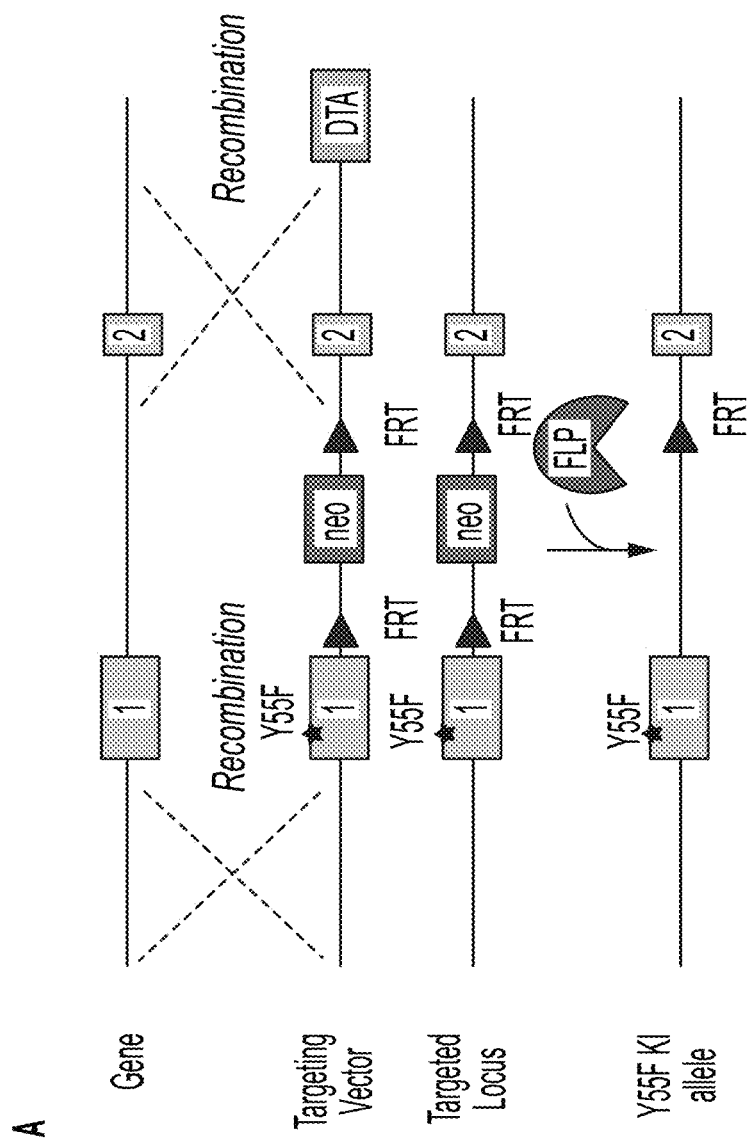
FIG. 27. Generation of ERβ Y55F knockin mice.
Figure 27:
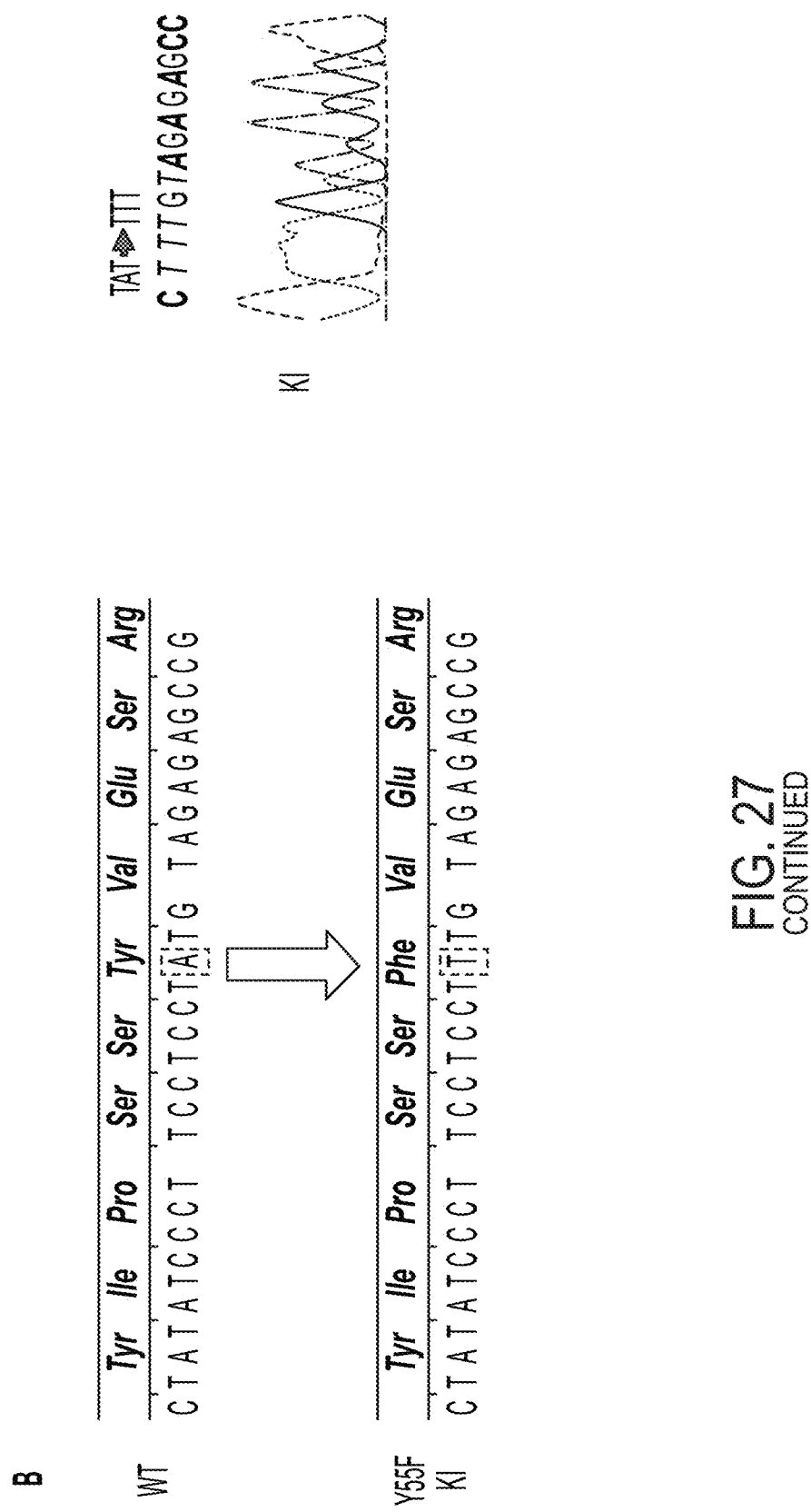
Figure 27:
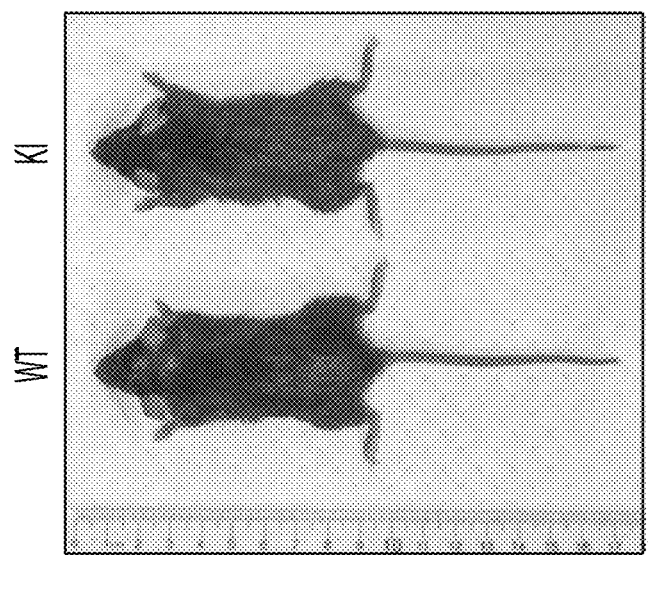

To interrogate tumor-extrinsic function of the ERβ phosphotyrosine switch, conventional homologous recombination-based gene editing approach was used to mutate the tyrosine residue Y55 of endogenous mouse ERβ, which corresponds to Y36 of human ERβ, to phenylalanine (Y55F, FIG. 27A). The correct genomic alteration at the native Esr2 locus was confirmed by PCR and sequencing (FIG. 23A, FIG. 27B). A whole-body homozygous mutant mouse strain (Esr2Y55F/Y55F259) was established in the pure C57BL/6 background and is referred to as knockin (KI) mice thereafter. Consistent with previously reported ERβ knockout (KO) mice21, KI mice had no overt developmental defects and were grossly indistinguishable from their WT littermates (FIG. 27C). Survey of ERβ expression in WT, KO, and KI mice indicated that the Y55F mutant protein was expressed at levels comparable to WT ERβ in multiple tissues including 263 bone marrow and spleen (FIG. 23B). Thus, any phenotype associated with KI mice is unlikely due to attenuated ERβ expression.

Figure 28:
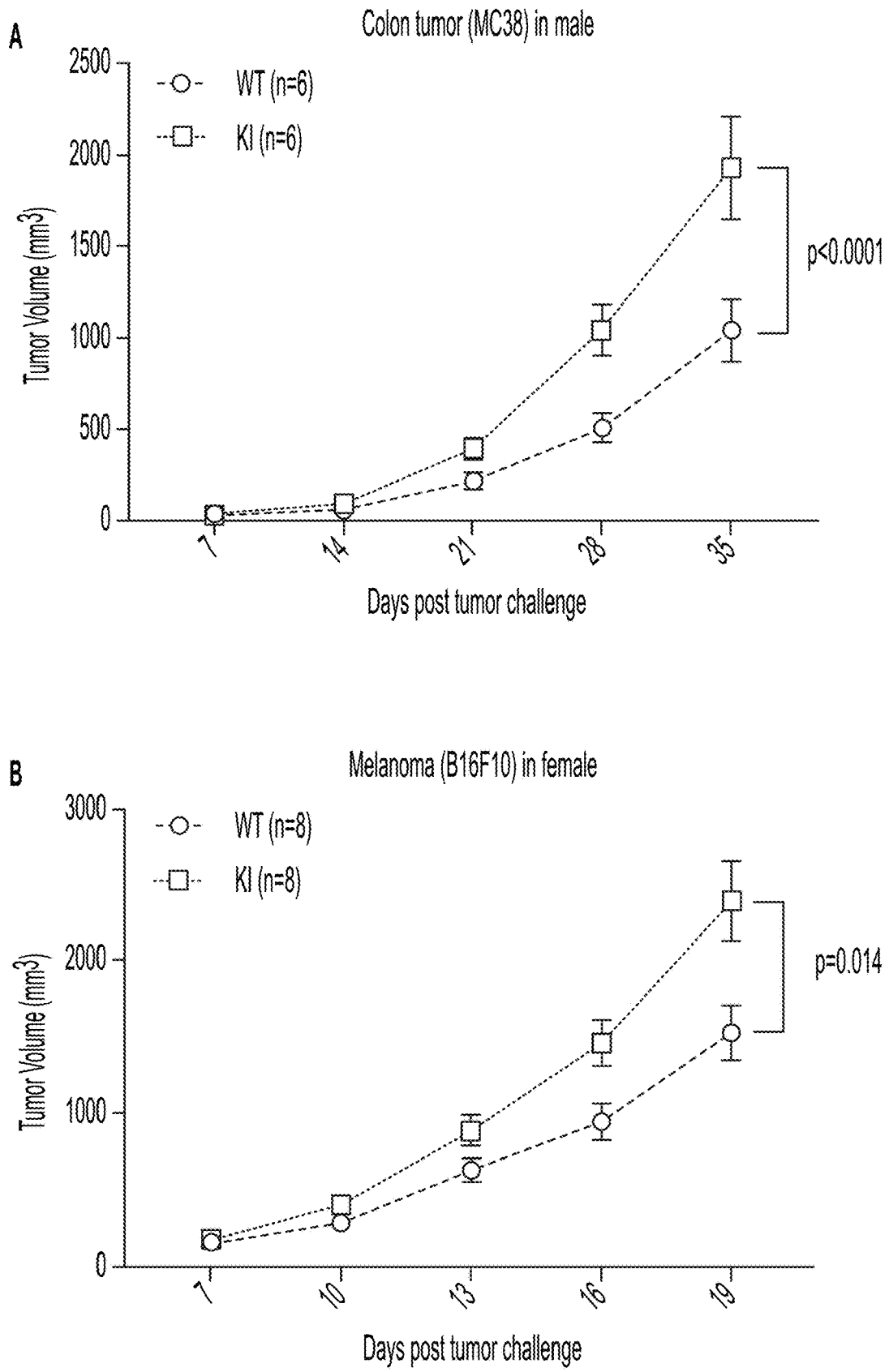
FIG. 28. The phosphotyrosine switch is important for host ERβ to inhibit tumor growth.
Figure 28:
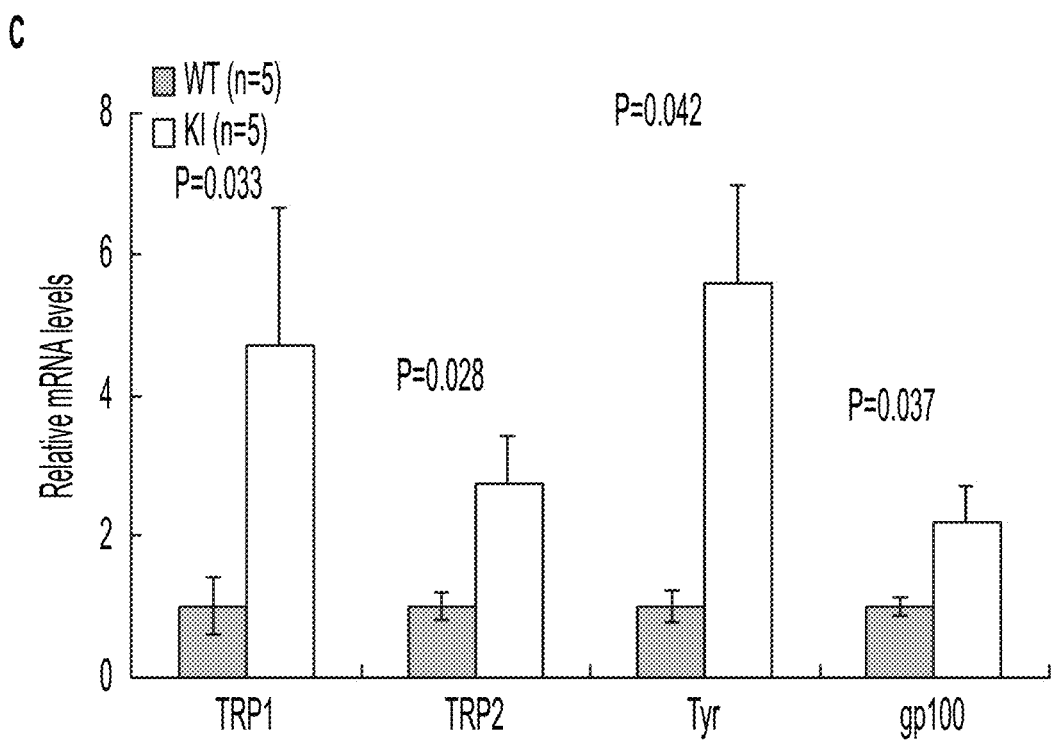
Figure 29:
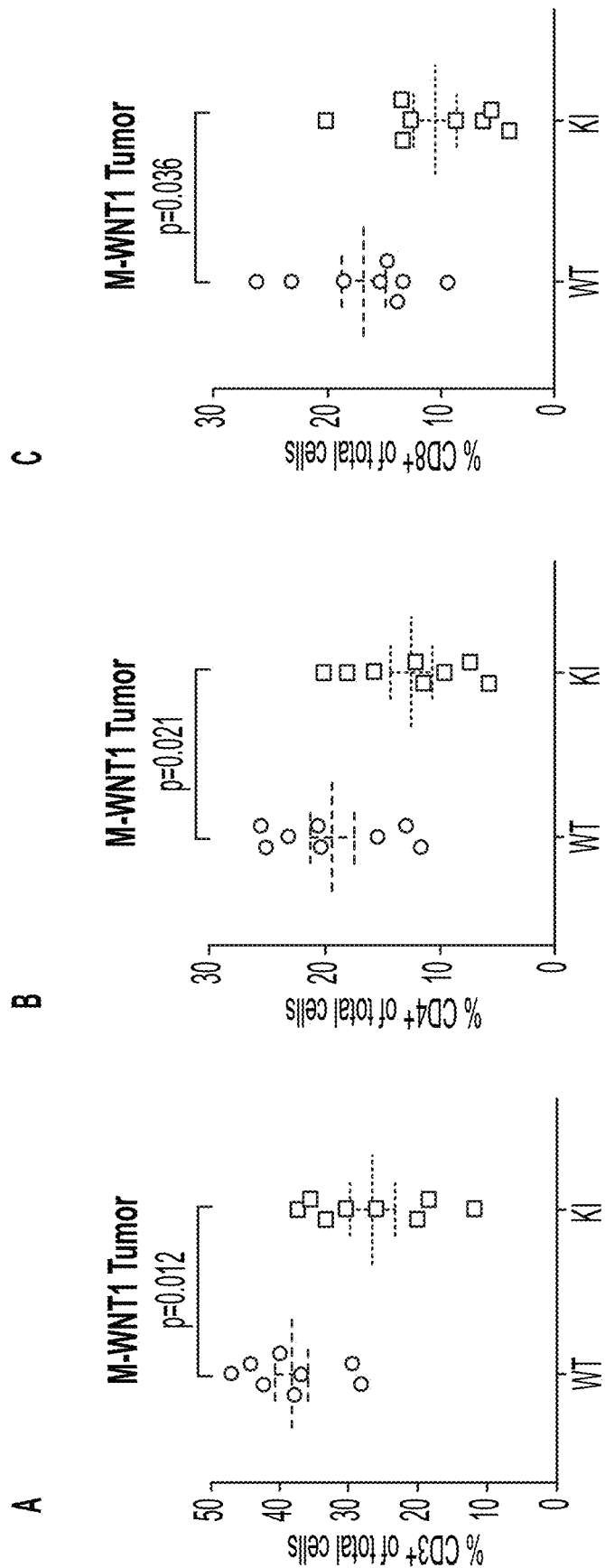
FIG. 29. Immunophenotyping analysis of tumor and TDLN from WT and KI mice.
Figure 29:
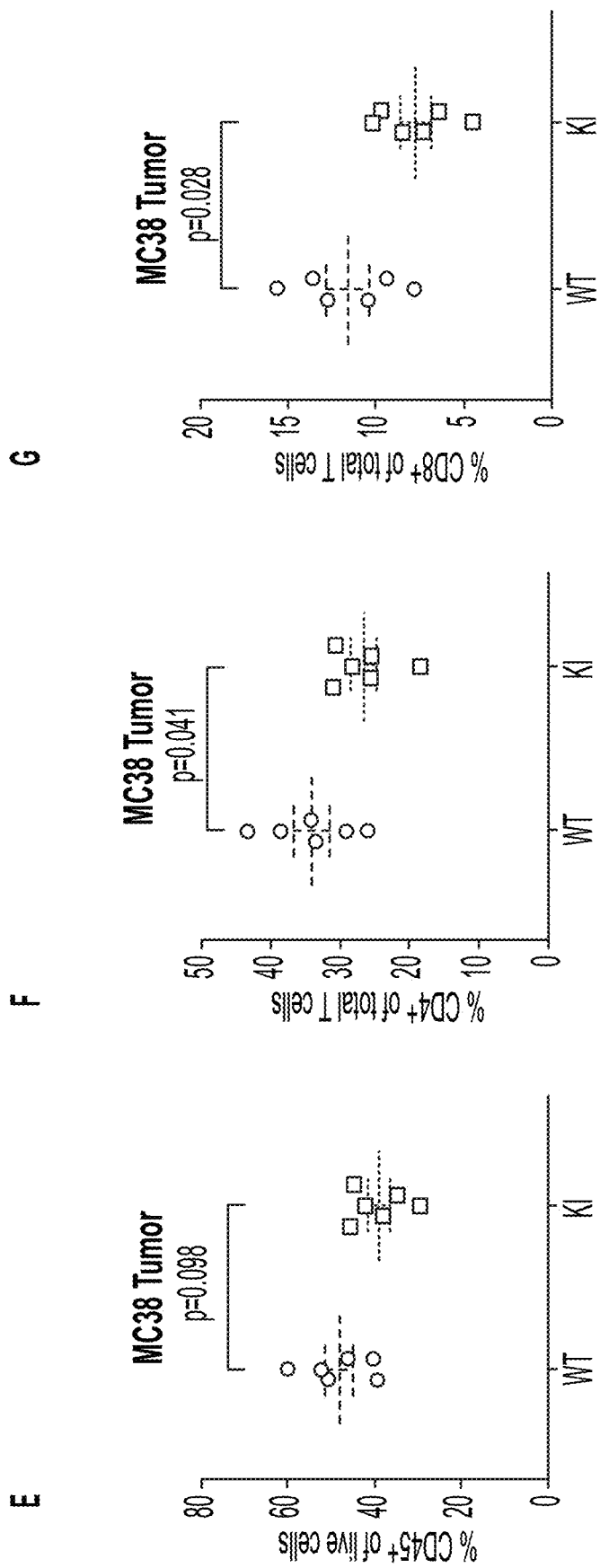
Figure 30:
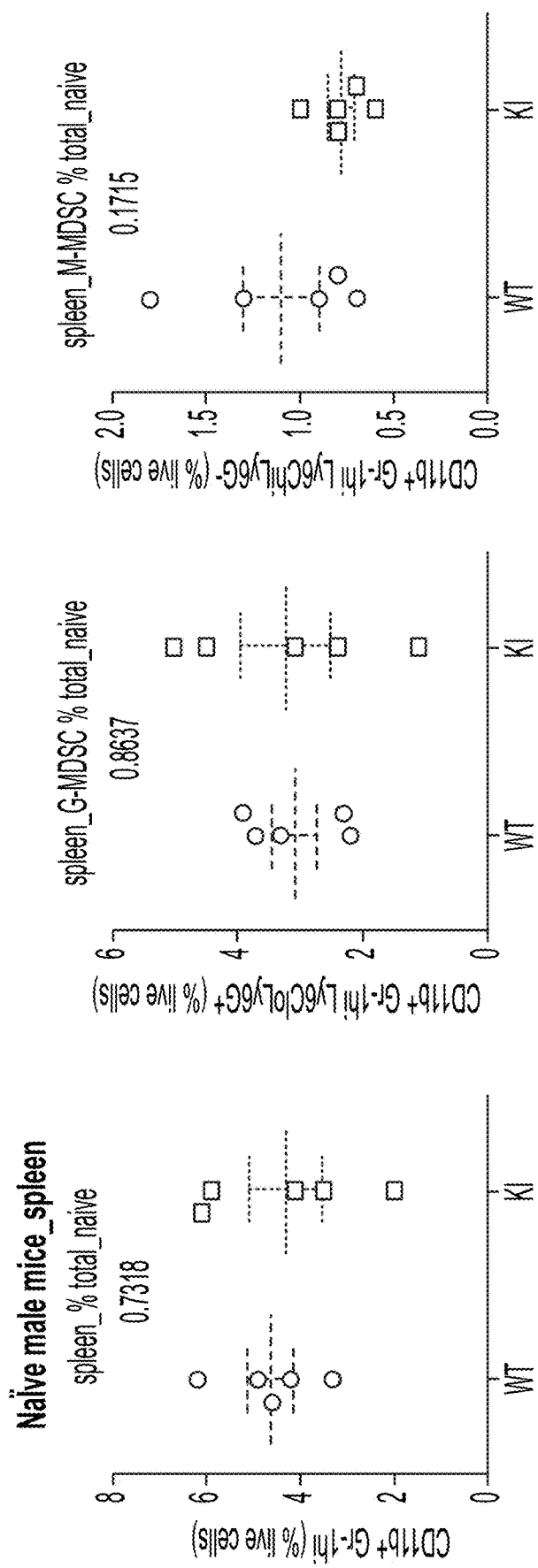
FIG. 30. ERβ signaling does not affect MDSC abundance in naïve or tumor-bearing mice.
Figure 30:
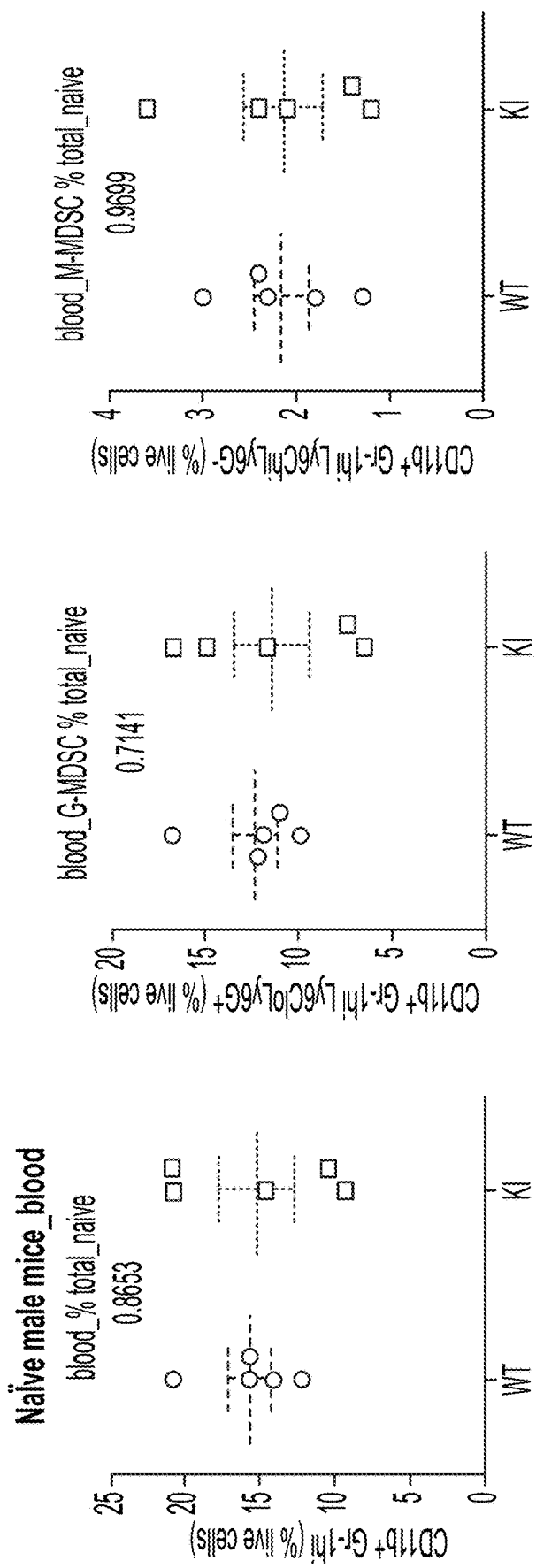
Figure 30:
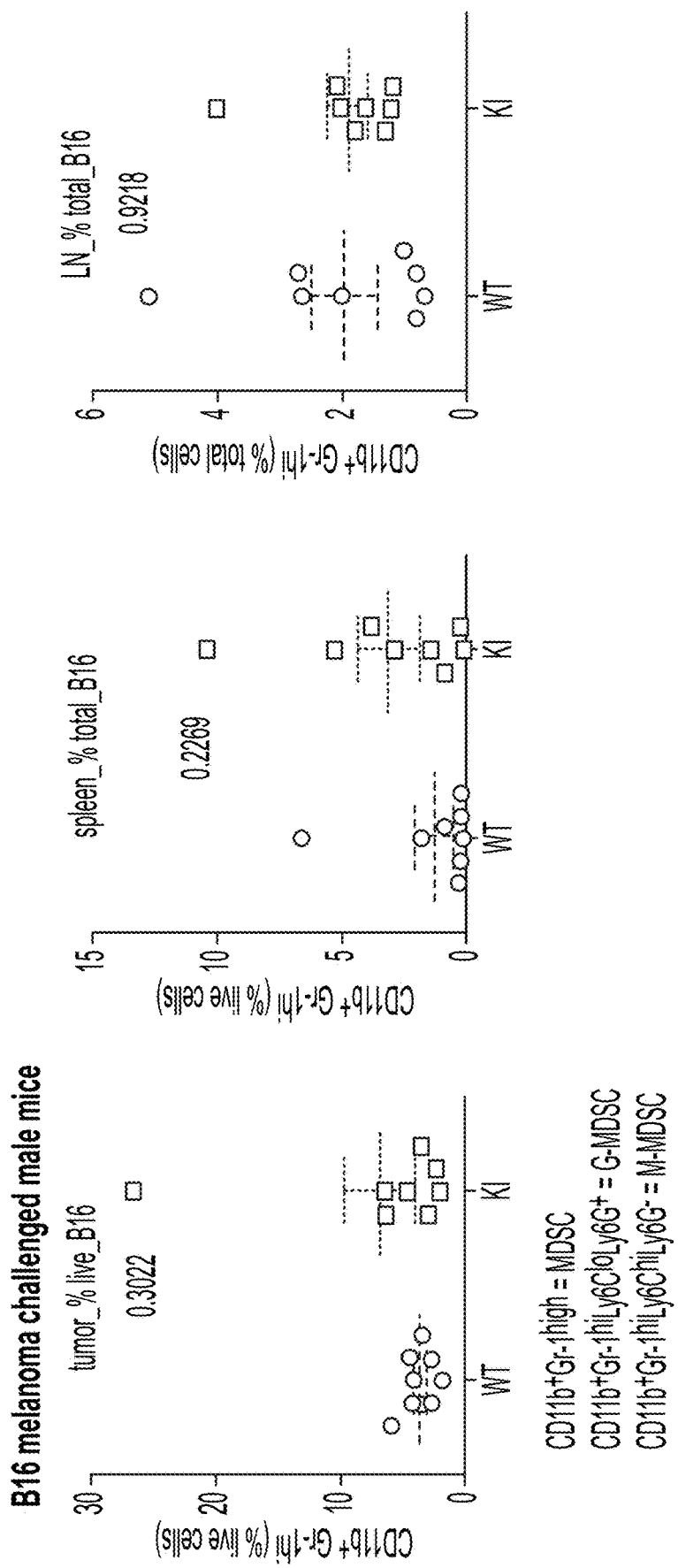

To determine the impact of host ERβ signaling on tumor growth, various syngeneic murine tumor cells, including mammary (M-Wnt-1, FIG. 23C), colorectal tumors (MC38, FIG. 28A), and melanoma (B16F10, FIG. 23D, FIG. 28B) were transplanted into WT and K1 mice. In all the tumor models tested, syngeneic tumors grew more robustly in KI recipient mice than in their WT counterparts, a trend observed in both male and female cohorts (FIG. 23D, FIG. 28B). Furthermore, melanoma-bearing KI mice also displayed more pronounced lung metastases than WT control (FIG. 28C). In concordance with more aggressive tumor growth in KI mice, immunophenotyping of tumor-infiltrating lymphocytes (TILs) indicates that abundance of total CD3+ immune cells, CD4+ helper T cells, and CD8+ effector T cells was substantially lower in tumors from KI hosts than WT control (FIG. 23E-G, FIG. 29). In contrast to the previously reported role of ERα on MDSC13, ERβ does not appear to affect MDSC (CD11b+Gr−hi) abundance in the tumor-bearing hosts (FIG. 30). Collectively, these data demonstrate that host ERβ phosphotyrosine switch is important for dampening primary and metastatic tumor growth, possibly through rallying antitumor immunity.

ERβ Signaling in CD8+ T Cells Confers Host Tumor-Inhibitory Activity

Figure 24:
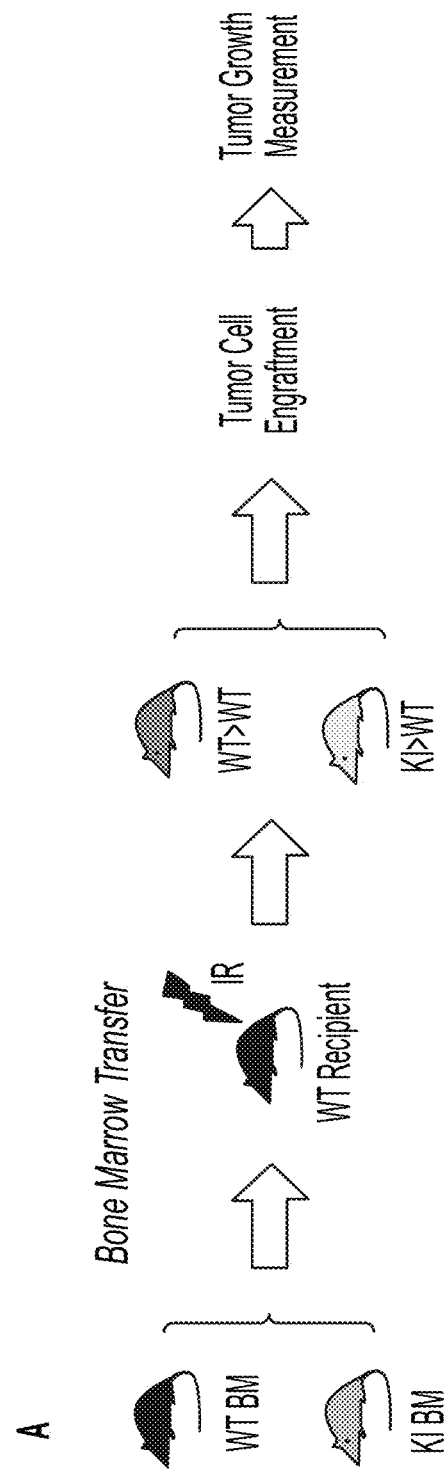
FIG. 24. ERβ signaling in CD8+ T cells confers tumor inhibition.
Figure 24:
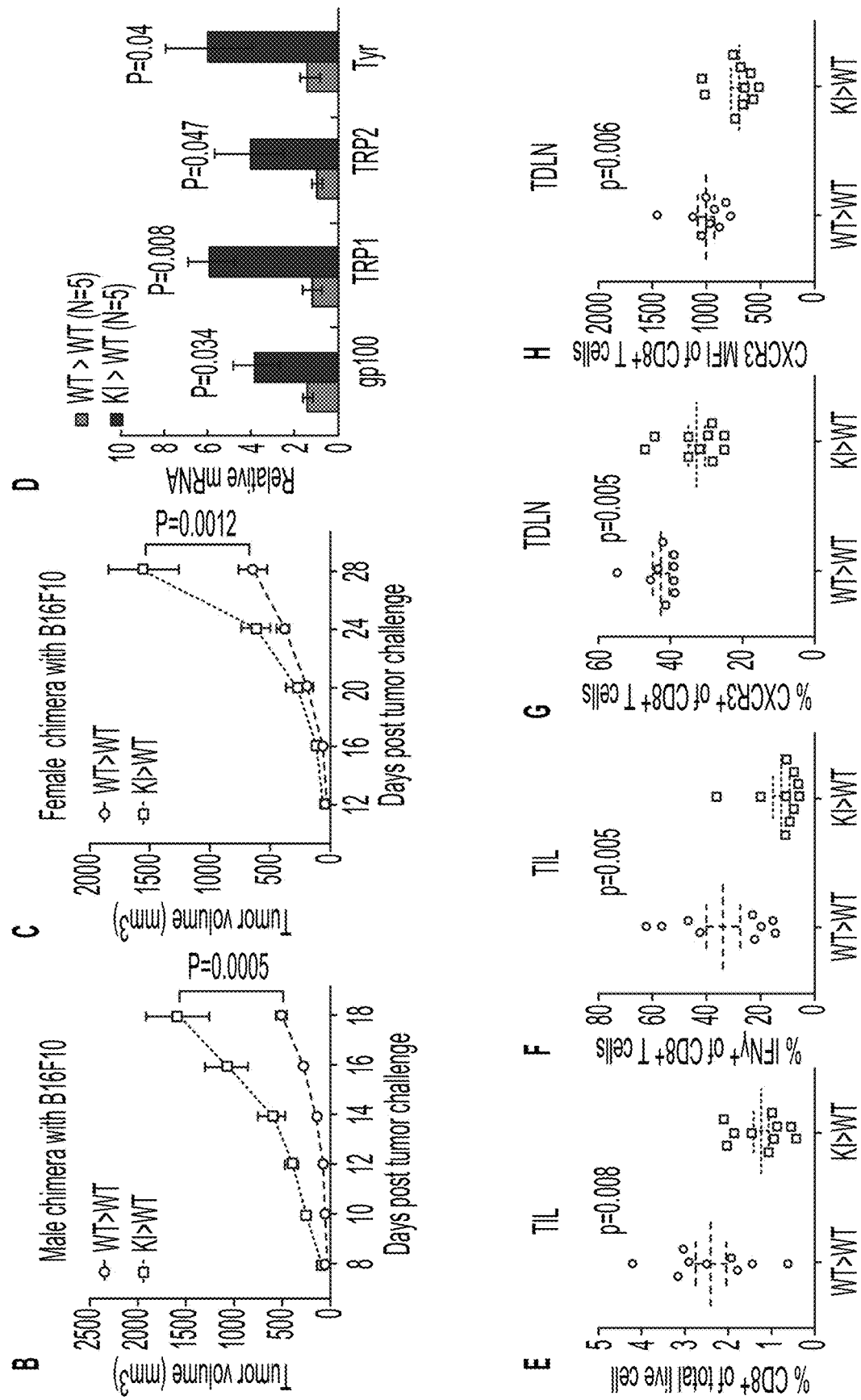
Figure 24:
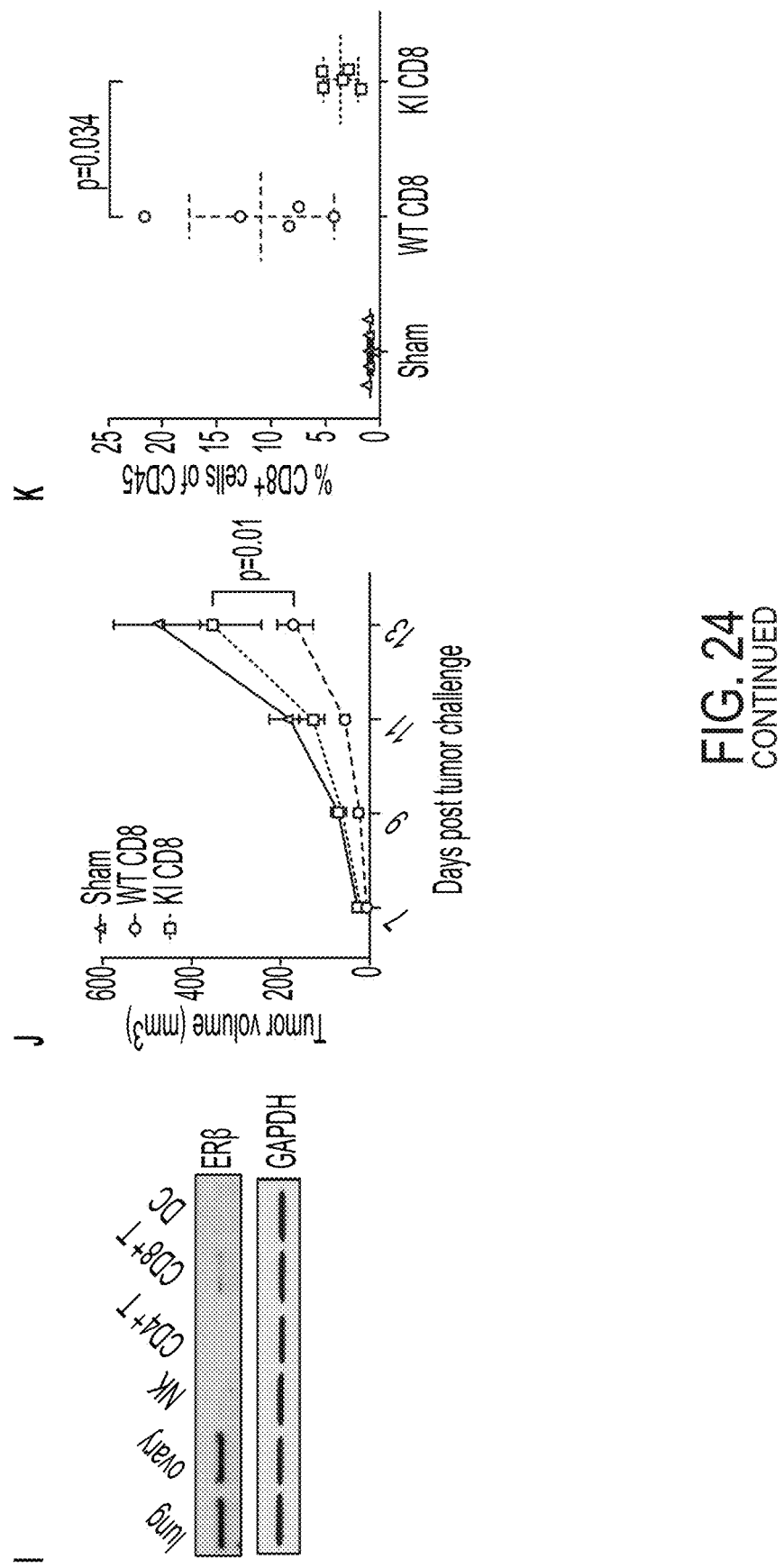
Figure 31:
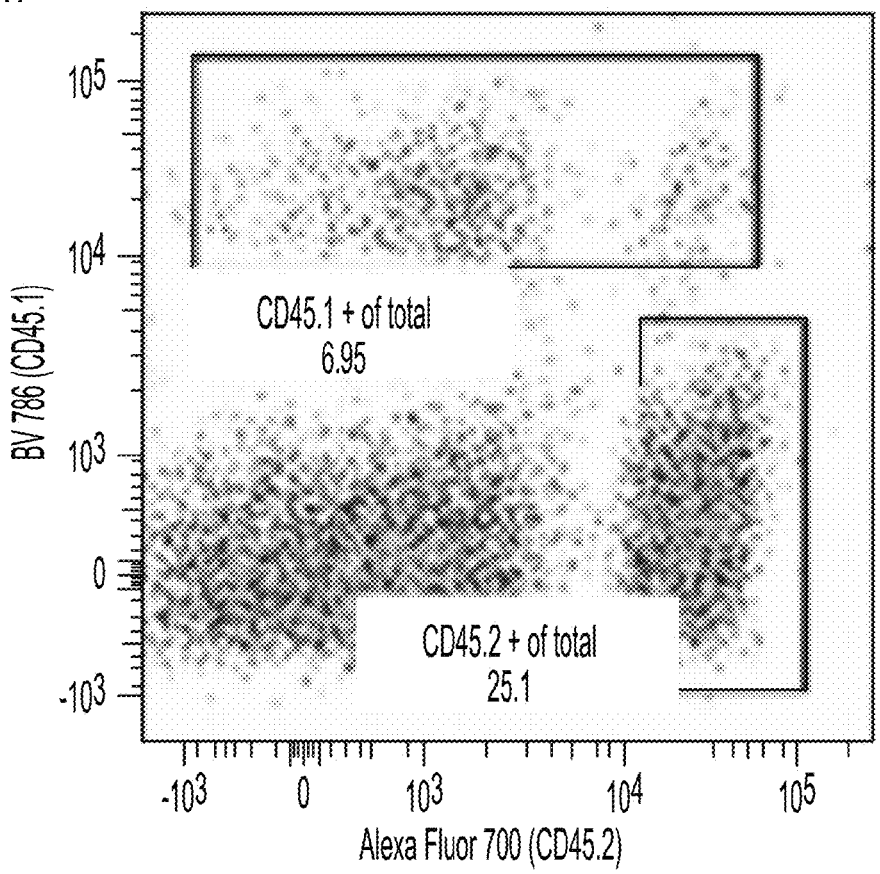
FIG. 31. Tumor growth in chimeric mice reconstituted with WT or KI bone marrow.
Figure 31:
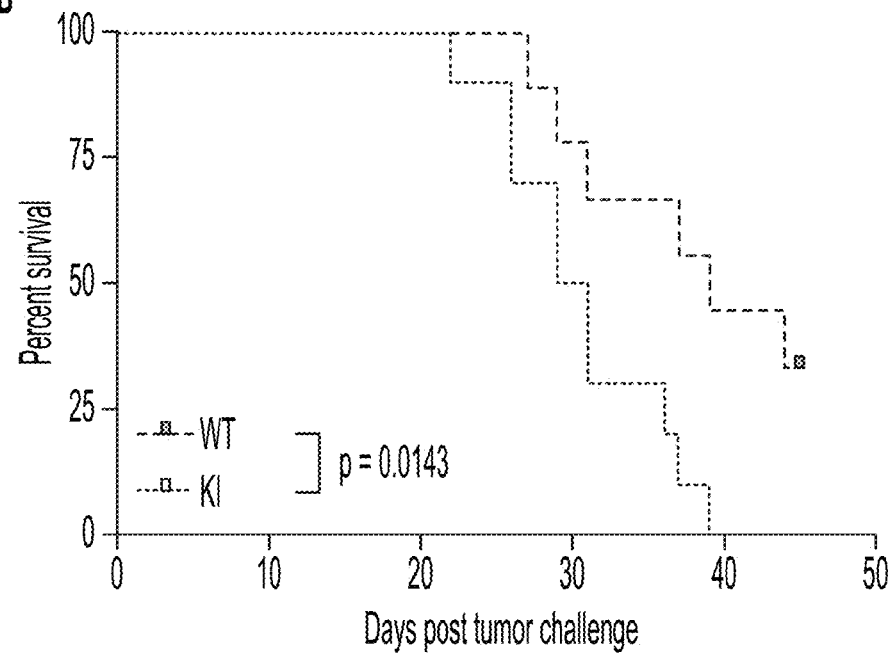
Figure 31:
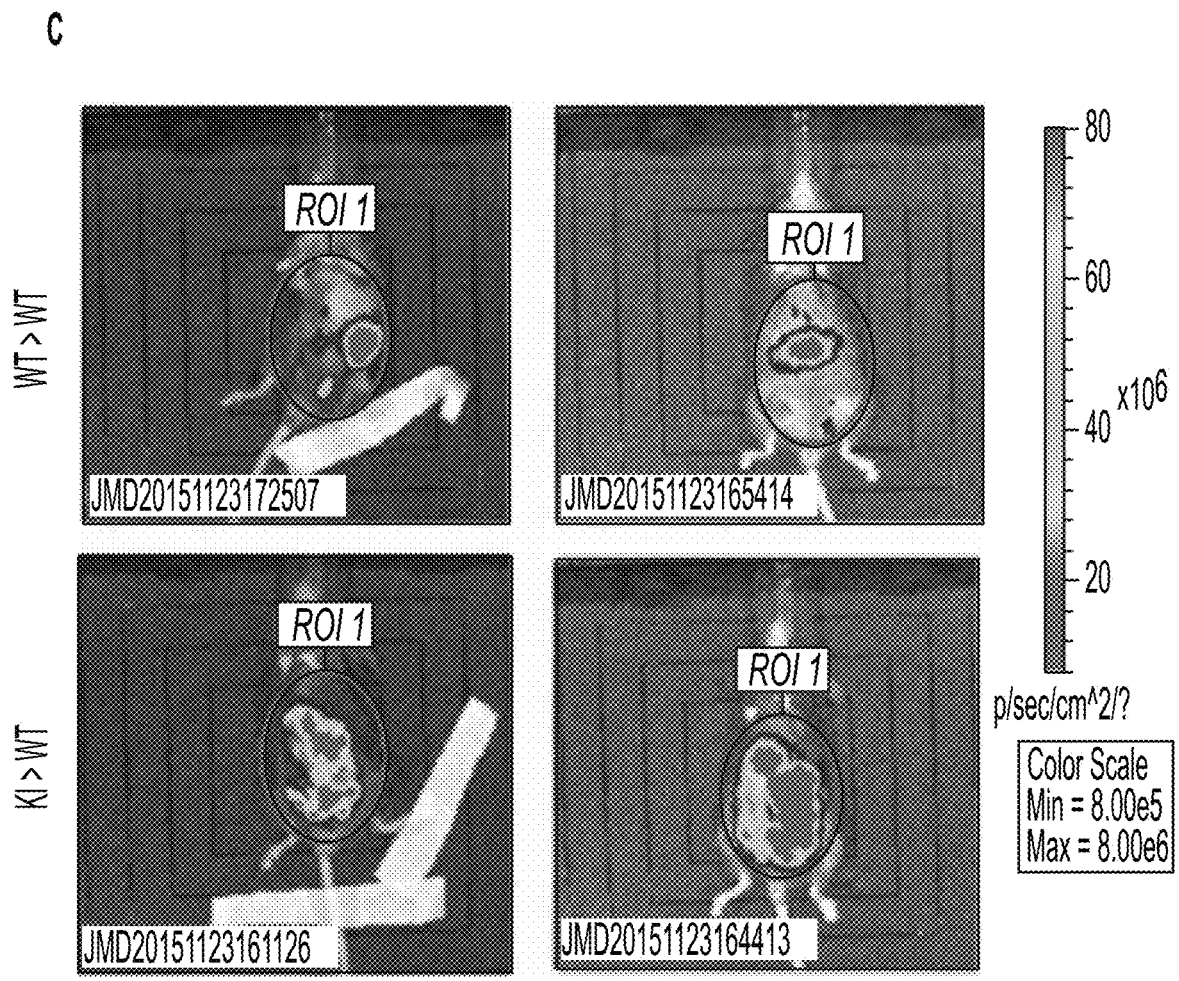

The next study sought to delineate the cellular source of host ERβ signaling in tumor inhibition. Given the significantly reduced TIL abundance in tumors from KI hosts, a mouse chimera experiment was conducted involving bone marrow transplant (FIG. 24A). Male WT recipient mice were first irradiated (10 Gy) to kill endogenous bone marrow cells, followed by transplant with bone marrow from syngeneic male WT or KI donors. After confirming successful chimerism in WT>WT and KI>WT mice (FIG. 31A), B16F10 melanoma cells were injected 8 weeks after bone marrow transplant. Tumor growth was significantly faster in male and female KI>WT chimeras (with KI immune cells) versus their WT>WT control (FIG. 24B-C), suggesting that KI-derived immune cells poorly deterred tumor growth. Consistent with findings from parental KI recipient mice (FIG. 28D), melanoma-associated lung metastasis was greater in male KI>WT mice versus WT>WT control (FIG. 24D). In a separate experiment, ovarian tumor cells were peritoneally injected into female chimera hosts and observed significantly shorter median survival (30 days) of KI>WT mice than their WT>WT control (39 days, p=0.0143, FIG. 31B-C). This study strongly suggests that ERβ signaling regulates its antitumor activity in bone marrow-derived host cells of both male and female mice.

Figure 32:
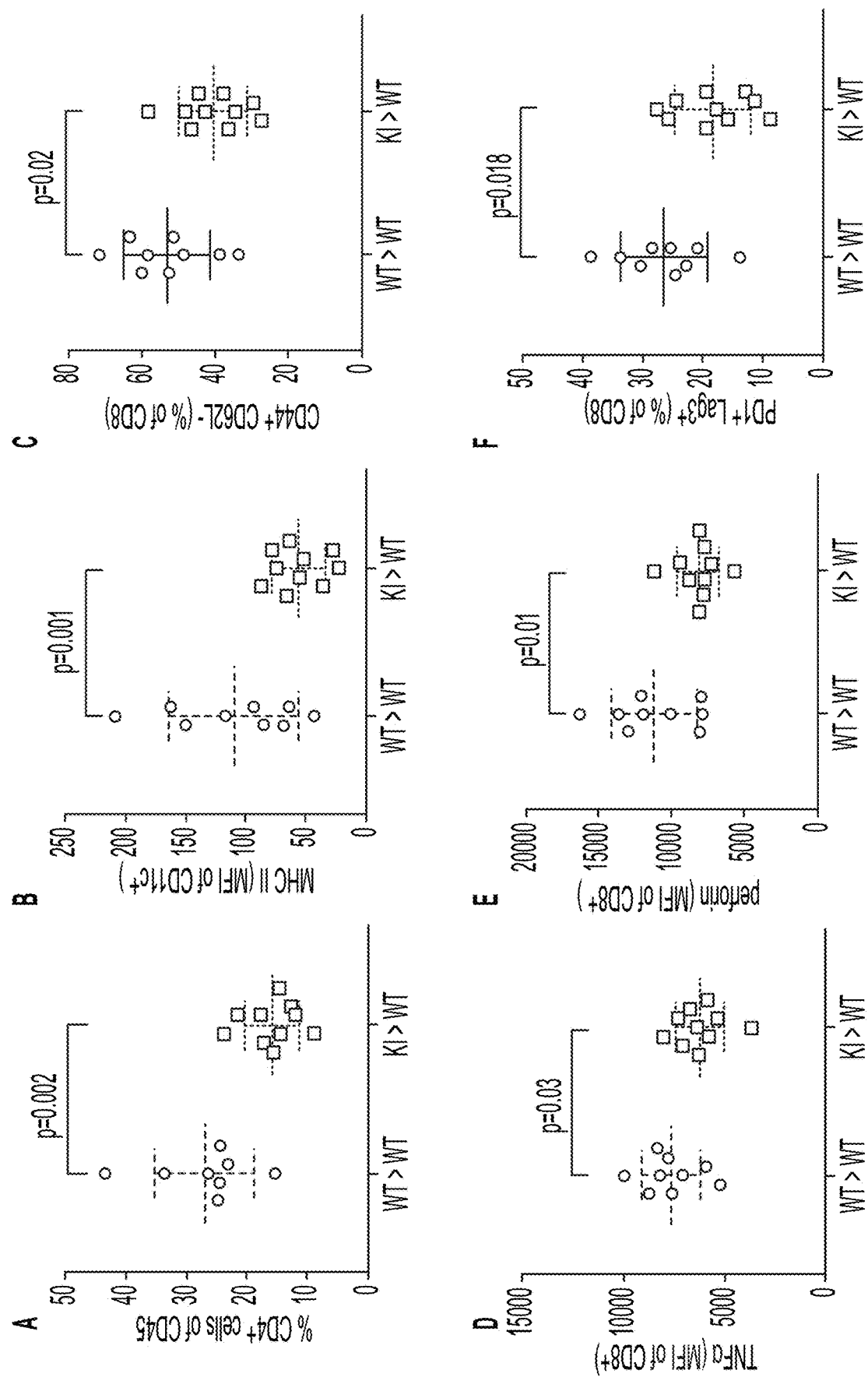
FIG. 32. Immunophenotyping of tumors from chimera mice.

In a corollary experiment, we analyzed TILs and tumor-draining lymph nodes (TDLN) from the male B16F10 tumor-bearing chimera mice. In support of the notion that antitumor immune response of KI mice is compromised, total numbers of tumor-infiltrating CD4+ and CD8+ T cells were reduced in KI>WT versus WT>WT mice (FIG. 24E, FIG. 32). The percentage of IFNg-producing CD8+ cells was significantly lower in tumors from KI>WT versus WT>WT mice (FIG. 24F), suggesting compromised cytotoxic potency of CD8+ T cells in the absence of functional ERβ signaling. Percentage and mean fluorescence intensity (MFI) of CXCR3 in CD8+ T cells was decreased in TDLN of KI>WT mice (FIG. 24G-H). In addition, activation of dendritic cells, which prime antitumor T cells, was also compromised in KI>WT chimeric mice, as evidenced by their reduced MHC-II expression (FIG. 32). Furthermore, effector T cells were less activated (CD44/CD62L) and had reduced additional effector functions in KI>WT chimeras 309 (e.g., tumor necrosis factor alpha (TNF)a, interleukin (IL)-2, and perforin, FIG. 32). T cell PD-1 and Lag3 were also reduced in tumor-bearing KI mice (FIG. 32). These markers were thought to mark "exhausted" T cells with reduced antitumor functions, but recent work shows that they can also identify activated antitumor T cells. Together, these data strongly suggest ERβ-dependent augmentation of antitumor CD8+ T cell effector activity and improved tumor immune cell trafficking, which could be from increased dendritic cell activation and/or CD4+ T cells as immune mechanisms for ERβ-driven anti-tumor activity.

Figure 21:
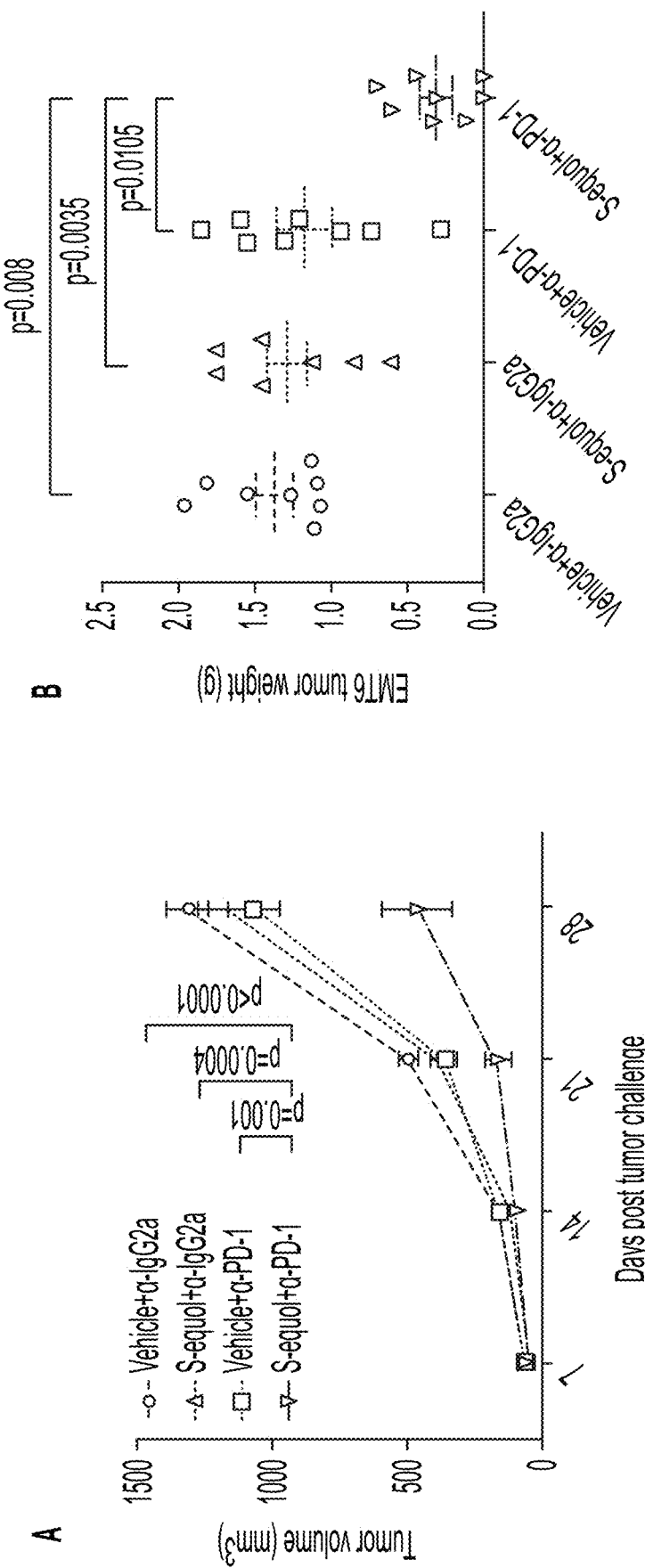
FIG. 21. S-equol and/or α-PD-1 treatment with EMT6 mammary tumors. Mice were injected with $3 \times 10^5$ EMT6 cells. α-PD-1 was administered at 200 μg/mouse, intraperitoneally every 3 days and S-equol was administered at 50 mg/kg/day by oral gavage daily.
Figure 21:
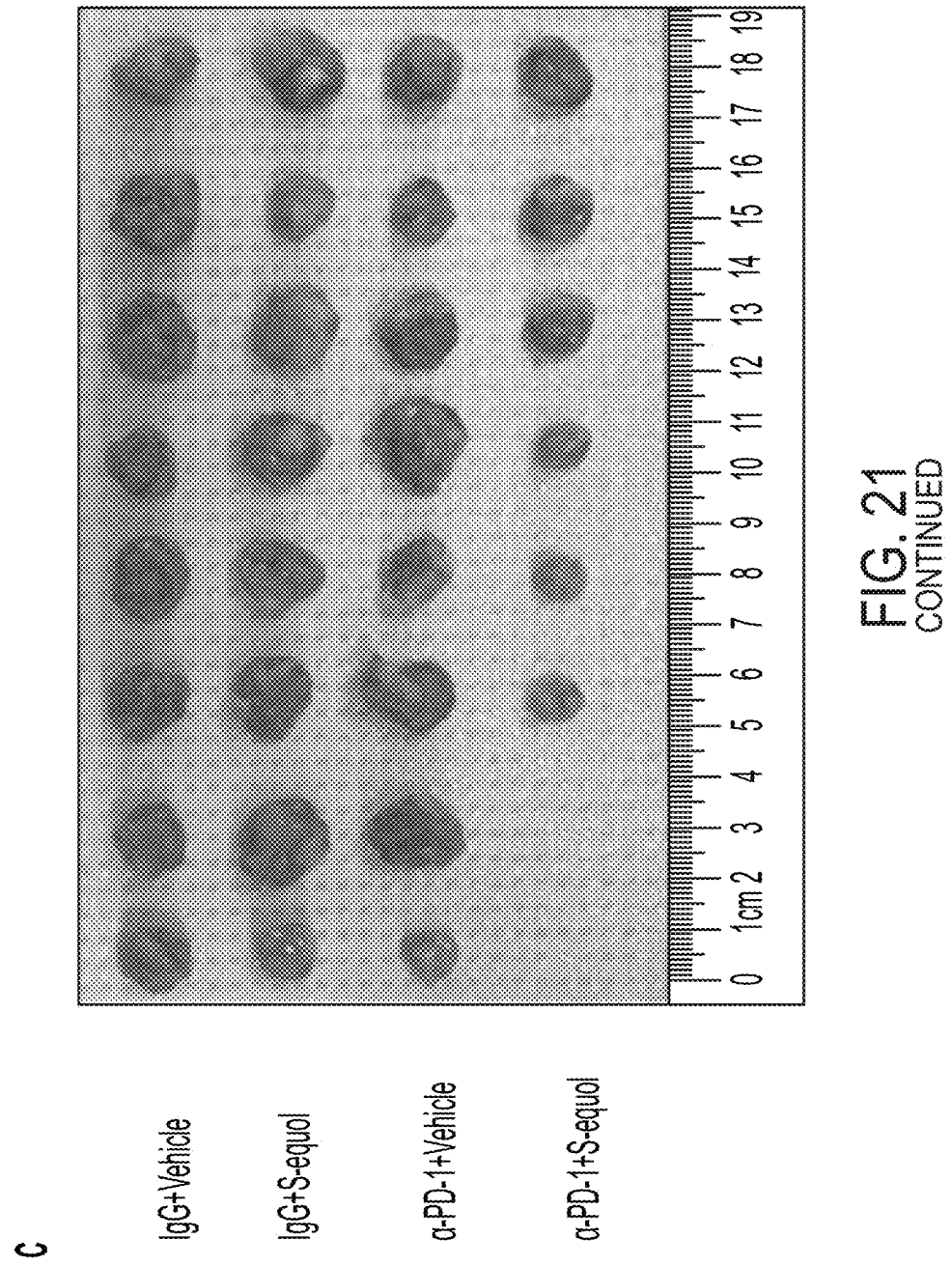
Figure 22:
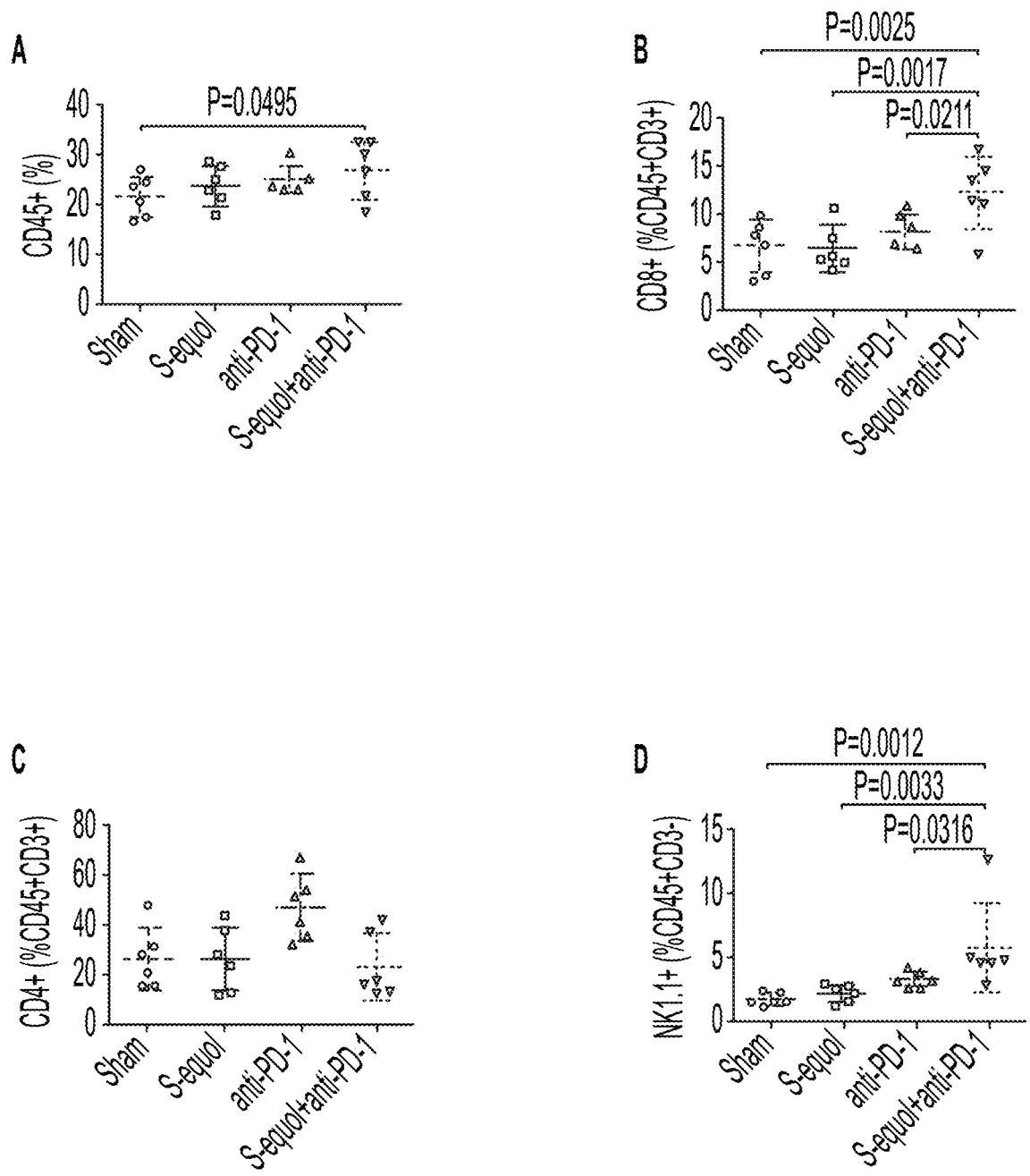
FIG. 22. Expression of markers on EMT6 tumor cells after treatment.
Figure 22:
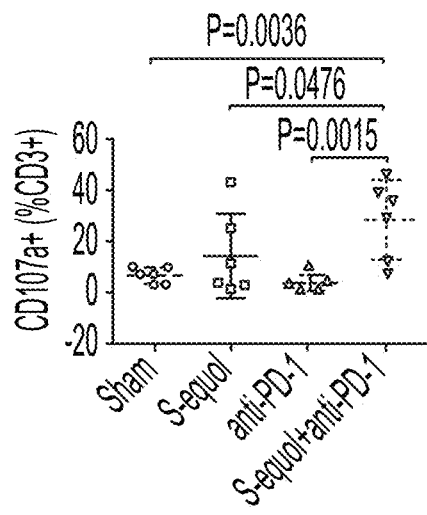
Figure 22:
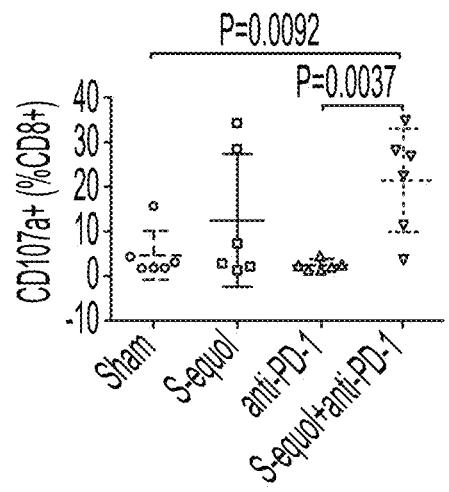
Figure 22:
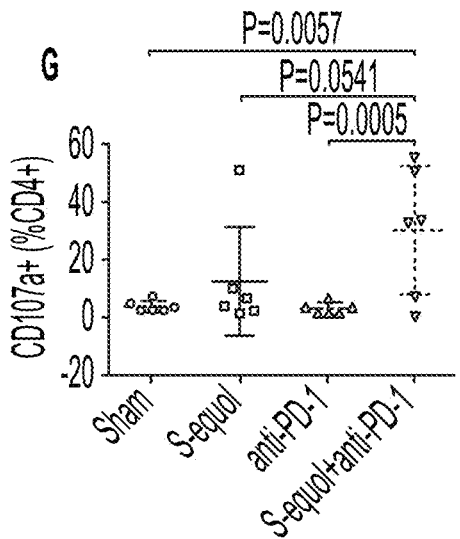
Figure 22:
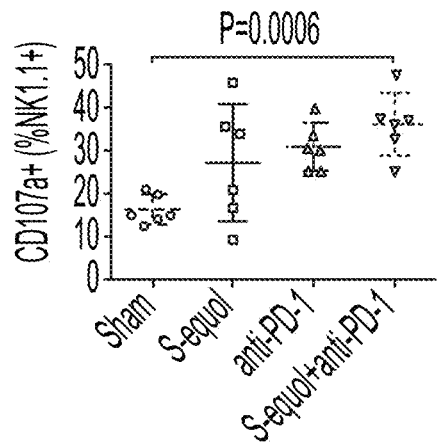
Figure 25:
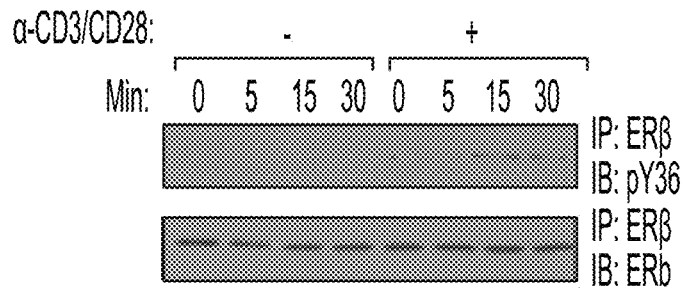
FIG. 25. ER 13 signaling promotes CD8+ T cell activation.
Figure 25:
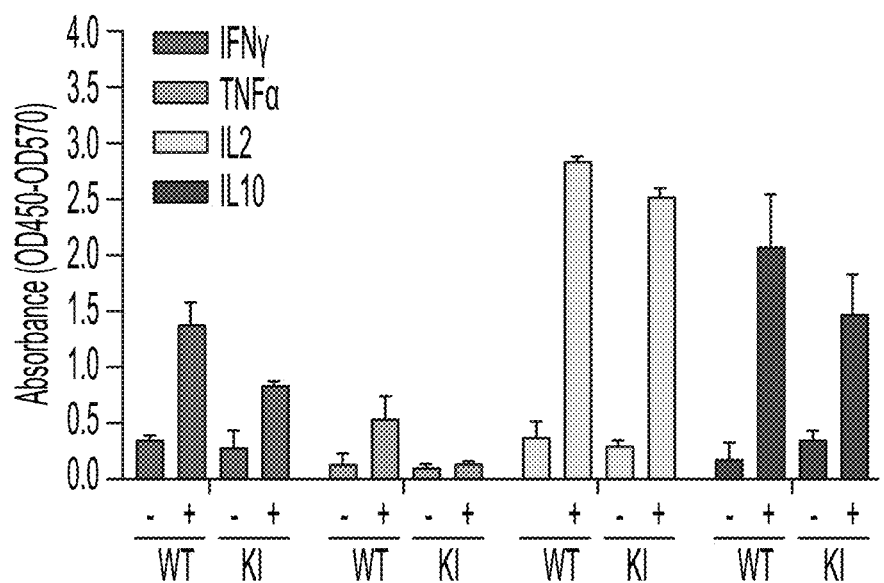
Figure 25:
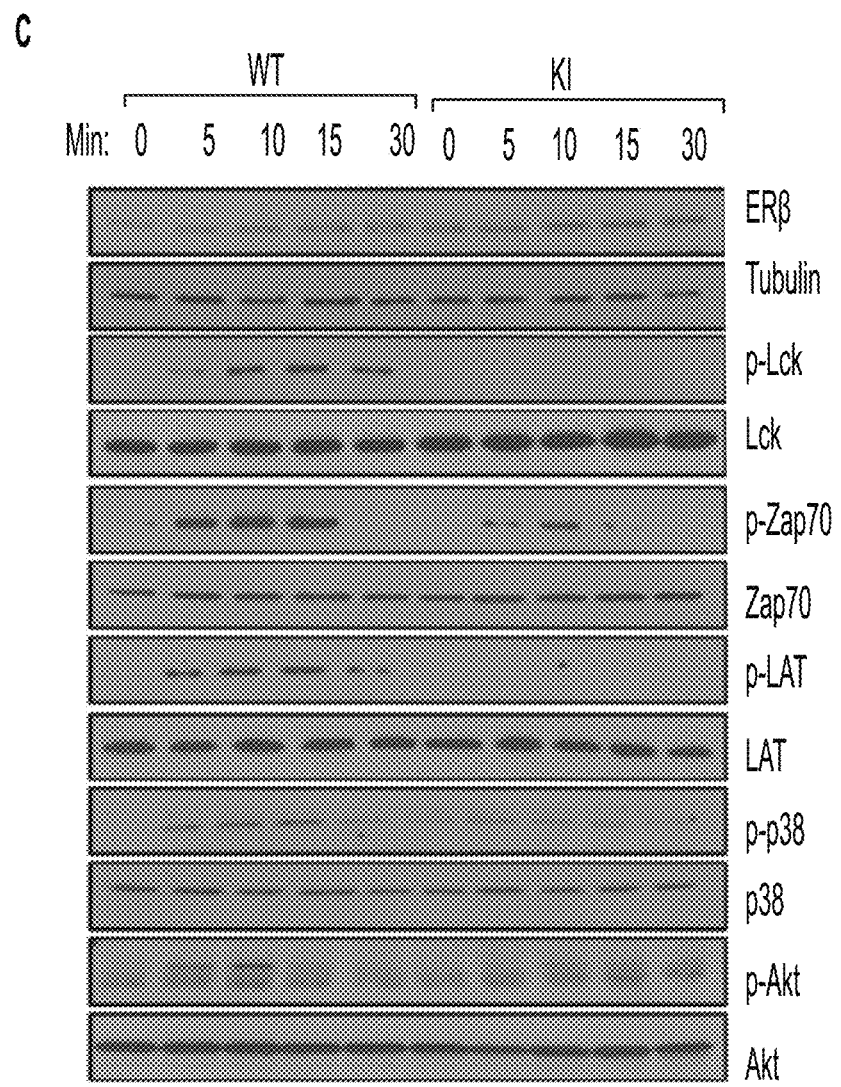

To identify the specific immune cell type(s) that confers ERβ-dependent reinforcement of antitumor immunity, published work shows that ERβmRNA is expressed in various immune cell types including CD8+ T cells and dendritic cells, but is barely detectable in CD4+ T cells 26-29. Immunoblotting of purified primary mouse immune cells indicates that ERβ protein levels are higher in CD8+ T cells than other immune cells examined (FIG. 21). To assess a cell-autonomous antitumor effect of ERβ signaling in CD8+ T cells, CD8+ T cells were purified from WT and KI mice and adoptively transferred them into immunodeficient Rag-/-324 recipient mice. Subsequent tumor study indicates that adoptively transferred WT CD8+ T cells conferred significant inhibition of tumor growth as compared to either sham or KI CD8+ T cells (FIG. 25J). When abundance of TILs was examined, the number of KI CD8+ T cells was substantially lower than WT control (FIG. 25K). Together, these data provide compelling evidence for a cell-autonomous role of ERβ signaling in CD8+ T cells in galvanizing antitumor immunity.

Non-Genomic Action of ERβ in CD8+ T Cells Boosts T Cell Activation

To elucidate the underlying mechanism by which the ERβ signaling promotes CD8+ effector T cell function, primary CD8+ T cells were purified from mouse splenocytes and activated them in vitro with anti-CD3/CD28. Y55 phosphorylation of WT ERβ was substantially elevated following T cell activation (FIG. 25A). Importantly, upon anti-CD3/CD28 treatment, KI CD8+ T cells with abolished ERβ phosphotyrosine switch yielded significantly less cytotoxic cytokines including IFNg and TNFα than their WT counterparts (FIG. 25B), further corroborating a cell-autonomous role of ERβ signaling in CD8+ T cell function.

Initiation and propagation of TCR signaling involves phosphorylation of several proximal signaling molecules including Lck, Zap70, and LAT, as well as activation of additional downstream signaling molecules such as Akt and p38 (Courtney, 2018). These posttranslational events, which are independent of gene activation at the transcriptional level, occur within minutes following TCR binding to its antigenic ligands. Following anti-CD3/CD28 treatment in vitro, TCR-stimulated phosphorylation of these signaling molecules was readily detectable as early as 5 min following TCR activation (FIG. 25C). In stark contrast, disabling of the ERβ phosphotyrosine switch markedly attenuated the TCR-triggered signaling cascade in KI CD8+ T cells (FIG. 25C). Given the short time frame of the initial steps in TCR activation (i.e., minutes instead of hours), it was reasoned that ERβ unlikely facilitates this rapid process through transcriptional activation after anti-CD3/CD28 treatment. Furthermore, RNA-seq of primary WT and KI CD8+ T cells before in vitro activation did not reveal any significant ERβ-dependent, baseline transcriptomic changes (data not shown). Thus, ERβ signaling promotes rapid activation of TCR signaling cascade of CD8+ T cells is likely independent of its canonical transcriptional activity.

Figure 26:
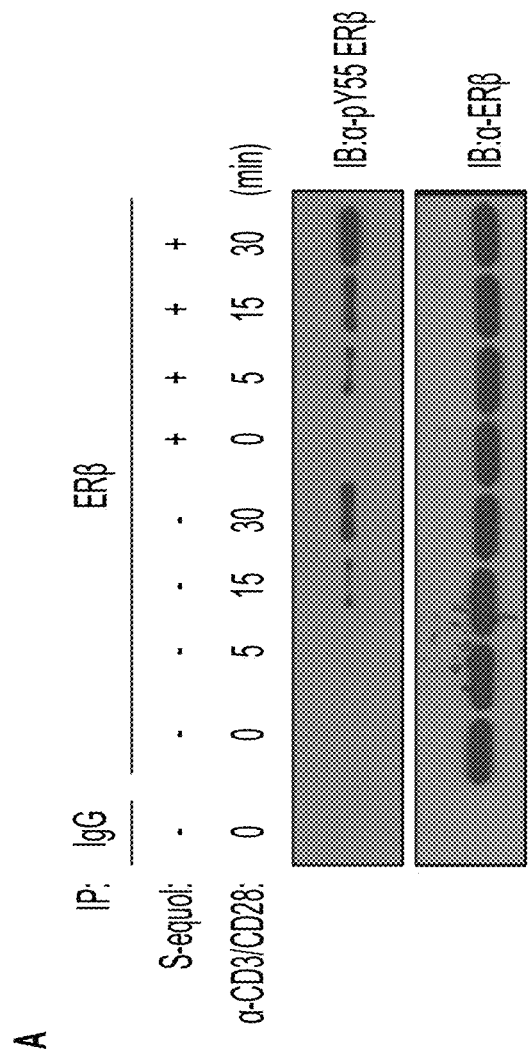
FIG. 26. ERβ agonist S-equol promotes CD8+ T cell activation and antitumor immunotherapy.
Figure 26:
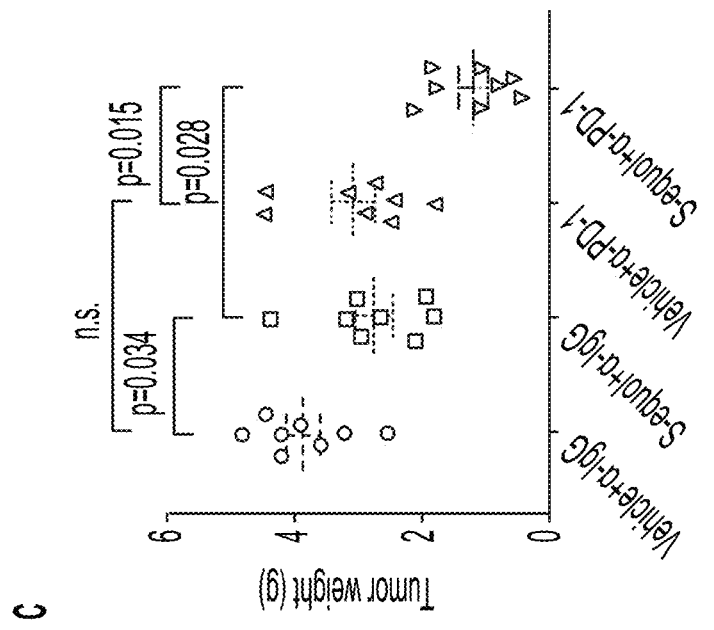
Figure 26:
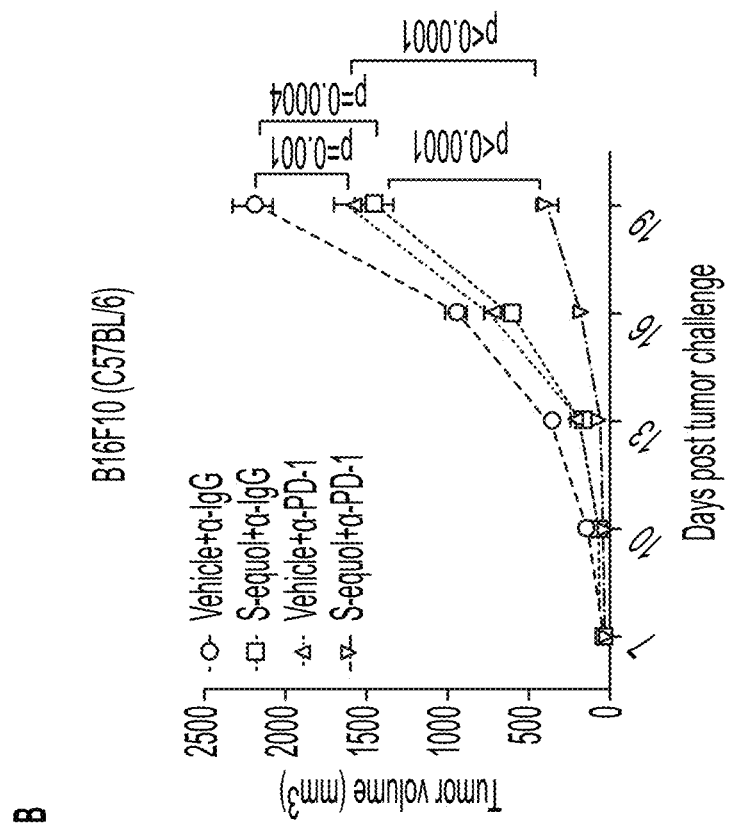
Figure 26:
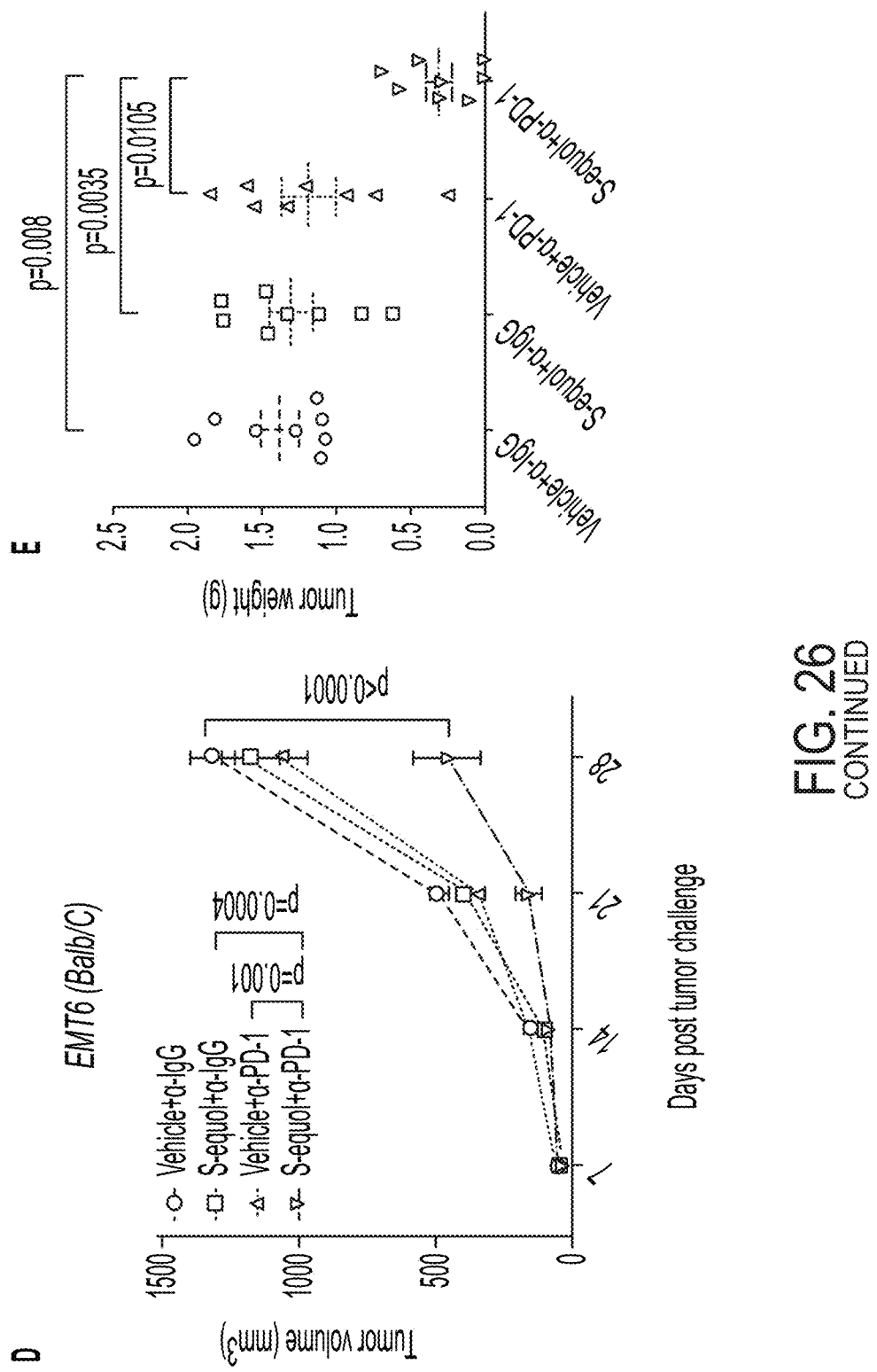
Figure 26:
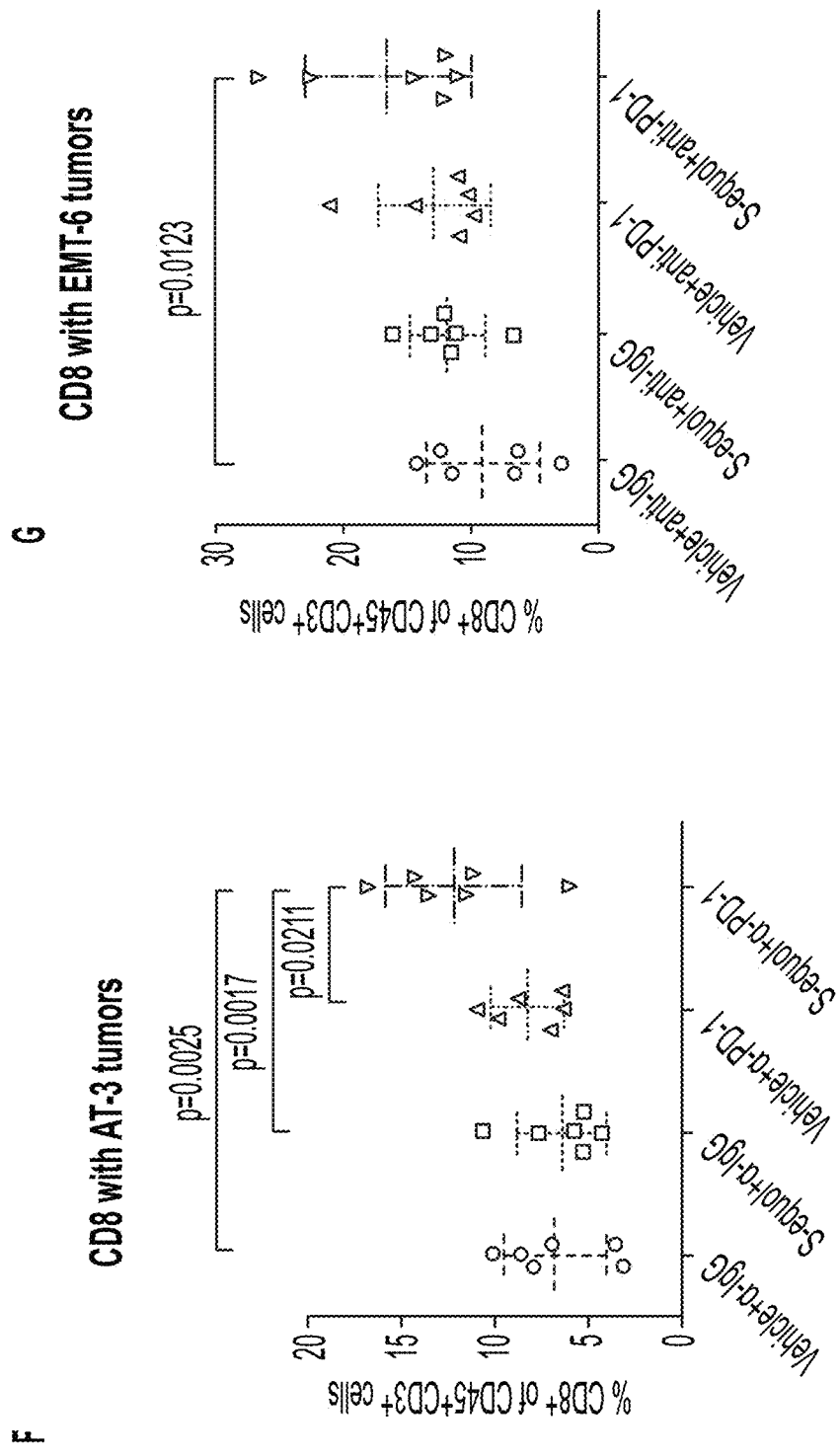
Figure 33:
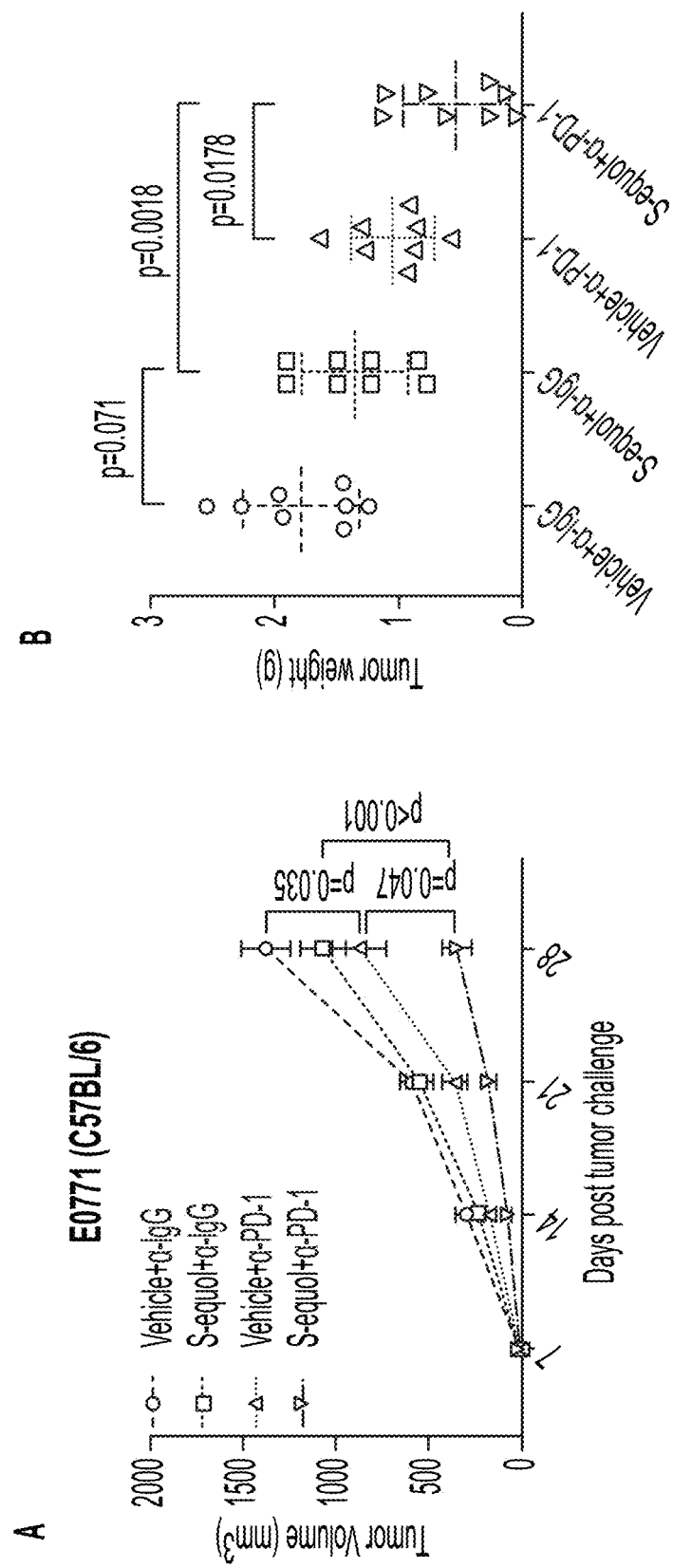
FIG. 33. ERβ-selective agonist S-equol boosts anti-PD-1 immunotherapy.
Figure 33:
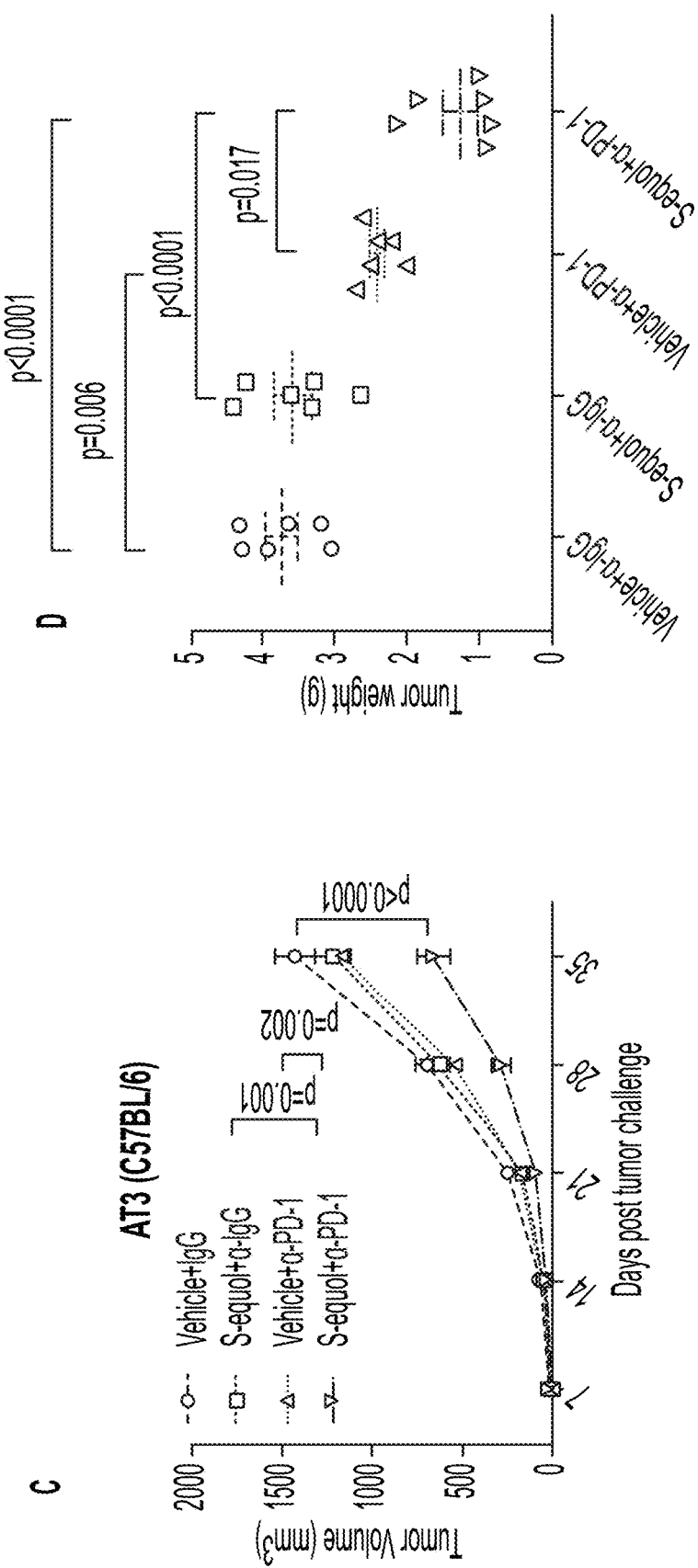
Figure 34:
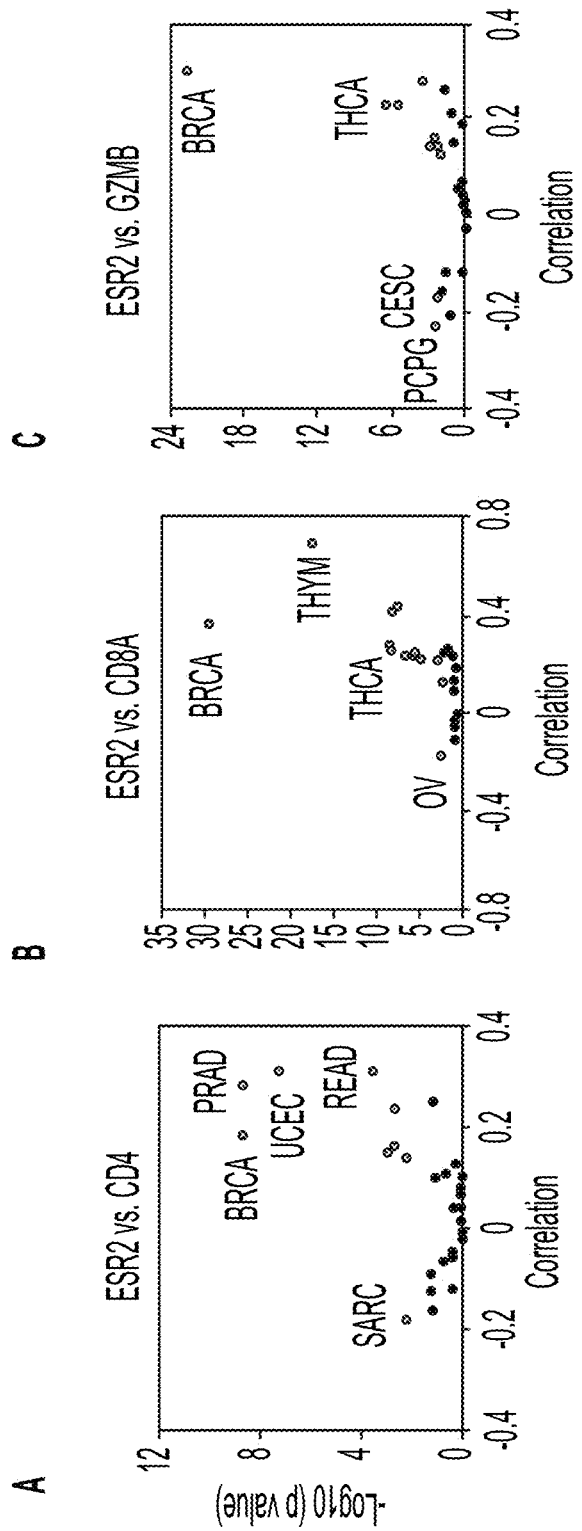
FIG. 34. Correlation of ERβ and antitumor immune signature gene expression.
Figure 34:
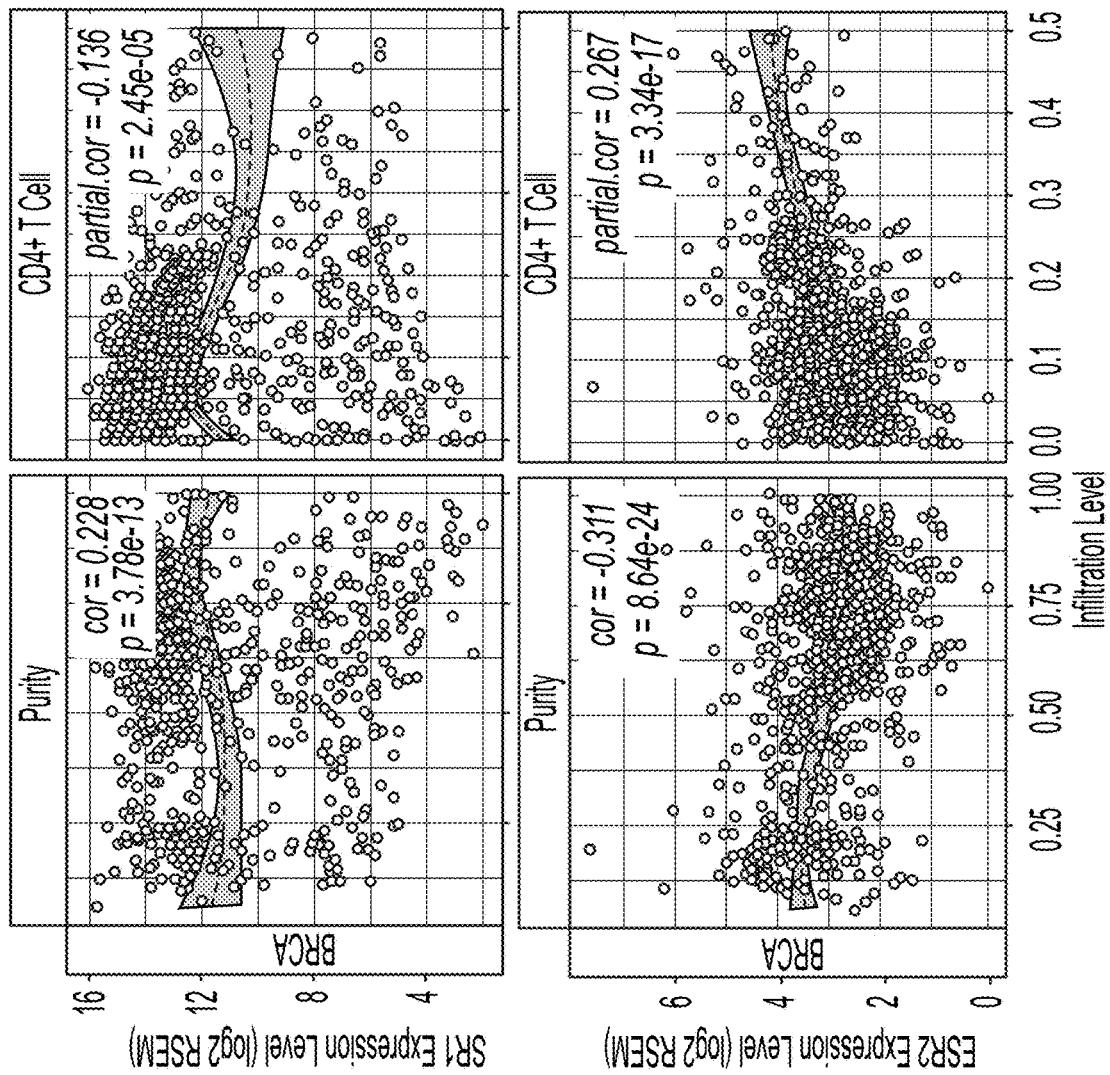
Figure 34:
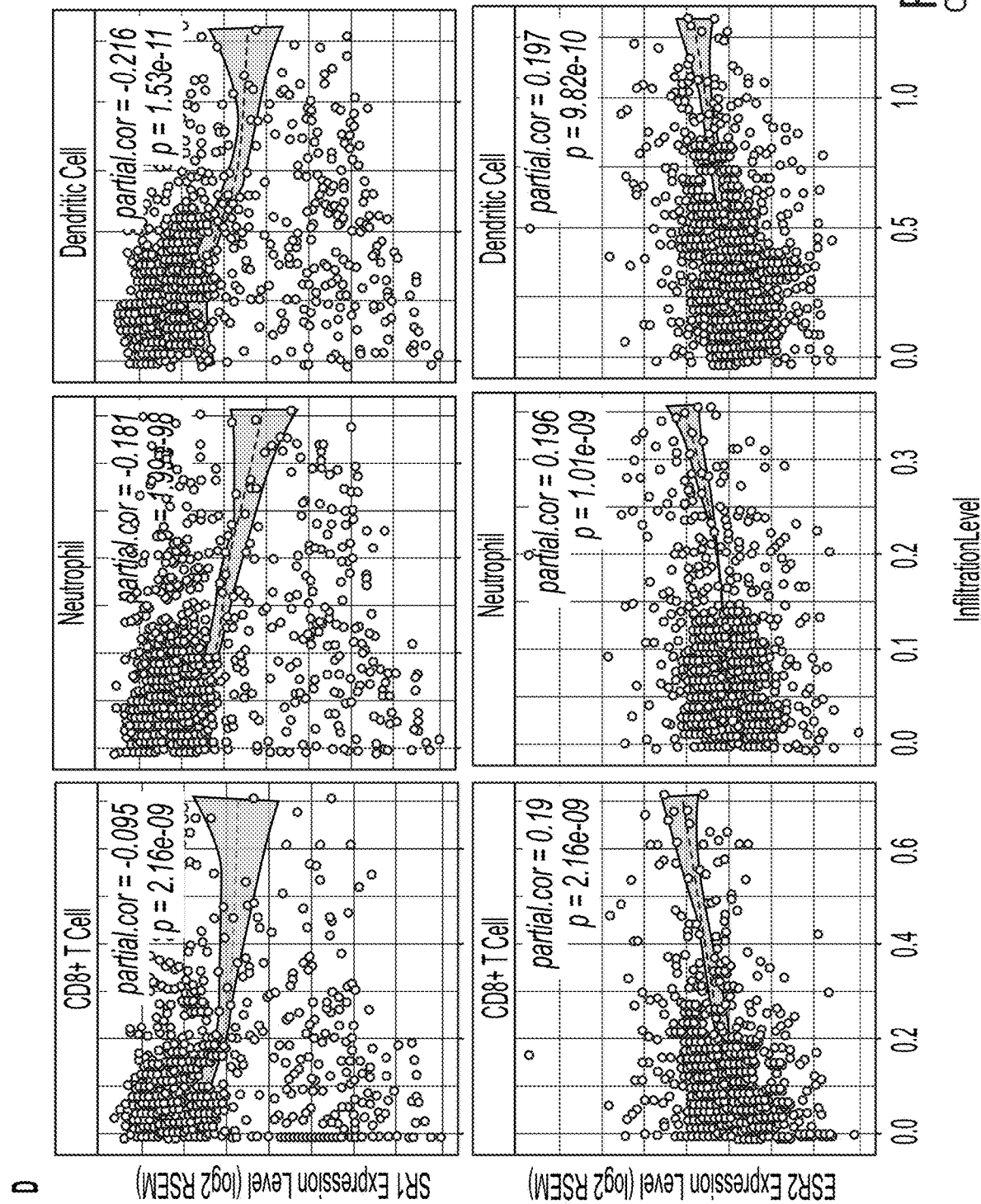
Figure 34:
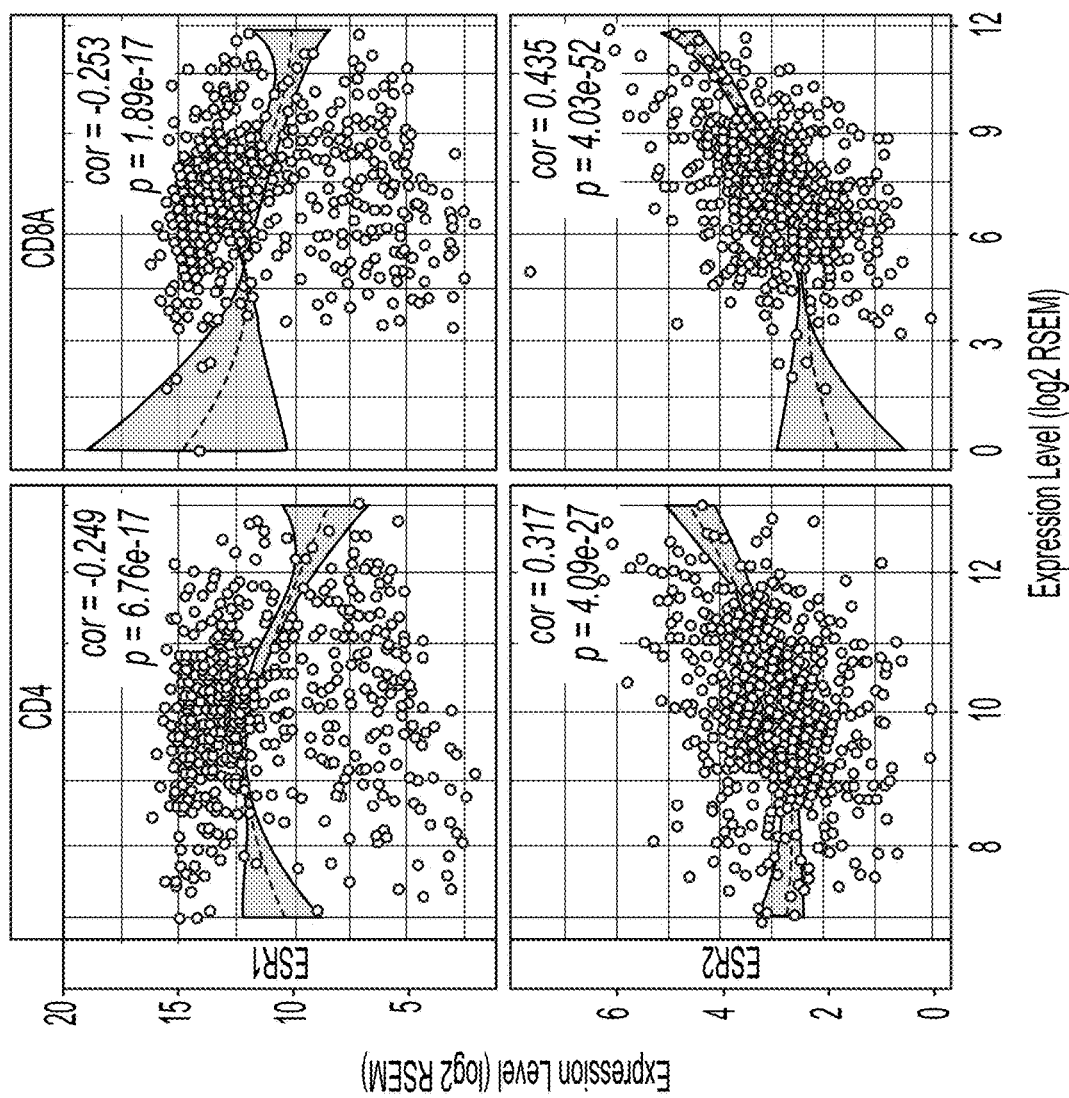
Figure 34:
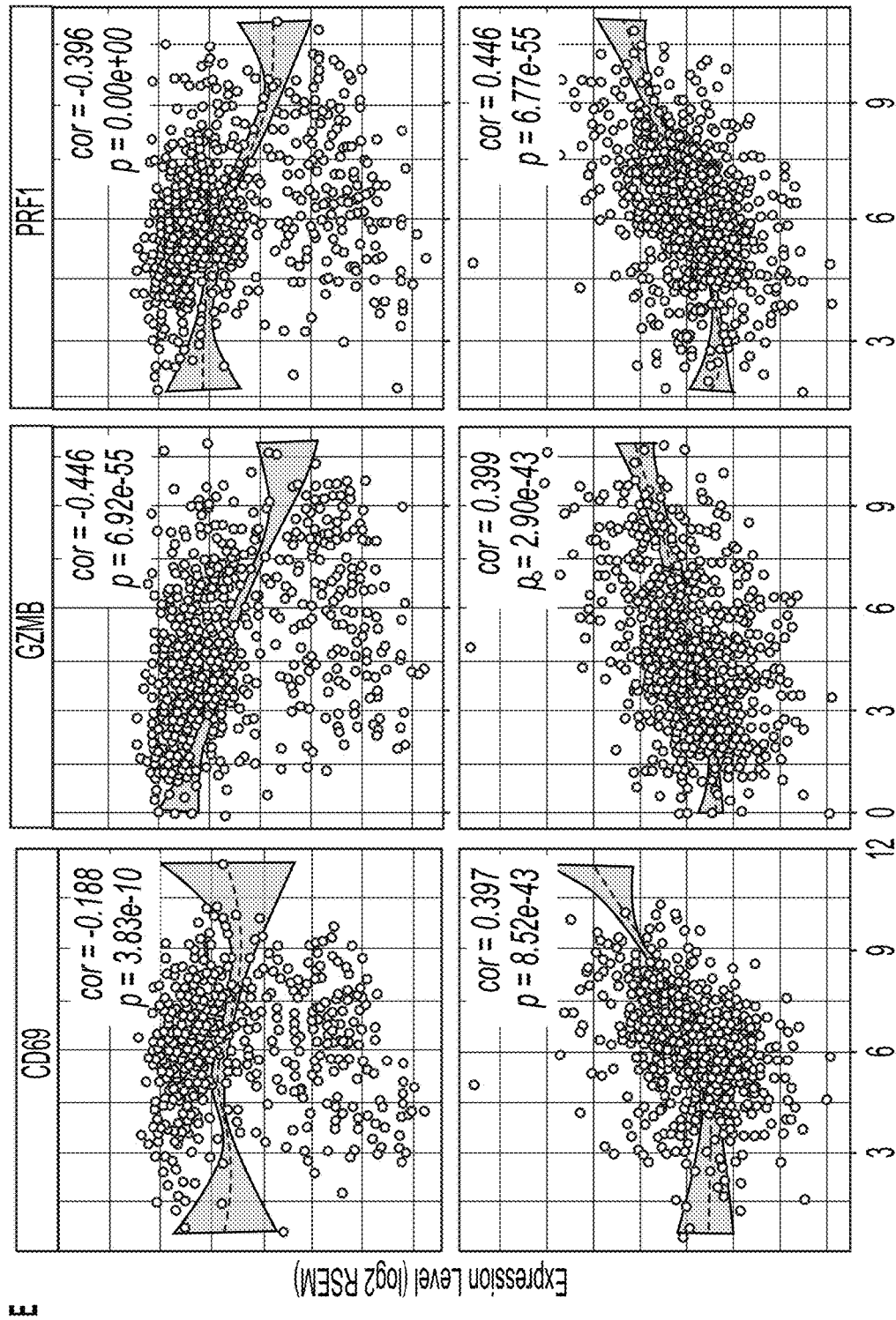
Figure 34:
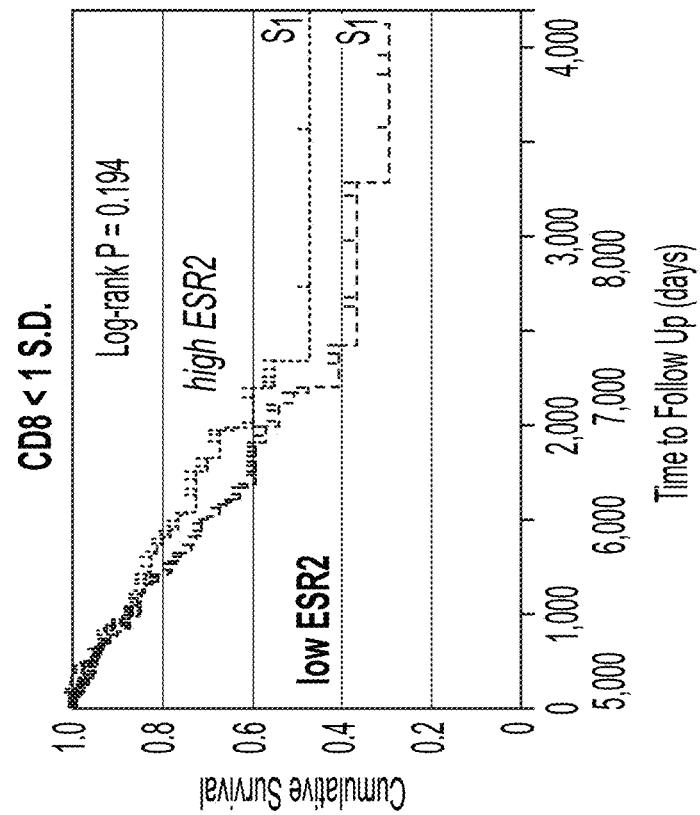
Figure 34:
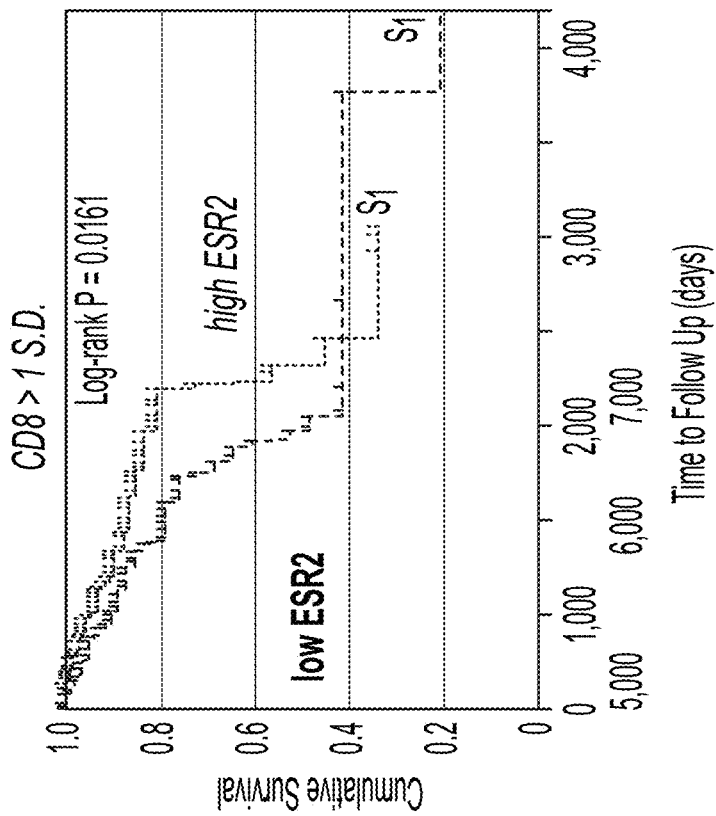

Activation of ERβ Signaling by ERβ Agonist S-Equol Enhances aPD-L1 Immunotherapy Published work shows that ERβ-selective agonist S-equol promotes human ERβ phosphorylation at Y36 in breast cancer cells (Yuan, 2016). S-equol further enhanced TCR activated ERβ tyrosine phosphorylation in anti-CD3/CD28-stimuated mouse EF4 lymphoma cells (FIG. 26A). In light of this in vitro finding, it was sought to assess a potential effect of S-equol on boosting antitumor efficacy of aPD-1 in several syngeneic mouse tumor models. This experimental design included four arms: (1) IgG controls, (2) aPD-1, (3) S-equol, and (4) aPD-1+S-equol. In B16 melanoma and E0771 mammary tumor models, tumors responded to αPD-1 or S-equol monotherapy, but the responses to the combination treatment were significantly more pronounced than single ones (FIG. 26B-C, FIG. 33A-B). In two additional mammary tumor models (AT-3 and EMT6), only combination treatment resulted in appreciable tumor reduction (FIG. 26DE, FIG. 33C-D). Consistent with the tumor growth assessment, combination of aPD-1 and S-equol resulted in substantially increased tumor-infiltrating CD8+ T cells versus control and single treatment groups (FIG. 26F-G). In aggregate, our data demonstrate the ability of S-equol to sensitize various syngeneic tumors to anti-PD-1 ICB immunotherapy.

To explore clinical correlation between ERβ and antitumor immunity, a bioinformatics tool (TIMER) was used to assess tumor-immune correlations in human tumor samples (Wherry 2015). Several solid cancer types display significant positive correlation between ERβ mRNA levels and genes associated with antitumor immunity including CD4, CD8A, and GZMB (FIG. S9A-C). Of note, the strongest correlation of ERβ with CD8A and GZMB was observed in breast cancer (FIG. S9B-C). When the immune marker correlation was compared for ESR1 and ESR2 377 specifically in breast cancer, it is striking that unlike ESR2, ESR1 exhibits a negative association with these antitumor immune markers, supporting the notion that ERα and ERβ play opposite roles in tumor immune microenvironment. Furthermore, analysis of publicly available breast cancer-related patient survival datasets shows that higher ESR2 expression levels correlate with longer patient survival, but the correlation is only significant in tumors with relatively abundant tumor-infiltrating CD8+ T cells. Together, these clinical correlations demonstrate a prominent role of ERβ signaling in rallying strong antitumor immune response in host CD8+ T cells.

Discussion

Pathophysiological significance of ERβ signaling is an important yet historically under investigated research topic. Despite an increasing appreciation for its anticancer therapeutic potential, there previously was compelling genetic evidence for a definitive role of ERβ signaling in cancer development and progression, which dampers rationalized efforts to mobilize it with precision and synergy. The discovery of an ERβ-specific and tumor-extrinsic ERβ phosphotyrosine switch in antitumor immunity provides a previously unrecognized approach for assessing and rallying ERβ activity in cancer treatment. In particular, the involvement of ERβ signaling in antitumor immunity broadens the horizon for combination therapies that could maximally boost efficacy of ICB immunotherapies and increase survival benefits for more cancer patients. Furthermore, the newly established ERβKI mouse model provides a powerful tool for further elucidating phospho-ERβ-dependent ERβ functions in normal physiological and disease conditions, and tumor-intrinsic versus extrinsic contexts.

Previously published work identified c-Abl and EYA2 as the kinase and phosphatase, respectively, that directly and diametrically control ERβ phosphotyrosine status in breast cancer cells (Pierdominici 2010). It remains to be confirmed whether these molecules directly regulate the ERβ phosphotyrosine switch in CD8+ T cells. However, it is worth noting that c-Abl has been implicated in mediating TCR activation (Zipfel, 2004). Furthermore, clinical trials of pharmacological inhibitors of BCR-Abl for solid tumors yielded mixed results, which could be due to the complex action of c-Abl in tumor and host immune cells. ERβ phosphotyrosine in CD8+ T cells could be regulated by other tyrosine kinases. A mammalian expression library was previously screened for all known human tyrosine kinases. In addition to c-Abl, Zap70 was also identified as a candidate kinase for human ERβ phosphorylation at the Y36 residue. It is therefore conceivable that Zap70 and ERβ could form a positive regulatory loop whereby Zap70 phosphorylates ERβ, which in turn promotes Zap70 association with other signaling molecules in TCR-mediated immune activation.

In addition to full-length ERβ(ERβ1), the human ESR2 gene also produces several splicing variants (ERβ2-5) with distinct and even opposite biological activities. However, the nature and functions of the corresponding variants for mouse Esr2 remain unclear. Because all known human variants share the same N-terminal sequence and thus the phosphotyrosine switch, similar putative variants in mouse KI mouse model would be affected as well as the full-length ERβ protein. Future work is warranted to distinguish the effect of the phosphotyrosine switch on full-length and possible splicing variants in human and murine immune cells.

Despite major breakthroughs in anticancer immunotherapies, they are effective only for some patients and usually not curative (Katzenellenbogen 2000; McDonnell 2002; Heldring 2007; Deroo 2006). Thus, it is imperative to develop novel stand-alone immunotherapies and/or agents that can improve existing anticancer immunotherapies. Multiple clinical trials have demonstrated human safety of several synthetic and natural ERβ-selective agonists. In particular, S-equol, a soybean byproduct due to the action of gut bacteria, was used in multiple phase I and II clinical trials for the treatment of menopausal symptoms, benign prostatic hyperplasia, and more recently triple negative breast cancer. The antitumor effect of S-equol observed in the current study, either alone or in combination with αPD-1, is consistent with a recent report of another ERβ agonist LY500307 in overcoming tumor resistance to ICB immunotherapy (Huang, 2020). Translating these preclinical findings into future anticancer clinical trials leads to novel combination therapies that significantly expand patient populations who can benefit from current immunotherapies.

Example 15

Figure 35:
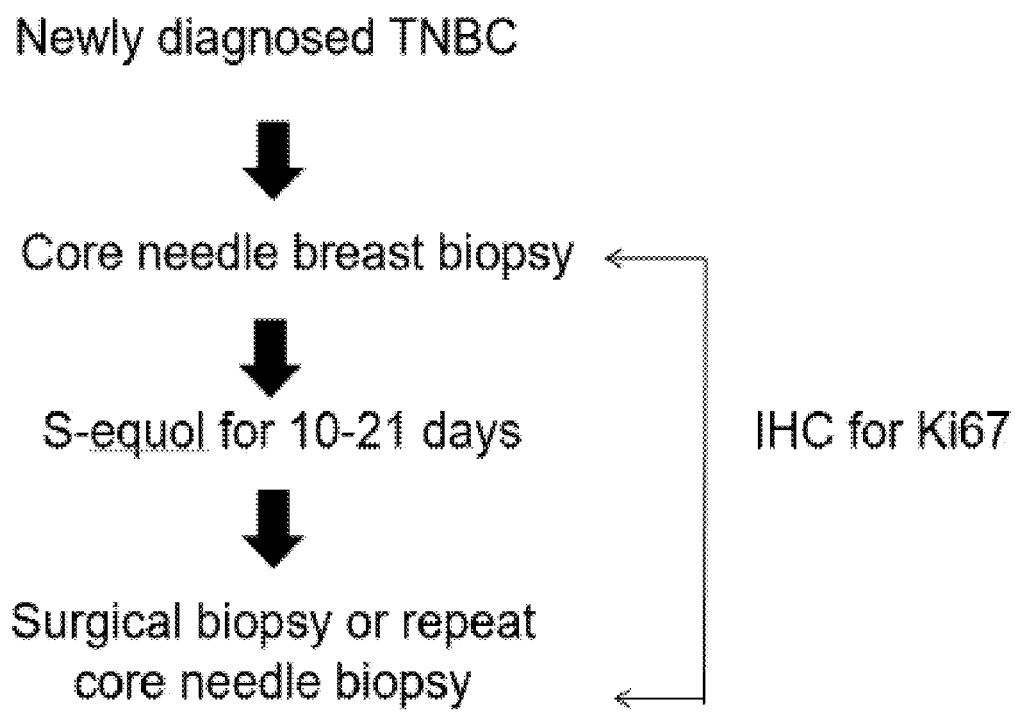
FIG. 35. Clinical trial with TNBC patients. A neoadjuvant window trial was performed on 39 enrolled patients with TNBC confirmed on diagnostic core needle biopsy. Cohort A (20 patients) received a daily dose of 50 mg BID and Cohort B (19 patients) received a higher dose of 150 mg BID for 10-21 days.
Figure 36:
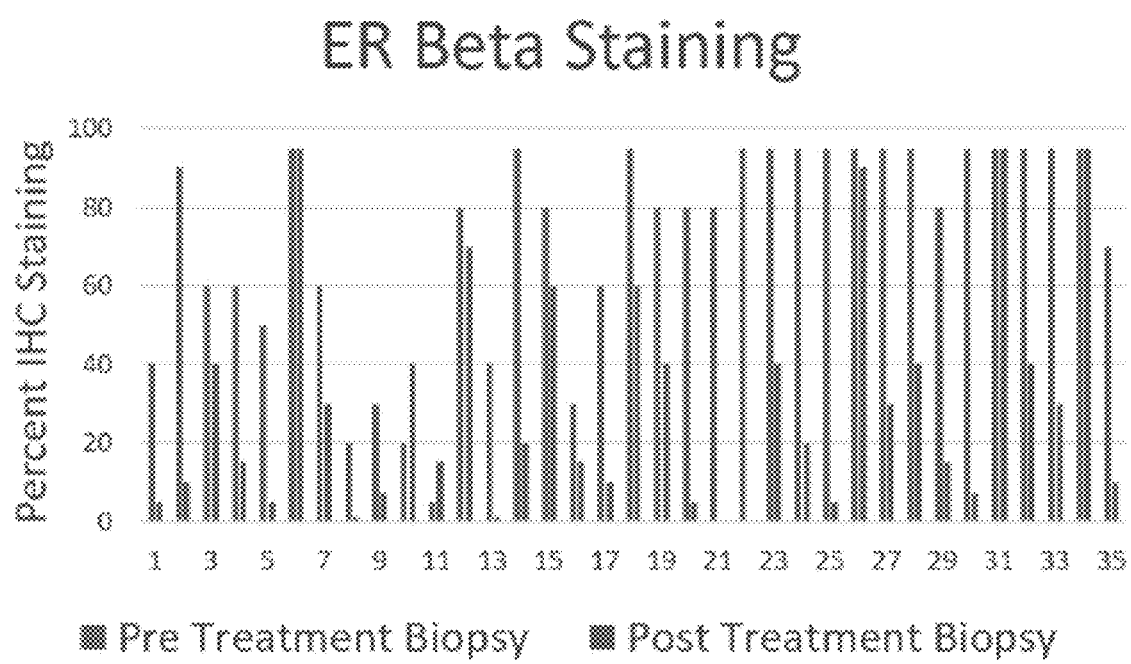
FIG. 36. Effect of treatment on Ki67. Paired biopsies were evaluable for 36 patients. Primary outcome was a change from pre- to post-treatment Ki-67 and secondary outcomes were included as correlative biomarkers. The mean pre-treatment Ki-67 was 68% and posttreatment was 59%. The average decrease in Ki-67 was 8% (P-0.00206, 95% CI −13.46 to −3.26). A Ki-67 decrease of at least 20% from baseline was observed in 28% of the patients. ER Beta IHC expression decreased with exposure to S-equol with a median decrease of 45% (range −65.00 to −19.50).
Figure 37:
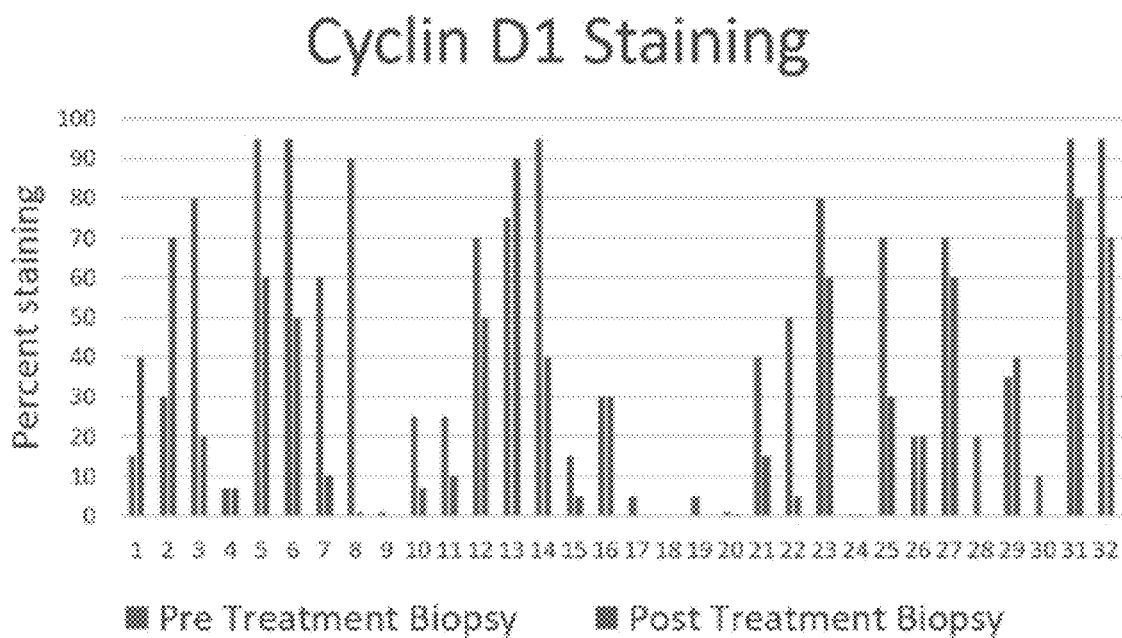
FIG. 37. Effect of treatment on Cyclin D1. Cyclin D1 staining decreased with S-equol exposure with a median decrease of 12.5 (range -27.5-0.0).

TNBC breast cancer have inferior treatment outcomes compared to other breast cancer subtypes, and targeted therapies are lacking. S-equol is a novel oral Estrogen Receptor (ER) Beta agonist with preclinical data showing suppression of TNBC cellular proliferation. A neoadjuvant window trial was performed on 39 enrolled patients with TNBC confirmed on diagnostic core needle biopsy. Cohort A (20 patients) received a daily dose of 50 mg BID and Cohort B (19 patients) received a higher dose of 150 mg BID for 10-21 days. (FIG. 35.) Paired biopsies were evaluable for 36 patients. Primary outcome was a change from pre- to post-treatment Ki-67 and secondary outcomes were included as correlative biomarkers. The mean pre-treatment Ki-67 was 68% and posttreatment was 59%. The average decrease in Ki-67 was 8% (P=0.00206, 95% CI−13.46 to −3.26). A Ki-67 decrease of at least 20% from baseline was observed in 28% of the patients. ER Beta IHC expression decreased with exposure to S-equol with a median decrease of 45% (range−65.00 to −19.50) (FIG. 36.) Cyclin D1 staining also decreased with S-equol exposure with a median decrease of 12.5 (range−27.5-0.0). (FIG. 37.) There was no significant change in CD3 or CD 8 staining in the pre- and post-treatment paired tumor samples.

S-equol is a novel well tolerated oral ER-beta agonist with inhibition of proliferation in patients with TNBC as measured by a decrease in Ki-7. ER-beta expression and cyclin D1 staining by IHC both decreased with exposure to S-equol. CD3 and CD8 expression in the tumor samples did not significantly change with exposure to S-equol.

REFERENCES

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Altin, J. G. and Sloan, E. K. The role of CD45 and CD45-associated molecules in T cell activation. *Immunol. Cell Biol.* 75(5):430-435 (1997).

Azuma, K. & Inoue, S. Genomic and non-genomic actions of estrogen: recent developments. Biomol Concepts 3, 365-370, doi:10.1515/bmc-2012-0002 (2012).

Banerjee, S., Chambliss, K. L., Mineo, C. & Shaul, P. W. Recent insights into non-nuclear actions of estrogen receptor alpha. Steroids 81, 64-69, doi:10.1016/j.steroids.2013.11.002 (2014).

Baum M., Buzdar A. U., Cuzick J., et al. Anastrozole alone or in combination with tamoxifen versus tamoxifen alone for adjuvant treatment of postmenopausal women with early breast cancer: first results of the ATAC randomized trial. *Lancet.* 359: 2131-2139, (2002).

Beelen K., Zwart W., Linn S. C. Can predictive biomarkers in breast cancer guide adjuvant endocrine therapy? *Nat Rev Clin Oncol.* 9: 529-541, (2012).

Bjornstrom, L. & Sjoberg, M. Mechanisms of estrogen receptor signaling: convergence of genomic and nongenomic actions on target genes. Mol Endocrinol 19, 833-842, doi:10.1210/me.2004-0486 (2005).

Brahmer, J. R. et al. Safety and activity of anti-PD-L 1 antibody in patients with advanced cancer. *N Engl J Med* 366, 2455-2465, doi:10.1056/NEJMoal200694 (2012).

Brower, V. Checkpoint blockade immunotherapy for cancer comes of age. *J Natl Cancer Inst* 107, doi: 10.1093/jnci/djv069 (2015).

Chen, L. & Flies, D. B. Molecular mechanisms of T cell co-stimulation and co-inhibition. *Nat Rev Immunol* 13, 227-242, doi:10.1038/nri3405 (2013).

Chia, K. & Tutt, A. Triple-negative breast cancer: An update. *Adv Breast Cancer* 4, 75-80, (2007).

Cho, J. L., Allanson, M. & Reeve, V. E. Oestrogen receptor-beta signalling protects against transplanted skin tumour growth in the mouse. *Photochem Photobiol Sci* 9, 608-614, doi: 10.1039/b9pp00168a (2010).

Clark C A, Gupta H B, Sareddy G, Pandeswara S, Lao S, Yuan B, Drerup J M, Padron A, Conejo-Garcia J, Murthy K, Liu Y, Turk M J, Thedieck K, Hurez V, Li R, Vadlamudi R, Curiel T J. Tumor-Intrinsic P D-L1 Signals Regulate Cell Growth, Pathogenesis, and Autophagy in Ovarian Cancer and Melanoma," *Cancer Res.* 2016 Dec. 1; 76(23):6964-6974.

Clarke R., Liu M., Bouker K. B., et al. Antiestrogen resistance in breast cancer and the role of estrogen receptor signaling. *Oncogene.* 22: 7316-7339, (2003).

Cleator, S., Heller, W. & Coombes, R. C. Triple-negative breast cancer: therapeutic options. *Lancet Oncol.* 8, 235-244, (2007).

Coates et al. "Tailoring therapies—improving the management of early breast cancer: St. Gallen International Expert Consensus on the Primary Therapy of Early Breast Cancer 2015," *Annals of Oncology* 26(8):1533-46, (2015)

Courtney A H, Lo W-L, Weiss A. Tcr signaling: mechanisms of initiation and propagation. *Trends Biochem Sci* 2018; 43:108-23.

Curiel, T. J. et al. Blockade of B7-H1 improves myeloid dendritic cell-mediated antitumor immunity. *Nat Med* 9, 562-567, doi:10.1038/nm863 (2003).

Davies C., Pan H., Godwin J., et al. Long-term effects of continuing adjuvant tamoxifen to 10 years versus stopping at 5 years after diagnosis of estrogen receptor-positive breast cancer: ATLAS, a randomized trial. *Lancet.* 381: 805-816, 2013.

Dawood, S. & Rugo, H. S. Targeting the host immune system: PD-1 and P D-L 1 antibodies and breast cancer. *Curr Opin Support Palliat Care* 10, 336-342, doi: 10.1097/SPC.0000000000000243 (2016).

Dent, R. et al. Triple-negative breast cancer: clinical features and patterns of recurrence. *Clin Cancer Res.* 13, 4429-4434 (2007).

Deroo B. J., Korach K. S. Estrogen receptors and human disease. *J Clin Invest.* 116: 561-570, (2006).

Deroo B. J., Buensuceso A. V. Minireview: Estrogen receptor-beta: mechanistic insights from recent studies. *Mol Endocrinol.* 24: 1703-1714, (2010).

Diaz, L. K., Cryns, V. L., Symmans, W. F. & Sneige, N. Triple negative breast carcinoma and the basal phenotype: From expression profiling to clinical practice. *Advances in Anatomic Pathology* 14, 419-430 (2007).

Dirix, L. Y., Takacs, I. & Nikolinakos, P. e. a. Avelumab (MSB0010718C), an anti-PD-L I antibody, in patients with locally advanced or metastatic breast cancer: A phase 1b J A YELIN solid tumor trial. 2015 San Antonio Breast Cancer Symposium Abstract S1-04, (2015).

Emens, L. A., Braiteh, F. S. & Cassier, P. e. a. Inhibition of P D-L 1 by MPDL3280A leads to clinical activity in patients with metastatic triple-negative breast cancer (TNBC). The American Association for Cancer Research Annual Meeting Abstract 2859, (2015).

Fan, X. et al. Gonadotropin-positive pituitary tumors accompanied by ovarian tumors in aging female ERbeta-/- mice. *Proc Natl Acad Sci USA* 107, 6453-6458, doi: 1002029107 [pii] 10.1073/pnas.1002029107 (2010).

Gerson, R., Alban, F., Villalobos, A. & Serrano, A. Recurrence and survival rates in early breast cancer cases with triple negative immunophenotype. *Gae Med Mex* 144, 27-34, (2008).

Gonzalez-Angulo, A. M. Advances in triple receptor-negative breast cancer. *Clin Adv Hematol Oncol* 5, 956-957 (2007).

Goss P. E., Ingle J. N., Martino S., et al. Randomized trial of letrozole following tamoxifen as extended adjuvant therapy in receptor-positive breast cancer: updated findings from NCIC CTG M A.17. *J Natl Cancer Inst.* 97: 1262-1271, (2005).

Gupta, H. B. et al. "Tumor cell-intrinsic P D-L1 promotes tumor-initiating cell generation and functions in melanoma and ovarian cancer," *Signal Transduction and Targeted Therapy* (2016) 1, 16030.

Haffty, B. G. et al. Locoregional relapse and distant metastasis in conservatively managed triple negative early-stage breast cancer. *J Clin Oncol.* 24, 5652-5657 (2006).

Harris H. A. Estrogen receptor-beta: recent lessons from in vivo studies. *Mol Endocrinol.* 21: 1-13, (2007).

Hartman J., Strom A., Gustafssom J. A. Estrogen receptor beta in breast cancer-diagnostic and therapeutic implications. *Steroids.* 74: 635-641, (2009).

Heldring N., Pike A., Anderrson S., et al. Estrogen receptors: how do they signal and what are their targets. *Physiol Rev.* 87: 905-931, (2007).

Hodi, F. S. et al. Improved survival with ipilimumab in patients with metastatic melanoma. *N Engl J Med* 363, 711-723, doi:10.1056/NEJMoa1003466 (2010).

Honma N., Hori R., Iwase T. et al: Clinical importance of estrogen receptor-beta evaluation in breast cancer patients treated with adjuvant tamoxifen therapy. *J Clin Oncol.* 26: 3727-3734, (2008).

Huang S, Zhou N, Zhao L, et al. Pharmacological activation of estrogen receptor beta overcomes tumor resistance to immune checkpoint blockade therapy. *iScience* 2020; 23:101458.

Irvin, W. J. J. & Carey, L. A. What is triple-negative breast cancer? *Eur J Cancer.* 44, 2799-2805, (2008).

Jackson R. L., Greiwe J. S., Schwen R. J. Emerging evidence of the health benefits of S-equol, an estrogen receptor beta agonist. *Nutr Rev.* 69: 432-448, (2011a).

Jackson R. L., Greiwe J. S., Schwen R. J. Single-dose and steady-state pharmacokinetic studies of S-equol, a potent nonhormonal, estrogen receptor beta-agonist being developed for the treatment of menopausal symptoms. *Menopause,* 18 185-193, (2011b)

Jenks et al., A pilot study on the effects of S-equol compared to soy isoflavones on menopausal hot flash frequency, *Journal of Women's Health,* 21 (2012) 674-682, (2002).

Jiang P, Gu S, Pan D, et al. Signatures of T cell dysfunction and exclusion predict cancer immunotherapy response. *Nat Med* 2018; 24:1550-8.

Kang, S. P., Martel, M. & Harris, L. N. Triple negative breast cancer: current understanding of biology and treatment options. *Curr Opin Obstet Gynecol.* 20, 40-46, (2008).

Kaplan, H. G. & Malmgren, J. A. Impact of triple negative phenotype on breast cancer prognosis. *Breast Journal* 14, 456-463, (2008).

Katzenellenbogen B., Katzenellenbogen J. Estrogen receptor transcription and transactivation: Estrogen receptor alpha and estrogen receptor beta: regulation by selective estrogen receptor modulators and importance in breast cancer. *Breast Cancer Res.* 2: 335-344, (2000).

Kaufman, H. L. et al. The Society for Immunotherapy of cancer consensus statement on tumour immunotherapy for the treatment of cutaneous melanoma. *Nat Rev Clin Oncol* 10, 588-598, doi: 10.1038/nrclinonc.2013.153 (2013).

Kittaneh et al. "Molecular profiling for breast cancer: A comprehensive review," *Biomark Cancer* 5:61-70, (2013).

Krege, J. H. et al. Generation and reproductive phenotypes of mice lacking estrogen receptor beta. *Proc Natl Acad Sci USA* 95, 15677-15682, (1998).

Leung, Y. K. & Ho, S. M. Estrogen receptor beta: switching to a new partner and escaping from estrogen. *Sci Signal* 4, pe19, doi:10.1126/scisignal.2001991 (2011)

Lin, P. Y. et al. B7-H1-dependent sex-related differences in tumor immunity and immunotherapy responses. *J Immunol* 185, 2747-2753, doi:10.4049/jimmunol.1000496 (2010).

Madak-Erdogan, Z. et al. Integrative genomics of gene and metabolic regulation by estrogen receptors alpha and beta, and their coregulators. *Mol Syst Biol* 9, 676, doi:10.1038/msb.2013.28 (2013).

Mak, P., Leung, Y. K., Tang, W. Y., Harwood, C. & Ho, S. M. Apigenin suppresses cancer cell growth through ERbeta. Neoplasia 8, 896-904, doi:10.1593/neo.06538 (2006).

Mak, P. et al. ERbeta impedes prostate cancer EMT by destabilizing HIF-1alpha and inhibiting VEGF-mediated snail nuclear localization: implications for Gleason grading. Cancer Cell 17, 319-332, doi:S1535-6108(10) 00082-6 [pii] 10.1016/j.ccr.2010.02.030 (2010).

Mao, A., Paharkova-Vatchkova, V., Hardy, J., Miller, M. M. & Kovats, S. Estrogen selectively promotes the differentiation of dendritic cells with characteristics of Langerhans cells. J Immunol 175, 5146-5151 (2005).

Marotti, J. D., Collins, L. C., Hu, R. & Tamimi, R. M. Estrogen receptor-beta expression in invasive breast cancer in relation to molecular phenotype: results from the Nurses' Health Study. *Modern Pathology* 23, 197-204, doi:10.1038/modpathol.2009. 158, (2010).

Marzagalli M., et al. Estrogen Receptor β in Melanoma: From Molecular Insights to Potential Clinical Utility, Frontiers in Endocrinology, Vol. 7, Article 140 (2016).

McDonnell D., Norris J.: Connections and regulation of the human estrogen receptor. *Science*. 296: 1642-1644, (2002).

Mellman, I., Coukos, G. & Dranoff, G. Cancer immunotherapy comes of age. *Nature* 480, 480-489, doi:10.1038/nature10673 (2011).

Murphy L. C., Watson P. H. Is oestrogen receptor-beta a predictor of endocrine therapy responsiveness in human breast cancer? *Endocr Relat Cancer.* 13: 327-334, (2006).

Nakajima, Y. et al. Estrogen regulates tumor growth through a nonclassical pathway that includes the transcription factors ERbeta and KLF5. *Sci Signal* 4, ra22, doi:10.1126/scisignal.2001551 (2011).

Nanda, R. et al. Pembrolizumab in patients with advanced triple-negative breast cancer: Phase 1b KEYNOTE-012 Study. *J Clin Oncol* 34, 2460-2467, doi: 10.12005C0.2015.64.8931 (2016).

Nanni, S. et al. Endothelial NOS, estrogen receptor beta, and HIFs cooperate in the activation of a prognostic transcriptional pattern in aggressive human prostate cancer. J Clin Invest 119, 1093-1108, doi:35079 [pii] 10.1172/JCI35079 (2009).

Padrón Á, Hurez V, Gupta H B, Clark C A, Pandeswara S L, Yuan B, Svatek R S, Turk M J, Drerup J M, Li R, Curiel T J. "Age effects of distinct immune checkpoint blockade treatments in a mouse melanoma model," *Exp Gerontol.* 2018 May; 105:146-154.

Pan D, Kobayashi A, Jiang P, et al. A major chromatin regulator determines resistance of tumor cells to T cell-mediated killing. Science 2018; 359:770-5.

Pardoll, D. & Drake, C. Immunotherapy earns its spot in the ranks of cancer therapy. *J Exp Med* 209, 201-209, doi: 10.1084/jem.20112275 (2012).

Pardoll, D. M. The blockade of immune checkpoints in cancer immunotherapy. *Nat Rev Cancer* 12, 252-264, doi: 10.1038/nrc3239 (2012).

Pfefferle, A. D. et al. Transcriptomic classification of genetically engineered mouse models of breast cancer identifies human subtype counterparts. *Genome Biol* 14, R125, doi:10.1186/gb-2013-14-11-r125 (2013).

Phiel, K. L., Henderson, R. A., Adelman, S. J. & Elloso, M. M. Differential estrogen receptor gene expression in human peripheral blood mononuclear cell populations. Immunol Lett 97, 107-113, doi:10.1016/j.imlet.2004.10.007 (2005).

Pierdominici, M. et al. Estrogen receptor profiles in human peripheral blood lymphocytes. Immunol Lett 132, 79-85, doi:10.1016/j.imlet.2010.06.003 (2010).

Reese, J. M. et al. ERβ: characterization, prognosis, and evaluation of treatment strategies in ER alpha positive and -negative breast cancer. *BMC Cancer* 14, 749, doi: 10.1186/1471-2407-14-749 (2014).

Reis-Filho, J. S. & Tutt, A. N. J. Triple negative tumours: A critical review. *Histopathology* 52, 108-118, (2008).

Ribas, A. and Wolchok, J. D. Cancer immunotherapy using checkpoint blockade. *Science* 359:1350-1355, (2018).

Rugo, H. S. et al. Preliminary efficacy and safety of pembrolizumab (MK-3475) in patients with PD-LI-positive, estrogen receptor-positive (ER+)/HER2-negative advanced breast cancer enrolled in KEYNOTE-028. 2015 *San Antonio Breast Cancer Symposium Abstract* S5-07 (2015).

Sachs, J. R. et al. Optimal dosing for targeted therapies in oncology: drug development cases leading by example. Clin. Cancer Res. 22(6):OF1-7 (2016).

Sahin, U. and Tureci, O. Personalized vaccines for cancer immunotherapy. *Science* 359:1355-1356, (2018).

Santen R. J., Brodie H., Simpson E. R., et al. History of aromatase: saga of an important biological mediator and therapeutic target. *Endocr Rev.* 30: 343-375, (2009).

Sareddy, G. R. et al. Therapeutic significance of estrogen receptor beta agonists in gliomas. Mol Cancer Ther 11, 1174-1182, doi:10.1158/1535-7163.MCT-11-0960 (2012).

Schwen, R. J., Greiwe, J. S., Schwen, R. J. Elucidation of the metabolic pathway of s-equol in rat, monkey and man. *Food Chemistry Toxicology.* 50: 2074-2083, (2012).

Setchell, K. D., Clerici C., Lephart E. D., et al. S-equol, a potent ligand for estrogen receptor beta, is the exclusive enantiomeric form of the soy isoflavone metabolite produced by human intestinal bacterial flora. *Am J Clini Nutr.* 81: 1072-1079, (2005).

Setchell, K. D. The clinical importance of the metabolite equol—a clue to the effectiveness of soy and its isoflavones. *Nature.* 132:3577-3584, (2002).

Shaaban A. M., Green A. R., Karthik S. Nuclear and cytoplasmic expression of ERbeta1, ERbeta2, and ERbeta5 identifies distinct prognostic outcome for breast cancer patients. *Clin Cancer Res.* 14: 5228-5235, (2008).

Sharma, P. & Allison, J. P. Immune checkpoint targeting in cancer therapy: toward combination strategies with curative potential. *Cell* 161, 205-214, doi:10.1016/j.cell.2015.03.030 (2015).

Shou J., Massarweh S., Osborne C. K., et al. Mechanisms of tamoxifen resistance: increased estrogen receptor-HER2/neu cross-talk in ER/HER2-positive breast cancer. *J Natl Cancer Inst.* 96: 926-935, 2004.

Smith I. E., Dowsett M., Ebbs S., et al. Neoadjuvant treatment of postmenopausal breast cancer with anastrozole, tamoxifen, or both in combination: The immediate preoperative anastrozole, tamoxifen, or combined with tamoxifen (IMPACT) multicenter double-blind randomized trial. *J Clini Onc.* 23: 5108-5116, (2005).

Smith C. L., O'Malley B. W. Coregulator Function: A Key to Understanding Tissue Specificity of Selective Receptor Modulators. Endocrine Reviews 25(1):45-71, (2004).

Steinberg S M, Shabaneh T B, Zhang P, Martyanov V, Li Z, Malik B T, Wood T A, Boni A, Molodtsov A, Angeles C V, Curiel T J, Whitfield M L, Turk M J. "Myeloid Cells That Impair Immunotherapy Are Restored in Melanomas with Acquired Resistance to BRAF Inhibitors," *Cancer Res.* 2017 Apr. 1; 77(7):1599-1610.

Svoronos, N. et al. Tumor Cell-Independent Estrogen Signaling Drives Disease Progression through Mobilization of Myeloid-Derived Supressor Cells. Cancer Discov, doi: 10.1158/2159-8290.CD-16-0502 (2016).

Thomas C., Gustafsson J. A. The different roles of ER subtypes in cancer biology and therapy. *Nat Rev Cancer.* 11: 597-608, (2011).

Topalian, S. L., Drake, C. G. & Pardoll, D. M. Immune checkpoint blockade: a common denominator approach to cancer therapy. *Cancer Cel* 27, 450-461, doi:10.1016/j.ccell.2015.03.001 (2015).

Topalian, S. L. et al. Survival, durable tumor remission, and long-term safety in patients with advanced melanoma receiving nivolumab. *J Clin Oncol* 32, 1020-1030, doi: 10.12005C0.2013.53.0105 (2014).

Topalian, S. L., Drake, C. G. & Pardall, D. M. Targeting the PD-1/B7-H1(PD-L1) pathway to activate anti-tumor immunity. *Curr Opin Immunol* 24, 207-212, doi:10.1016/j.coi.2011.12.009 (2012).

Urruticoechea A., Smith I., Dowsett M. Proliferation marker Ki-67 in early breast cancer. *Journal of Clinical Oncology* 23:7212-7220, (2005).

Usui et al., Effects of natural S-equol supplements on overweight or obesity and metabolic syndrome in the Japanese, based on sex and equol status, *Clinical endocrinology,* 78 365-372, (2013).

Wang L, Fan J, Thompson LF, et al. Cd73 has distinct roles in nonhematopoietic and hematopoietic cells to promote tumor growth in mice. *J Clin Invest* 2011; 121:2371-82.

Wherry, E. J. & Kurachi, M. Molecular and cellular insights into T cell exhaustion. Nat Rev Immunol 15,486-499, doi:10.1038/nri3862 (2015).

Wolchok, J. D. et al. Nivolumab plus ipilimumab in advanced melanoma. *N Engl J Med* 369, 122-133, doi: 10.1056/NEJMoa1302369 (2013).

Yakimchuk, K., Jondal, M. & Okret, S. Estrogen receptor alpha and beta in the normal immune system and in lymphoid malignancies. *Mol Cell Endocrinol* 375,121-129, doi:10.1016/j.mce.2013.05.016 (2013).

Yao et al., Potentiation of brain mitochondrial function by S-equol and R/S-equol estrogen receptor beta-selective phytoSERM treatments, *Brain Research,* 1514 128-141, (2013).

Yuan, B. et al. A phosphotyrosine switch determines the antitumor activity of ERbeta. *J Clin Invest* 124, 3378-3390, doi:10.1172/JC174085 (2014).

Yuan B., Cheng L., Chiang H. C., et al. Mobilizing E Rβ antitumor activity through a phosphotyrosine switch. *J Clini Invest.* 124(8):3378-90, (2014).

Yuan, B. et al. Tyrosine phosphorylation regulates ERbeta ubiquitination, protein turnover, and inhibition of breast cancer. *Oncotarget,* doi: 10.18632/oncotarget.10018 (2016).

Zhao et al., A select combination of clinically relevant phytoestrogens enhances estrogen receptor β-binding selectivity and neuroprotective activities in vitro and in vivo. *Neuroendocrinology,* 150(2):770-783, (2009).

Zhao L, Huang S, Mei S, et al. Pharmacological activation of estrogen receptor beta augments innate immunity to suppress cancer metastasis. *Proc Natl Acad Sci* USA 2018; 115:E3673-81.

Zipfel P A, Zhang W, Quiroz M, et al. Requirement for Abl kinases in T cell receptor signaling. *Curr Biol* 2004; 14:1222-31.

The invention claimed is:

1. A method of treating triple-negative breast cancer (TNBC) by
increasing tumor-infiltrating CD8+T cells, the method comprising:
administering to said patient a formulation comprising an amount of S-equol in combination with an antibody, wherein the antibody is directed to programmed cell death protein 1 (PD-1), wherein said combination is sufficient to increase tumor-infiltrating CD8+T cells and reduce the size of TNBC tumors.

2. The method of claim 1, wherein the formulation comprises 10-200 mg S-equol.

3. The method of claim 1, wherein the formulation comprises 50-150 mg S-equol.

4. The method of claim 1, wherein the formulation comprises about 50 mg S-equol.

5. The method of claim 1, wherein the formulation comprises about 150 mg S-equol.

6. The method of claim 1, wherein the formulation is administered orally, intravenously, intraperitoneally, or subcutaneously.

7. The method of claim 1, wherein said subject is a human.

8. The method of claim 1, wherein the antibody is pembrolizumab.

9. The method of claim 1, wherein the formulation is substantially free of genistein, daidzein, and/or IBSO03569.

10. The method of claim 1, wherein genistein, daidzein, and/or IBSO03569 are not co-administered with S-equol.

11. The method of claim 1, wherein the formulation is substantially free of R-equol.

12. The method of claim 1, wherein the S-equol is produced chemically.

13. The method of claim 1, wherein the formulation is administered once per day.

14. The method of claim 1, wherein the formulation is administered twice per day.

15. The method of claim 1, wherein the formulation is administered three times per day.

16. The method of claim 1, wherein the formulation is administered four times per day.

* * * * *